US010369189B2

(12) United States Patent
McNamara et al.

(10) Patent No.: US 10,369,189 B2
(45) Date of Patent: Aug. 6, 2019

(54) COMPOSITIONS AND METHODS FOR UNCOUPLING TRKB RECEPTOR FROM PLC GAMMA 1 FOR THE TREATMENT OF EPILEPSY AND ANXIETY-LIKE DISORDER

(71) Applicant: DUKE UNIVERSITY, Durham, NC (US)

(72) Inventors: James O. McNamara, Chapel Hill, NC (US); Xiao-Ping He, Cary, NC (US); Yangzhong Huang, Chapel Hill, NC (US); Bin Gu, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/281,584

(22) Filed: May 19, 2014

(65) Prior Publication Data
US 2015/0018281 A1 Jan. 15, 2015

Related U.S. Application Data

(60) Continuation-in-part of application No. 13/789,617, filed on Mar. 7, 2013, which is a division of application No. 13/030,977, filed on Feb. 18, 2011, now Pat. No. 8,507,438.

(60) Provisional application No. 61/306,714, filed on Feb. 22, 2010.

(51) Int. Cl.
| | |
|---|---|
| *A61K 38/00* | (2006.01) |
| *A61K 38/16* | (2006.01) |
| *A61K 38/04* | (2006.01) |
| *A61K 31/7105* | (2006.01) |
| *C07K 16/28* | (2006.01) |
| *A61K 45/06* | (2006.01) |

(52) U.S. Cl.
CPC .......... *A61K 38/16* (2013.01); *A61K 31/7105* (2013.01); *A61K 38/04* (2013.01); *A61K 45/06* (2013.01); *C07K 16/2863* (2013.01); *C07K 2317/33* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 8,507,438 B2 * | 8/2013 | McNamara | A61K 38/04 514/17.5 |

FOREIGN PATENT DOCUMENTS

WO 2007143119 12/2007

OTHER PUBLICATIONS

Abel, M.S. et al., 1992, Neuromethods: Animal Models of Neurological Disease. Totoway, NJ: Human Press. pp. 153-155. ISBN 0-89603-211-6.
Arroyo, S. et al., "Is Refractory Epilepsy Preventable," 2002, Epilepsia, 43: 437-444.
Bertram, E., "The Relevance of Kindling for Human Epilepsy," 2007, Epilepsia, 48(Suppl. 2): 65-74.
Binder D.K. et al., "Immunohistochemical Evidence of Seizure-Induced Activation of trk Receptors in the Mossy Fiber Pathway of Adult Rat Hippocampus," 1999, J. Neurosci., 19:4616-4626.
Carmant, L. et al., "Effect of kainic acid-induced status epilepticus on inositol-trisphosphate and seizure-induced brain damage in mature and immature animals," 1995, Dev. Brain Res., 89: 67-72.
Chothia et al., "Domain Association in Immunoglobulin Molecules the Packing of Variable Domains," 1985, J. Mal. Biol., 186:651-663.
Creighton T. E., 1983, Proteins: Structure and Molecular Properties, W. H. Freeman & Co., San Francisco, pp. 79-86.
Croll S.D. et al., "Brain-Derived Neurotrophic Factor Transgenic Mice Exhibit Passive Avoidance Deficits, Increased Seizure Severity and in Vitro Hyperexcitability in the Hippocampus and Entorhinal Cortex," 1999, Neuroscience, 93:1491-1506.
Danzer S.C. Et Al, "Altered Regulation of Brain-Derived Neurotrophic Factor Protein in Hippocampus Following Slice Preparation," 2004, Neuroscience, 126:859-869.
Danzer, S.C. et al., "Localization of Brain-Derived Neurotrophic Factor to Distinct Terminals of Mossy Fiber Axons Implies Regulation of Both Excitation and Feedforward Inhibition of CA3 Pyramidal Cells," 2004, J. Neurosci., 24:11346-11355.
Danzer, S.C. et al., "Structural Plasticity of Dentate Granule Cell Mossy Fibers During the Development of Limbic Epilepsy," 2010, Hippocampus, 20:113-124.
Emfors P. et al., "Increased levels of Messenger RNAs for Neurotrophic factors in the Brain during Kindling Epileptogenesis," 1991, Neuron, 7:165-176.
Goussakov, I.V. et al., "Metaplasticity of Mossy Fiber Synaptic Transmission Involves Altered Release Probability," 2000, J. Neurosci., 20: 3434-3441.
He X.P. et al., "Immunohistochemical Evidence of Seizure-Induced Activation of trkB Receptors in the Mossy Fiber Pathway of Adult Mouse Hippocampus," 2002, J Neurosci., 22: 7502-7508.
He X.P. et al., "Conditional Deletion of TrkB but Not BDNF Prevents Epileptogenesis in the Kindling Model," 2004, Neuron, 43: 31-42.
Holmes, K.H. et al., "The N-methyl-D-aspartate antagonists aminophosphonovalerate and carboxypiperazinephosphonate retard the development and expression of kindled seizures," 1990, Brain Res., 506:227-235.
Huang Y.Z. et al., "Zinc-Mediated Transactivation of TrkB Potentiates the Hippocampal Mossy Fiber-CA3 Pyramid Synapse," 2008, Neuron, 57:546-558.

(Continued)

*Primary Examiner* — Olga N Chernyshev
(74) *Attorney, Agent, or Firm* — McDonnell Boehnen Hulbert & Berghoff LLP

(57) ABSTRACT

The invention provides pharmaceutical compositions and methods of use thereof for preventing or ameliorating disorders of the nervous system. More specifically, the invention provides pharmaceutical compositions, including phosphopeptides that when administered disrupt the physical interaction of TrkB with its signaling effector, phospholipase Cγ1 (PLCγ1). The invention further provides method of treatment comprising administering phosphopeptides that uncouple TrkB from PLCγ1 in order to prevent and/or ameliorate nervous system disorders such as epilepsy, anxiety, and seizures.

Figure 3:
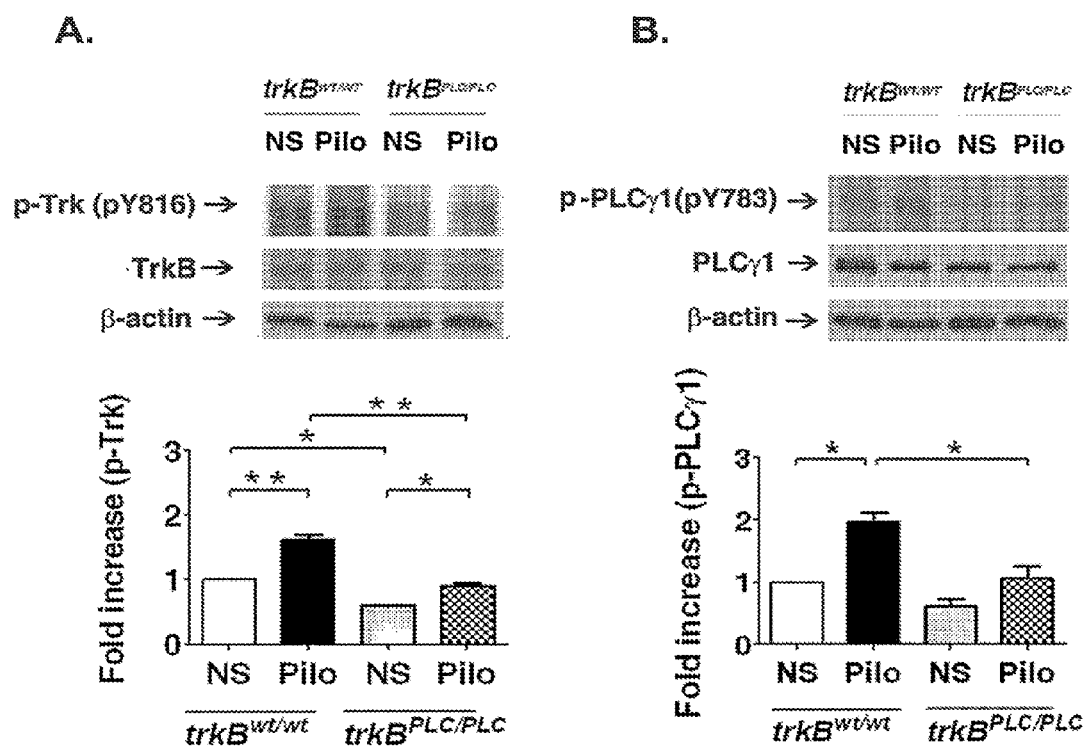

12 Claims, 28 Drawing Sheets
Specification includes a Sequence Listing.

(56) References Cited

OTHER PUBLICATIONS

Isackson P.J. et al., "BDNf mRNA Expression Is Increased in Adult Rat Forebrain after limbic Seizures: Temporal Patterns of Induction Distinct from NGF 1991, Neuron, 6:937-948.
Kim, D. et al., "Phospholipase C isozymes selectively couple to specific neurotransmitter receptors," 1997, Nature, 389: 290-293.
Klitgaard, H. et al., "Pilocarpine-induced epileptogenesis in the rat: Impact of initial duration of status epilepticus on electrophysiological and neuropathological alterations," 2002, Epilepsy Res., 51: 93-107.
Kokaia M. et al., "Suppressed Epileptogenesis in BDNF Mutant Mice," 1995, Exp Neurol, 133: 215-224.
Lemos, T. et al., "Suppression of pilocarpine-induced status epilepticus and the late development of epilepsy in rats," 1995, Exp. Brain Res. 102: 423-428.
Li, Y. et al., "Induction of Mossy Fiber3CA3 Long-Term Potentiation Requires Translocation of Synaptically Released Zn2+," 2001, J. Neurosci., 21: 8015-8025.
Mage et al., 1987, Monoclonal Antibody Production Techniques and Applications, pp. 79-97 (Marcel Dekker, Inc., New York.
McNamara, J.O. et al., "Anticonvulsant and Antiepileptogenic Actions of Mk-801 in the Kindling and Electroshock Models," 1988, Neuropharmacology, 27: 563-568.
McNamara, J.O. et al., "Molecular Signaling Mechanisms Underlying Epileptogenesis," 2006, Sci STKE, 356:re12.
Merlin, L.R. et al., "Role of Group I Metabotropic Glutamate Receptors in the Patterning of Epileptiform Activities in Vitro," 1997, J. Neurophysiol., 78:539-544.
Minichiello L. et al., "Mechanism of TrkB-Mediated Hippocampal Long-Term Potentiation," 2002, Neuron, 36:121-137.
Minichiello, L., et al., "Essential Role for TrkB Receptors in Hippocampus-Mediated Learning," 1999, Neuron, 24:401-414.
Mody, I. et. al., "NMDA receptors of dentate gyrus granule cells participate in synaptic transmission following kindling," 1987, Nature, 326:701-704.
Morimoto, K. et al., "Kindling and status epilepticus models of epilepsy: rewiring the brain," 2004, Prog. Neurobiol. 73: 1-60.
Mouri, G., et al., "Unilateral hippocampal CA3-predominant damage and short latency epileptogenesis after intra-amygdala microinjection of kainic acid in mice," 2008, Brain Research 1213: 140-151.
Murray K.D. et al, "Altered mRNA Expression for Brain-Derived Neurotrophic Factor and Type II Calcium/Calmodulin-Dependent Protein Kinase in the Hippocampus of Patients With Intractable Temporal Lobe Epilepsy," 2000, J Comp Neurol, 418:411-422.
Novotny, J. et al., "Structural invariants of antigen binding: Comparison of immunoglobulin VL-VH and VL-VL domain dimers," 1985, Proc. Natl. Acad. Sci. USA, 82:4592-4596.
Prasad, A. et al., "Phenobarbital and MK-801, but Not Phenytoin, Improve the Long-Term Outcome of Status Epilepticus," 2002, Ann. Neurol., 51: 175-181.
Racine, R.J., et al., "Modification of seizure activity by electrical stimulation: II motor seizure," 1972, Electroencephalogr Clin. Neurophysiol., 32:281-294.
Raza, M. et al., "Evidence that injury-induced changes in hippocampal neuronal calcium dynamics during epileptogenesis cause acquired epilepsy," 2004, Proc. Natl. Acad. Sci. UDS, 101:17522-17527.
Rebecchi, M.J. et al., "Structure, Function, and Control of Phosphoinositide-Specific Phospholipase C," 2000, C. Physiol. Rev., 80: 1291-1335.
Sato, M., 2008, (Kindling: An experimental model of epilepsy, Psychiatry and Clinical Neurosciences, 36:440-441.
Sprengel, R. et al., "Importance of the Intracellular Domain of NR2 Subunits for NMDA Receptor Function in Vivo," 1998, Cell 92: 279-289.
Springer, J.E. et al., "Neurotrophic factor mRNA expression in dentate gyms is increased following in vivo stimulation of the angular bundle," 1994, Mol Brain Res., 23:135-143.
Stasheff, S.F., et al., "NMDA antagonists differentiate epileptogenesis from seizure expression in an in vitro model," 1989, Science, 245:648-651.
Sutula, T. et al., "Facilitation of kindling by prior induction of long-term potentiation in the perforant path," 1987, Brain Res., 420: 109-117.
Takahashi M. et al., "Patients with temporal lobe epilepsy show an increase in brain-derived neurotrophic factor protein and its correlation with neuropeptide Y," 1999, Brain Res 818:579-582.
Toth, K. et al., "Differential Mechanisms of Transmission at Three Types of Mossy Fiber Synapse," 2000, J. Neurosci., 20:8279-8289.
Wolton,et al., "Coexistence of schizophrenia and epilepsy: Record-linkage studies," 2012 Epilepsia, 53:e71-e74.
Xu B. et al., "The Effects of Brain-Derived Neurotrophic Factor (BDNF) Administration on Kindling Induction, Trk Expression and Seizure-Related Morphological Changes," 2004, Neuroscience, 126:521-531.
Alldredge, B.K., et al., "A Comparison of Lorazepam, Diazepam, and Placebo for the Treatment of Out-of-Hospital Epilepticus," 2001, New England Journal of Medicine, 345: 631-637.
Atwal, J.K., et al., "The TrkB-shc Site Signals Neuronal Survival and Local Axon Growth via MEK and P13-Kinase," 2000, Neuron, 27: 265-277.
Blume-Jensen and Hunter, "Oncogenic Kinase Signalling," 2001, Nature, 411: 355-365.
Chen, X., et al., "A Chemical-Genetic Approach to Studying Nurotrophin Signaling," 2005, Neuron, 46: 13-21.
Engel, J., et al., "Mesial Temporal Lobe Epilepsy," 1998, Philadelphia: Lippincott-Raven, 2417-2426.
Felix-Ortiz, A.C., et al., "BLA to vHPC Inputs Modulate Anxiety-Related Behaviors," 2013, Neuron, 79: 658-664.
French, J.A., et al., "Characteristics of Medial Temporal Lobe Epilepsy: I. Results of History and Physical Examination," 1993, Ann Neuroll, 34: 744-780.
Helfer, V., et al., "Amygdala Kindling in the Rat: Anxiogenic-Like Consequences," 1996, Neuroscience, 73: 971-978.
Lemmon, M.A., et al., "Cell Signaling by Receptor Tyrosine Kinases," 2010, Cell, 141: 1117-1134.
Pitkanen, A., "Therapeutic Approaches to Epileptogenesis—Hope on the Horizon," 2010, Epilepsia, 51 (Suppl 3): 2-17.

\* cited by examiner

Figure 1
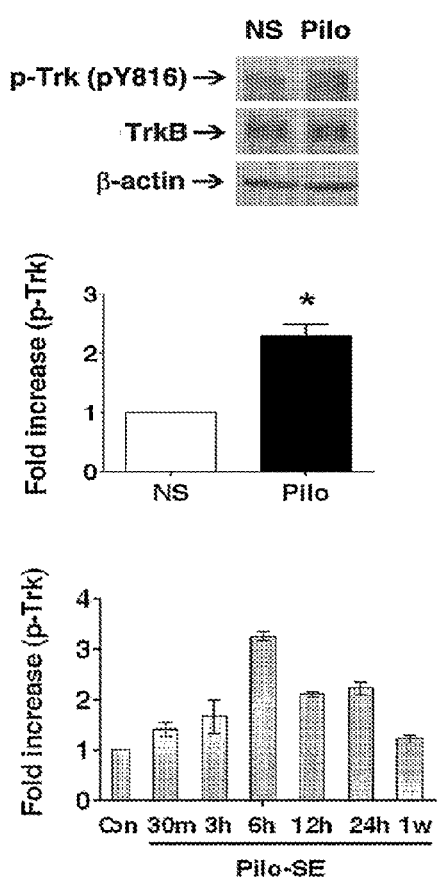
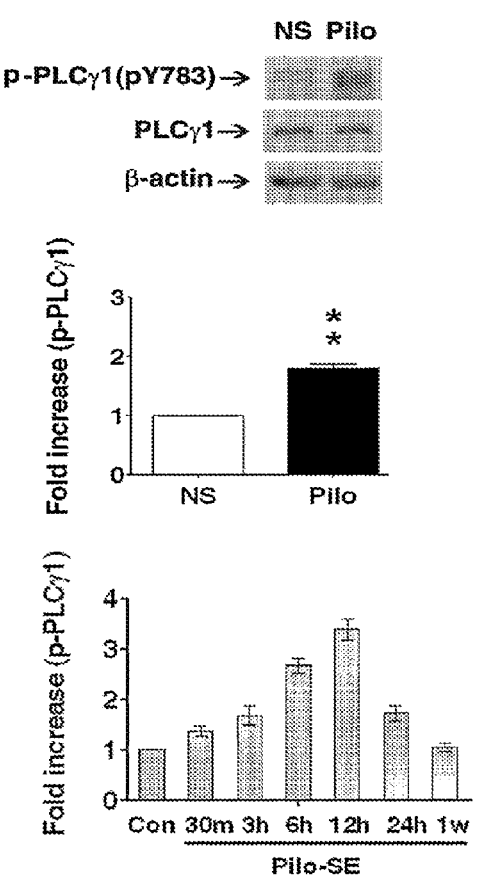

Figure 2
A.
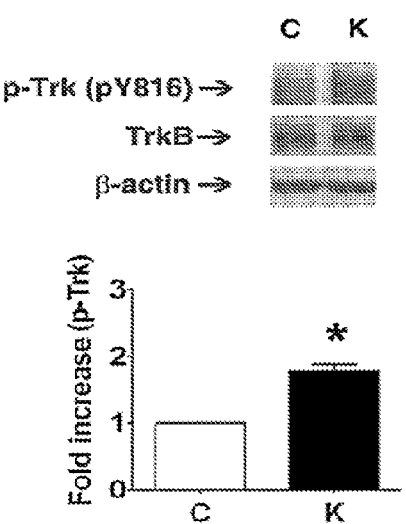
B.
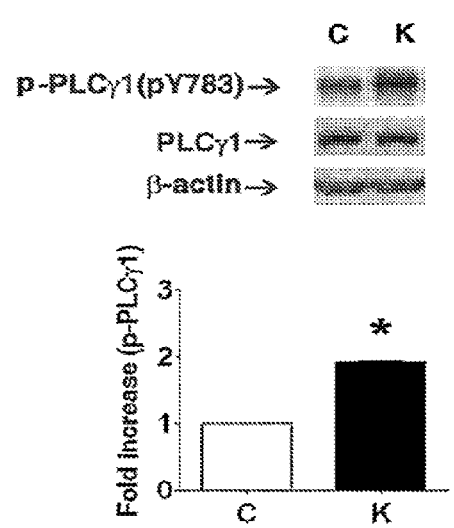

Figure 4
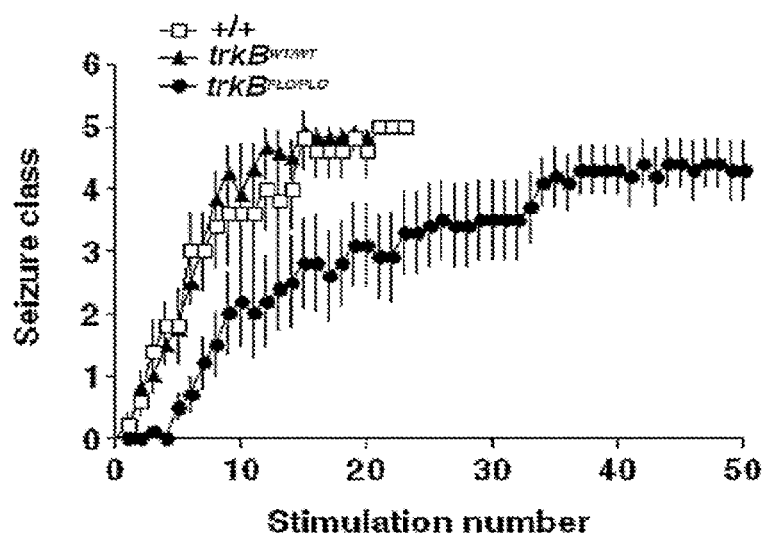
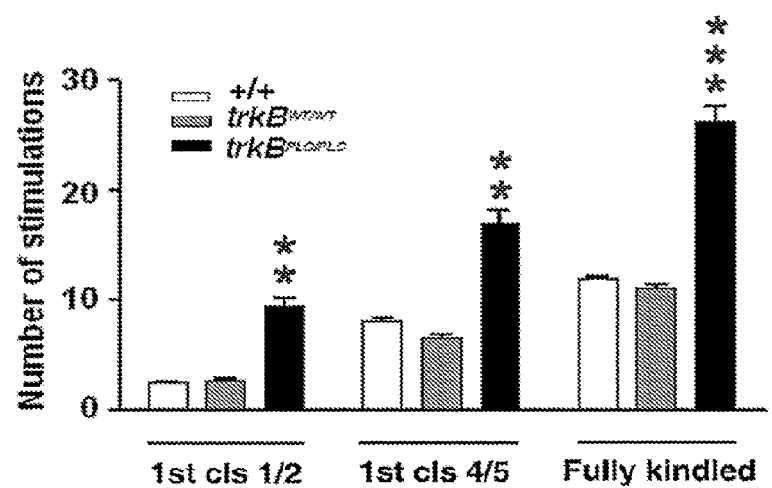

Figure 5
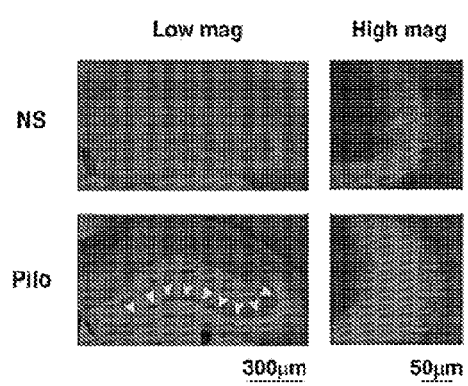
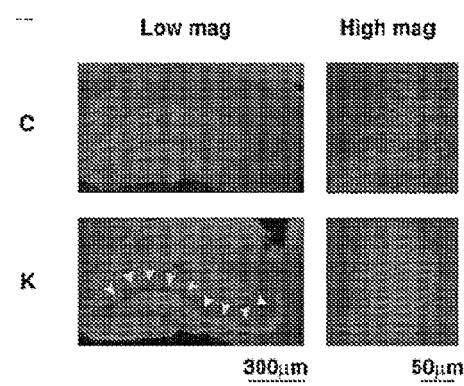
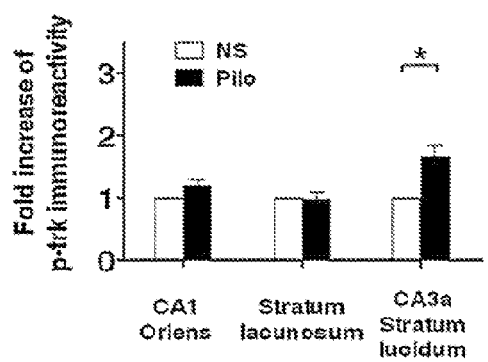
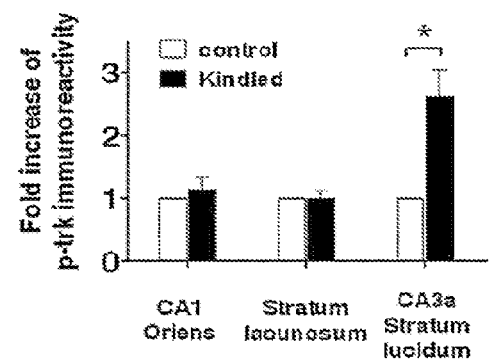

Figure 7
A.
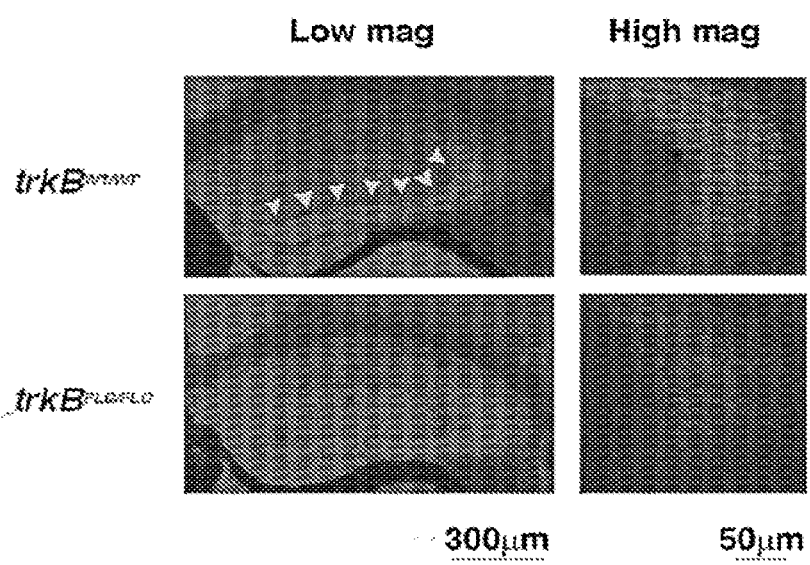
B.
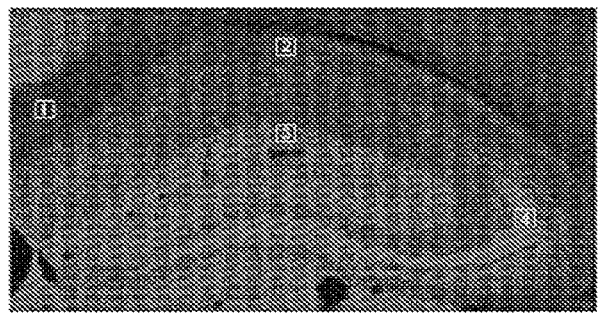

Figure 15
Experimental Design
Time course
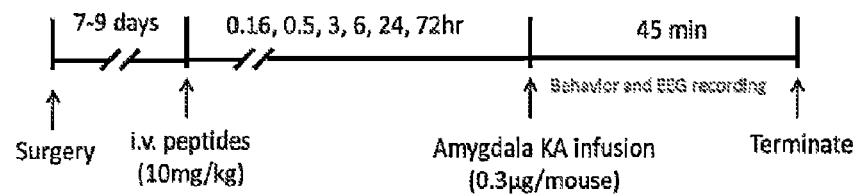
Dose response
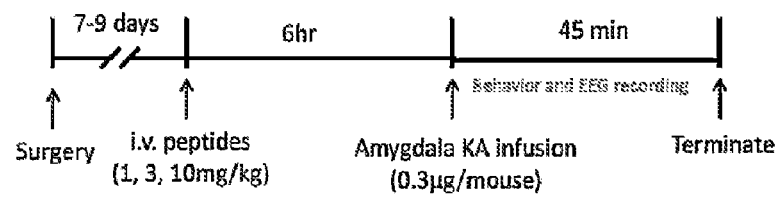

Pretreatment with phospho-Tat-pTrkBY816 inhibits status epilepticus in time dependent fashion (10mg/kg)

Pretreatment with phospho-Tat-pTrkBY816 inhibits status epilepticus in a dose dependent fashion (6hr)

SEQUENCE LISTING

```
<160> NUMBER OF SEQ ID NOS: 6

<210> SEQ ID NO 1
<211> LENGTH: 25
<212> TYPE: PRT
<213> ORGANISM: Artificial Sequence
<220> FEATURE:
<223> OTHER INFORMATION: Synthetic

<400> SEQUENCE: 1

Tyr Gly Arg Lys Lys Arg Arg Gln Arg Arg Leu Gln Asn Leu Ala
1               5                   10                  15

Lys Ala Ser Pro Val Tyr Leu Asp Ile
            20                  25

<210> SEQ ID NO 2
<211> LENGTH: 11
<212> TYPE: PRT
<213> ORGANISM: Artificial Sequence
<220> FEATURE:
<223> OTHER INFORMATION: Synthetic

<400> SEQUENCE: 2

Tyr Gly Arg Lys Lys Arg Arg Gln Arg Arg Arg
1               5                   10

<210> SEQ ID NO 3
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(22)
<223> OTHER INFORMATION: Y is phosphorylated

<400> SEQUENCE: 3

Tyr Gly Arg Lys Lys Arg Arg Gln Arg Arg Leu Gln Asn Leu Ala
1               5                   10                  15

Lys Ala Ser Pro Val Tyr Leu Asp Ile
            20                  25

<210> SEQ ID NO 4
<211> LENGTH: 14
<212> TYPE: PRT
<213> ORGANISM: Artificial Sequence
<220> FEATURE:
<223> OTHER INFORMATION: Synthetic

<400> SEQUENCE: 4

Leu Gln Asn Leu Ala Lys Ala Ser Pro Val Tyr Leu Asp Ile
1               5                   10

<210> SEQ ID NO 5
```

```
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Y is phosphorylated

<400> SEQUENCE: 5

Leu Gln Asn Leu Ala Lys Ala Ser Pro Val Tyr Leu Asp Ile
1               5                   10

<210> SEQ ID NO 6
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: Y is phosphorylated

<400> SEQUENCE: 6

Tyr Gly Arg Lys Lys Arg Arg Gln Arg Arg Arg Leu Val Ala Tyr Gln
1               5                   10                  15

Leu Lys Ile Ala Pro Asn Asp Leu Ser
            20                  25
```

COMPOSITIONS AND METHODS FOR UNCOUPLING TRKB RECEPTOR FROM PLC GAMMA 1 FOR THE TREATMENT OF EPILEPSY AND ANXIETY-LIKE DISORDER

This application is a continuation-in-part of U.S. patent application Ser. No. 13/789,617 filed Mar. 7, 2013, which is a divisional of U.S. patent application Ser. No. 13/030,977 filed Feb. 18, 2011, which claims priority to U.S. provisional patent application, Ser. No. 61/306,714, filed Feb. 22, 2010, the entirety of which are herein incorporated by reference.

PRIORITY AND FEDERAL FUNDING LEGEND

This disclosure was produced in part using funds from the Federal Government under NIH grant no. RO1-NS-078259 entitled "Neurotrophins and Epileptogenesis." Accordingly, the Federal government has certain rights in this disclosure.

FIELD OF THE INVENTION

The present disclosure relates generally to field of neurobiology. Specifically, the present disclosure relates to novel compositions and methods of modulating TrkB signaling and inhibiting TrkB-mediated activation of phospholipase Cγ1 (PLCγ1) for the treatment of neurologic and/or neuropsychiatric conditions, including epilepsy. More particularly, the disclosure provides compositions and methods for disrupting the structural interaction of TrkB and PLCγ1, as well as methods for uncoupling TrkB from PLCγ1 for the treatment of epilepsy, seizures and the prevention of anxiety-like disorder.

BACKGROUND OF THE INVENTION

Epilepsy is a serious common neurological disorder, afflicting an estimated 1% of the population worldwide. Limbic epilepsy (synonyms include complex partial epilepsy, temporal lobe epilepsy, psychomotor epilepsy) is arguably the most devastating form of epilepsy in adults for three main reasons: (1) complex partial seizures constitute the single most common seizure type, accounting for approximately 40% of all cases in adults; (2) complex partial seizures are often quite resistant to available anticonvulsant drugs; and (3) an estimated 30% experience recurrent complex partial seizures despite optimal contemporary treatment (Arroyo, S. et al., (2002) *Epilepsia* 43(4): 437-444). These attacks induce impairment of consciousness, thereby severely limiting performance of many normal functions (e.g., driving, maintaining employment, etc.). Therapy is symptomatic. There is no effective prevention or cure, apart from surgical intervention for a minority.

Understanding the mechanisms of limbic epileptogenesis in cellular and molecular terms may lead to novel and specific therapies aimed at preventing onset and/or progression of this disorder. Extensive experimental evidence supports the assertion that the neurotrophin, brain-derived neurotrophic factor (BDNF), promotes limbic epileptogenesis by activation of its cognate receptor, TrkB. Expression of BDNF is dramatically increased following a seizure in multiple animal models (Ernfors P. et al. (1991) *Neuron* 7(1):165-176; Isackson P. J. et al. (1991) *Neuron* 6(6):937-948; Springer, J. E. et al. (1994) *Brain Res. Mol. Brain Res.* 23 (1-2):135-143); BDNF mRNA and protein content are also increased in the hippocampus of humans with temporal lobe epilepsy (Murray K. D. et al., (2000) *J Comp Neurol* 418(4):411-422; Takahashi M. et al., *Brain Res* 818(2):579-582). Enhanced activation of TrkB has been identified in multiple models of limbic epileptogenesis (Binder D. K. et al. (1999) *J. Neurosci.* 19(11), 4616-4626; Danzer S. C. et al. (2004) *Neuroscience* 126(4):859-869; He X. P. et al., (2002) *J Neurosci* 22(17): 7502-7508). Administration of BDNF and transgenic overexpression of BDNF enhance limbic epileptogenesis (Croll S. D. et al., (1999) *Neuroscience* 93(4):1491-1506; Xu B. et al., (2004) *Neuroscience* 126(3): 521-531). Striking impairments of epileptogenesis in the kindling model were identified in mice carrying only a single BDNF allele, while epileptogenesis was eliminated altogether in mice with a conditional deletion of TrkB in the CNS (Kokaia M. et al., (1995) *Exp Neurol* 133(2): 215-224; He X. P. et al., (2004) *Neuron* 43(1): 31-42).

Insight into the signaling pathways by which TrkB activation promotes limbic epileptogenesis in vivo will aid in the elucidation of the underlying cellular mechanisms as well as aid in the identification of novel targets for therapy. BDNF binding to TrkB results in receptor dimerization, enhanced activity of the TrkB tyrosine kinase which results in phosphorylation of Y515 and Y816 in the intracellular domain of TrkB, thereby creating docking sites for adaptor proteins Shc and PLCγ1 respectively. Both Shc and PLCγ1 are phosphorylated by TrkB, thereby initiating Shc/Ras/MAP kinase and PLCγ1 signaling respectively. Because epileptogenesis was similar in controls and trkB$^{SHC/SHC}$ mutant mice, we hypothesized that PLCγ1 signaling was activated during epileptogenesis in a TrkB-dependent manner and that this activation promotes limbic epileptogenesis. Substitution of phenylalanine for tyrosine at residue 816 of TrkB (pY816 TrkB) in the trkB$^{PLC/PLC}$ mice selectively eliminates binding and phosphorylation of PLCγ1 by TrkB, thereby permitting study of functional consequences of TrkB-mediated activation of PLCγ1 in vivo (Minichiello L. et al., (2002) *Neuron* 36(1), 121-137).

A chemical-genetic approach established proof of concept that transiently inhibiting the receptor tyrosine kinase, TrkB, following SE prevented epilepsy and anxiety-like behavior in a mouse model, providing rationale for developing a therapeutic targeting TrkB signaling. Temporal lobe epilepsy is a common and devastating disorder that is often associated with pathologic anxiety. An episode of prolonged seizures (status epilepticus [SE]) is thought to promote development of human temporal lobe epilepsy years later. In search of a therapeutic, we sought to identify both the TrkB-activated signaling pathway mediating these pathologies and a compound that uncouples TrkB from the responsible signaling effector. To accomplish these goals, we used genetically modified mice and a model of seizures and epilepsy induced by a chemoconvulsant. Genetic inhibition of TrkB-mediated PLCγ1 signaling suppressed seizures induced by a chemoconvulsant, leading to design of a peptide (pY816) that inhibited the interaction of TrkB with PLCγ1. We demonstrate that pY816 selectively inhibits TrkB-mediated activation of PLCγ1 in vitro and in vivo. Treatment with pY816 prior to administration of a chemoconvulsant suppressed seizures in a dose- and time-dependent manner Treatment with pY816 initiated after chemoconvulsant-evoked seizures and continued for just three days suppressed seizure-induction of both epilepsy and anxiety-like behavior assessed months later. This study elucidates the signaling pathway by which TrkB activation produces diverse neuronal activity-driven pathologies and demonstrates therapeutic benefits of an inhibitor of this pathway in an animal model in vivo. A strategy of uncoupling a receptor tyrosine kinase from a signaling effector should prove useful in diverse diseases in which excessive receptor tyrosine kinase signaling contributes.

Receptor tyrosine kinases (RTKs) are a family of cell surface receptors, many of which are important regulators of key cellular processes including proliferation and differentiation, cell migration, and cell cycle control (Blume-Jensen and Hunter, (2001) *Nature* 411:355-365; Lemmon and Schlessinger, (2010) *Cell* 141:1117-1134. The diversity evident in the 58 distinct RTKs in humans notwithstanding, these receptors exhibit similar molecular structures with ligand-binding ectodomains, a single transmembrane domain, and a cytoplasmic component that includes the protein tyrosine kinase domain. These receptors convey signals by coupling ligand binding to the ectodomain to intracellular signaling cascades by recruiting adaptor proteins and enzymes to motifs in the cytoplasmic domain containing distinct tyrosine residues that undergo phosphorylation upon receptor activation. Mutations of RTKs resulting in excessive activation of intracellular signaling pathways cause a diversity of diseases including cancer, diabetes, and arteriosclerosis (Lemmon and Schlessinger, (2010) *Cell* 141: 1117-1134). This led to development of a diversity of FDA-approved drugs, most of which are small molecules that target the ATP-binding site of the kinase domain. While several tyrosine kinase inhibitors have successfully treated some human cancers, emergence of side effects due to lack of target selectivity together with emergence of drug resistance has limited success with this strategy.

The epilepsies constitute a group of common, serious neurological disorders for which no preventive or disease modifying therapy is available. Among the epilepsies, temporal lobe epilepsy (TLE) is the most prevalent and is often devastating both because of its associated behavioral disorders and its resistance to anticonvulsants (Engel J. et al., (1998), Engel J. and T. A. Pedley, eds. (Philadelphia: Lippincott-Raven), pp. 2417-2426). Many patients with severe TLE experienced an episode of continuous seizure activity (SE) years prior to the onset of TLE (French J. A. et al., (1993) *Ann NeuroII* 34:744-780. Because induction of SE alone is sufficient to induce TLE in diverse mammalian species (Pitkanen A., (2010) *Epilepsia* 51 (Suppl 3):2-17), the occurrence of de novo SE is thought to contribute to development of TLE in humans. Recent work identified a molecular mechanism required for induction of TLE by an episode SE, namely, the excessive activation of a tyrosine kinase receptor, TrkB (Liu G. et al., (2013) *Neuron* 79:31-38). A chemical-genetic method (Chen X. et al., (2005) *Neuron* 46:13-21. was used to demonstrate that inhibition of TrkB signaling, initiated following SE and continued for two weeks, prevented both SE-induced TLE and anxiety-like behavior when tested one to two months after SE (Liu G. et al., (2013) *Neuron* 79:31-38).

These findings provide a powerful rationale for developing a drug to selectively inhibit TrkB signaling. Difficulties in developing small molecules that selectively inhibit a single RTK led us to adopt an alternative strategy, namely to identify the downstream signaling pathway by which TrkB kinase activation produced these disorders and to develop a therapeutic targeting this pathway. This study elucidates the signaling pathway by which TrkB activation produces diverse neuronal activity-driven pathologies and demonstrates therapeutic benefits of an inhibitor of this pathway in an animal model in vivo.

SUMMARY OF THE DISCLOSURE

The present disclosure provides compositions and methods for uncoupling a receptor tyrosine kinase (RTK) from a signaling effector, the method comprising inhibiting the physical interaction of an RTK with its signaling effector.

The present disclosure provides treating, preventing onset, and reducing progression of a disorder of the nervous system implicating the TrkB-PLCγ1 signaling pathway. Specifically, the present disclosure provides methods, compositions and strategies to interfere with the TrkB-mediated activation of PLCγ signaling.

One aspect of the disclosure provides a method of uncoupling TrkB from a signaling effector for treating a disorder of the nervous system in a subject, the method comprising inhibiting the physical interaction of TrkB with a signaling effector.

Another aspect of the disclosure provides a method of uncoupling TrkB from a signaling effector for preventing onset or limiting the progression of a disorder of the nervous system in a subject, the method comprising administering to said subject a therapeutically effective amount of an interfering molecule, wherein said interfering molecule inhibits TrkB-interaction with its signaling effector.

One aspect of the disclosure provides a method of preventing epileptic seizures in a subject in need thereof, the method comprising uncoupling TrkB from PLCγ1 by administering a therapeutically effective amount of an interfering molecule, wherein the physical interaction of TrkB with PLCγ1 is reduced.

One aspect of the disclosure provides a method of ameliorating anxiety-like disorder in a subject in need thereof, the method comprising uncoupling TrkB from PLCγ1 by administering a therapeutically effective amount of an interfering molecule, wherein the physical interaction of TrkB with PLCγ1 is reduced.

One aspect of the disclosure provides a method of treating a disorder of the nervous system in a subject comprising, consisting of, or consisting essentially of administering to the subject a therapeutically effective amount of an interfering molecule, wherein the interfering molecule is capable of disrupting TrkB-mediated activation of PLCγ1.

Another aspect of the present disclosure provides a method of ameliorating a disorder of the nervous system in a subject comprising, consisting of, or consisting essentially of administering to the subject a therapeutically effective amount of an interfering molecule, wherein the interfering molecule is capable of disrupting TrkB-mediated activation of PLCγ1.

Another aspect of the present disclosure provides a method for preventing onset or limiting the progression of a disorder of the nervous system in a subject comprising, consisting of, or consisting essentially of administering to the subject a therapeutically effective amount of an interfering molecule capable of disrupting TrkB-mediated activation of PLCγ1.

Another aspect of the present disclosure provides an isolated phosphopeptide comprising the amino acid sequence YGRKKRRQRRRLQNLAKASPVpYLDI (SEQ ID NO:1), wherein the amino acid at position 22 is phosphorylated. In certain embodiments, the isolated phosphopeptide further comprises a tat peptide sequence fused to the peptide. In certain embodiments the tat peptide is fused to amino acid 1. In preferred embodiments, the tat peptide sequence comprises the amino acid sequence YGRKKRRQRRR (SEQ ID NO:2).

In certain embodiments, the interfering molecule is capable of inhibiting the activity of PLCγ1. In other embodiments, the interfering molecule is capable of inhibiting the activity of TrkB. In one embodiment, the interfering molecule is selected from the group consisting of a peptide, a phosphopeptide, peptide fragment, amino acids, an antibody, an antisense or small interfering RNA molecule, a small molecule, a dominant negative form of PLCγ1 and combinations thereof. In preferred embodiments, the interfering molecule is capable of permeating the blood brain barrier. More preferably, the interfering molecule is a phosphopeptide comprising the sequence YGRKKRRQRRRLQNLAKASPVpYLDI (SEQ ID NO:3), wherein Y816 (amino acid number is in mouse TrkB receptor) is phosphorylated (designated by p). In certain embodiments, the antibody is specific for TrkB. In other embodiments, the antibody is specific for PLCγ1.

Other embodiments of the present disclosure provide a pharmaceutical composition in unit dosage form comprising per unit dosage a range of from about 0.01 mg to about 1000 mg of the phosphopeptide or a pharmaceutically acceptable salt thereof, and a pharmaceutically acceptable carrier. In certain embodiments, the range is from about 1 mg to about 500 mg. In certain embodiments, a dosage range is from about 0.001 mg/kg to about 100 mg/kg. In a preferred embodiment, the dosage range is from about 1 mg/kg to about 10 mg/kg.

Another embodiment of the disclosure provides a kit useful for the treatment of a disorder of the nervous system in a subject comprising a therapeutically effective amount of the isolated phosphopeptide and instructions for use.

In certain embodiments, the disorder of the nervous system is selected from the group consisting of stroke, anxiety, head trauma, migraine, pain, schizophrenia, depression, affective disorders, addiction, epilepsy, obsessive compulsive disorder, and combinations thereof. In certain embodiments, the disorder of the nervous system is epilepsy.

In another embodiment, the subject is a mammal. In other embodiments, the subject is a human.

These and other novel features and advantages of the disclosure will be fully understood from the following detailed description and the accompanying drawings.

FIGURES AND DRAWINGS

FIGS. 1A and 1B: TrkB-PLCγ1 signaling is increased in the pilocarpine (pilo) model. FIG. 1A (top): representative Western blot of pY816 TrkB and TrkB in hippocampal homogenate isolated 6 hours after onset of status epilepticus. FIG. 1A (middle): quantitative analysis of Western blot data 6 hours after pilo. The fold increase of pY816 relative to TrkB in pilo group (n=7) is significantly higher than in normal saline (NS) controls (n=6) (p=0.048). Data are presented as means±S.E.M., Student's t test. FIG. 1A (bottom): quantitative analysis of Western blot of pY816 TrkB at multiple times (30 min, 3 h, 6 h, 12 h, 24 h and 1 week) after onset of pilo-induced status epilepticus. Western blots were quantified and presented as mean±S.E.M. of fold increase of pY816 relative to TrkB in pilo mice (n=4 for each time point) compared with NS controls (n=4). Note that different groups of animals were studied at 6 hours after pilo in middle panel compared to bottom panel. FIG. 1B (top): representative Western blot of pY783 PLCγ1 and PLCγ1 in hippocampal homogenate isolated 6 hours after onset of status epilepticus. FIG. 1B (middle): quantitative analysis of Western blot data 6 hours after pilo. The fold increase of pY783 relative to PLCγ1 in pilo group (n=7) is significantly higher than in NS controls (n=6) (p=0.004). Data are presented as means±S.E.M, Student's t test. FIG. 1B (bottom): quantitative analyses of Western blot of pY783 relative to PLCγ1 immunoreactivity at multiple times after pilo-induced status epilepticus. Data are presented as mean±S.E.M. of fold increase of pY783 relative to PLCγ1 in pilo mice (n=4 for each time point) compared with NS controls (n=4). Note that different groups of animals were studied at 6 hours after pilo in middle panel compared to bottom panel.

FIGS. 2A and 2B: TrkB-PLCγ signaling is increased in the kindling model. FIG. 2A (top): representative Western blot of pY816 TrkB and TrkB in hippocampal homogenate isolated 6 hours after last stimulation-induced Class 4/5 kindled seizure. FIG. 2A (Bottom): quantitative analysis of Western blot. The fold increase of pY816 relative to TrkB in kindled mice (K) (n=4) is significantly higher than that in control mice (C) (n=3) (p=0.037). Data are presented as means±S.E.M., Student's t test. FIG. 2B (Top):, representative Western blot of pY783 PLCγ1 and PLCγ1 in hippocampal homogenate isolated 6 hours after last Class 4/5 kindled seizure. FIG. 2B (Bottom): quantitative analysis of Western blot. The fold increase of pY783 relative to PLCγ1 in K (n=4) is significantly higher than in C (n=3) (p=0.034). Data are presented as means±S.E.M., Student's t test.

FIGS. 3A and 3B: Effect of trkB$^{PLC/PLC}$ mutation on TrkB-PLCγ signaling. FIG. 3A (Top): representative Western blot of pY816 TrkB and TrkB in hippocampal synaptosomal membranes isolated 6 hours after onset of pilo-induced status epilepticus from trkB$^{PLC/PLC}$ or trkB$^{WT/WT}$ mice. FIG. 3A (Bottom): quantitative analysis of Western blot. The fold increases of pY816 to TrkB from 3 experiments in trkB$^{PLC/PLC}$ were compared with that from trkB$^{WT/WT}$ mice. Data are presented as means±S.E.M., one-way ANOVA (p<0.001). FIG. 3B (Top): representative Western blot of pY783 PLCγ1 and PLCγ1 in hippocampal synaptosomal membranes isolated 6 hours after onset of pilo-induced status epilepticus from trkB$^{PLC/PLC}$ or trkB$^{WT/WT}$ mice. FIG. 3B (Bottom): quantitative analysis of Western blot. The fold increases of pPLCγ1 relative to PLCγ1 from 3 experiments in trkB$^{PLC/PLC}$ were compared with that from trkB$^{WT/WT}$ mice. Data are presented as means±S.E.M., one-way ANOVA (p=0.022).

FIGS. 4A and 4B: FIG. 4A: Kindling development is inhibited in trkB$^{PLC/PLC}$ mutants. Kindling development is presented as behavioral seizure class (y axis). Stimulation number (x axis) refers to the number of stimulations that evoked an electrographic seizure with duration of at least 5 s. FIG. 4B: number of stimulations required to reach different seizure classes in wild type (+/+) (n=12), trkB$^{WT/WT}$ (n=12), and trkB$^{PLC/PLC}$ (n=10). Fully kindled stage is defined by the occurrence of three consecutive seizures of class 4 or 5. For the number reaching 1$^{st}$ class 1 or 2, +1+ versus trkB$^{PLC/PLC}$, p=0.004; trkB$^{WT/WT}$ versus trkB$^{PLC/PLC}$, p=0.006. For the number reaching 1$^{st}$ class 4 or 5, +1+ versus trkB$^{PLC/PLC}$=0.013; trkB$^{WT/WT}$ versus trkB$^{PLC/PLC}$, p=0.003. For the number reaching fully kindled stage, +/+ versus trkB$^{PLC/PLC}$, p=0.002; trkB$^{WT/WT}$ versus trkB$^{PLC/PLC}$, p=0.001. All data are presented as mean±S.E.M.; one-way ANOVA with post hoc Bonferroni's test.

FIGS. 5A and 5B: Immunohistochemical localization of pY816 TrkB Immunoreactivity in limbic epileptogenesis. FIG. 5A shows pY816 immunoreactivity is increased in pilo model. FIG. 5A (top) is representative images in low magnification (low mag) and high magnification (high mag), from stratum lucidum of CA3a in hippocampus of pY816 immunoreactivity in sections prepared 6 hours after onset of status epilepticus. Note that the increased pY816 immunoreactivity was found mainly in the mossy fiber pathway as denoted by arrowheads. FIG. 5A (bottom) shows quantitative analysis of pY816 immunoreactivity in hippocampal subregions of mice treated with normal saline (NS) or after six hours of pilo-induced status epilepticus (pilo). The pY816 immunoreactivity in CA3a stratum lucidum was increased 1.66 fold in pilo (n=6) compared to NS (n=5) treated group (p=0.015). Data are presented as means±S.E.M., Student's t test. FIG. 5B shows pY816 immunoreactivity is increased in the kindling model. FIG. 5B (top) is representative images in low magnification (low mag) and high magnification (high mag) of pY816 TrkB immunoreactivity in hippocampal sections prepared 6 hours after last stimulation-induced Class 4/5 kindled seizure. Note the increased pY816 immunoreactivity in the mossy fiber pathway as denoted by arrowheads. FIG. 5B (bottom) is quantitative analysis of pY816 immunoreactivity in hippocampal subregions of kindled and control mice. The pY816 immunoreactivity in CA3a stratum lucidum was increased 2.60 fold in kindled (n=4) compared to control group (n=3) (p=0.033). Data are presented as means±S.E.M., Student's t test. Scale bar, 300 μm in low magnification; 50 μm in high magnification.

Figure 6:
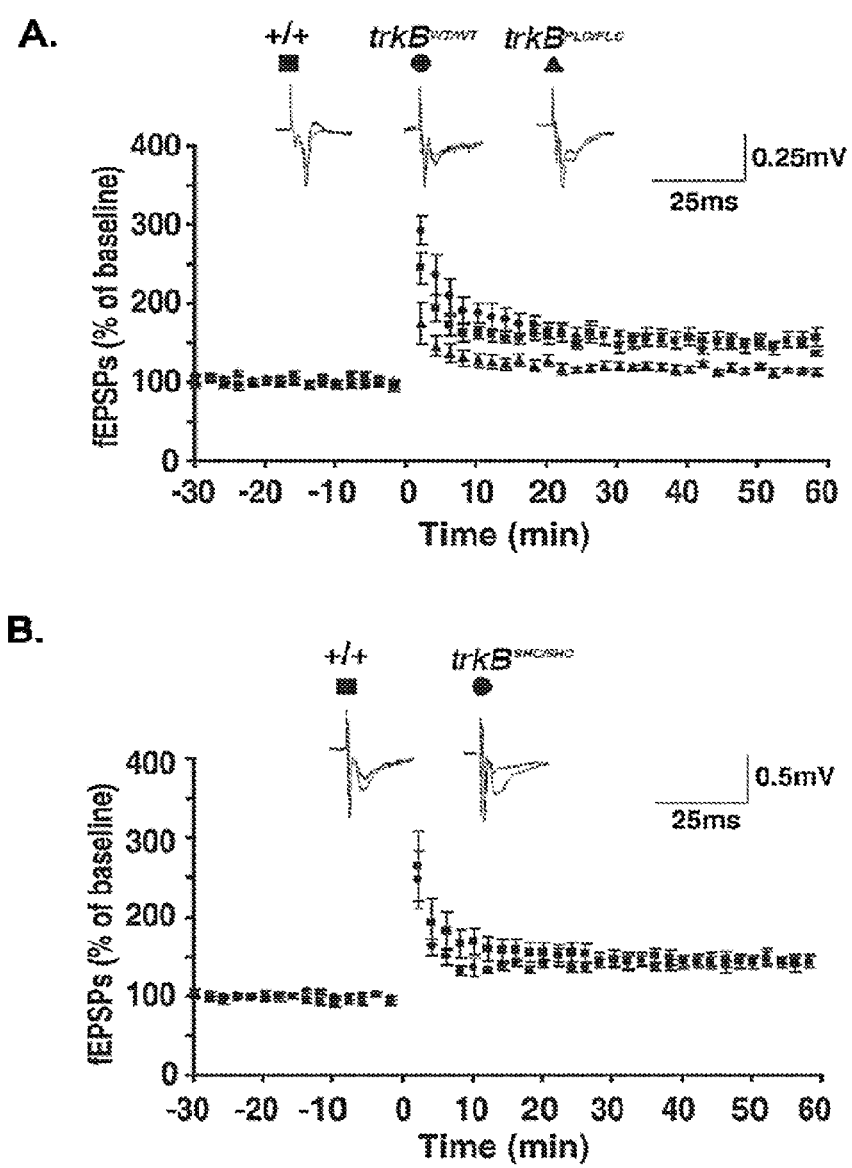

FIGS. 6A and 6B: Mf-CA3 LTP is impaired in TrkB$^{PLC/PLC}$ mutants. Hippocampal slices were isolated from wild type or mutant mice and mf-evoked fEPSPs were recorded. Graphs represent mean±S.E.M. of the responses evoked compared to baseline. Traces of representative experiments are shown above each graph. FIG. 6A: High frequency stimulation (HFS)-induced mf LTP is impaired in TrkB$^{PLC/PLC}$ mutant mice. Significant (p<0.01) impairments of HFS-induced LTP of the mf-CA3 pyramid synapse were detected in slices isolated from trkB$^{PLC/PLC}$ (115±3%, n=7) compared to WT (155±9%, n=8) or trkB$^{WT/WT}$(148±3.9%, n=7) control mice. Slices isolated from trkB$^{WT/WT}$ mice exhibited increases of fEPSP (148±3.9%, n=7) similar to wild type animals (+/+) (155±9%, n=8). Scale bar: 0.25 mV, 25 ms. FIG. 6B: By contrast, no differences in HFS-induced LTP of the mf-CA3 pyramid synapse were detected in trkB$^{SHC/SHC}$ compared to WT control mice (+/+, 144±7%, n=6; trkB$^{SHC/SHC}$, 145±7%, n=5, P>0.05, t test). Scale bar: 0.5 mV, 25 ms.

FIGS. 7A and 7B: FIG. 7A: Specificity of pY816 antibody for immunohistochemistry. Representative images in low magnification (low mag) and high magnification (high mag) from stratum lucidum of CA3a in hippocampus of pY816 immunoreactivity in sections prepared from trkB$^{WT/WT}$ and trk$^{PLC/PLC}$ mice. Note pY816-ir is decreased in trkB$^{PLC/PLC}$ compared to trkB$^{WT/WT}$ mice, establishing specificity of antibody for pY816. Similar results were obtained in other 2 experiments. Mice were sacrificed and coronal sections prepared as described in methods. Scale bars: 300 μm in low magnification; 50 μm in high magnification. FIG. 7B: Boxes denote locations within hippocampal formation at which pY816 immunoreactivity was sampled for quantitative analyses 1, corpus callosum; 2, CA1 Oriens; 3, CA1 stratum lacunosum-moleculare; 4, CA3a stratum lucidum.

Figure 8:
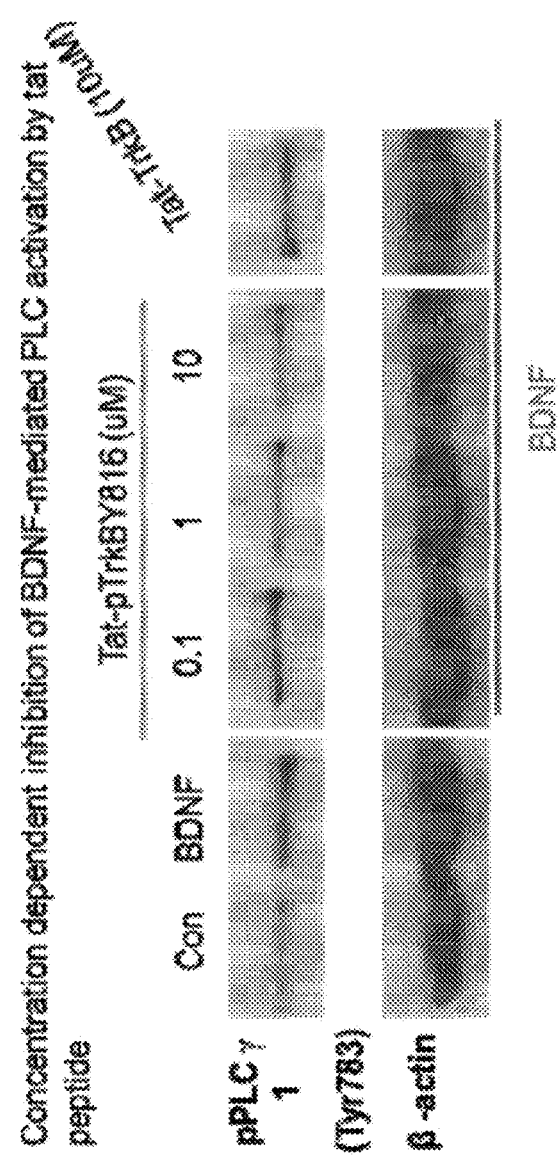

FIG. 8: Cultured rat embryonic cortical neurons were preincubated with Tat-pTrkBY816 at 0.1 μM, 1 μM or 10 μM for 90 mins prior to BDNF stimulation (10 ng/ml, 15 mins) and cell lysate was prepared for immunoblotting. Preincubation of the neurons with 1 μM and 10 μM Tat-pTrkBY816 inhibited the BDNF-induced increase of phospho-PLCγ1 (Y783) in a concentration dependent manner.

Figure 9:
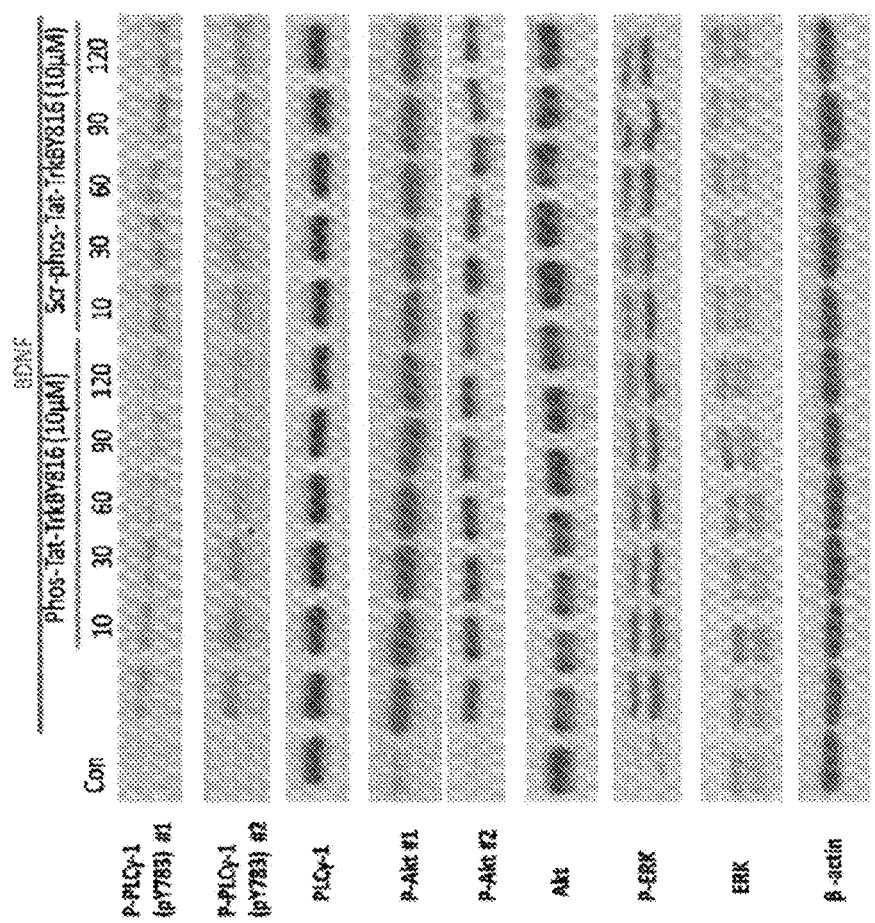

FIG. 9: Embryonic (E18) rat cortical neurons cultured for 12 DIV were used in these experiments. Either phospho-Tat-TrkBY816 peptide (10 μM) or scrambled phospho-Tat-TrkBY816 was added to the neurons for varying periods of time (10, 30, 60, 90 and 120 mins) prior to addition to BDNF (10 ng/ml). Following 15 min incubation with BDNF or vehicle, cells were solubilized and lysates were subjected to SDS-PAGE and western blotting with a diversity of antibodies. Preincubation with phospho-Tat-TrkBY816 peptide (10 μM) for periods ranging from 60-120 min inhibited BDNF-mediated increased p-PLCγ1 783; this inhibition was selective in that BDNF-mediated increases of pAkt and pErk were not affected. The inhibition of p-PLCγ1 783 by phospho-Tat-TrkBY816 was also selective in that no inhibition was evident in neurons preincubated with scrambled phospho-Tat-TrkBY816 (10 μM).

Figure 10:
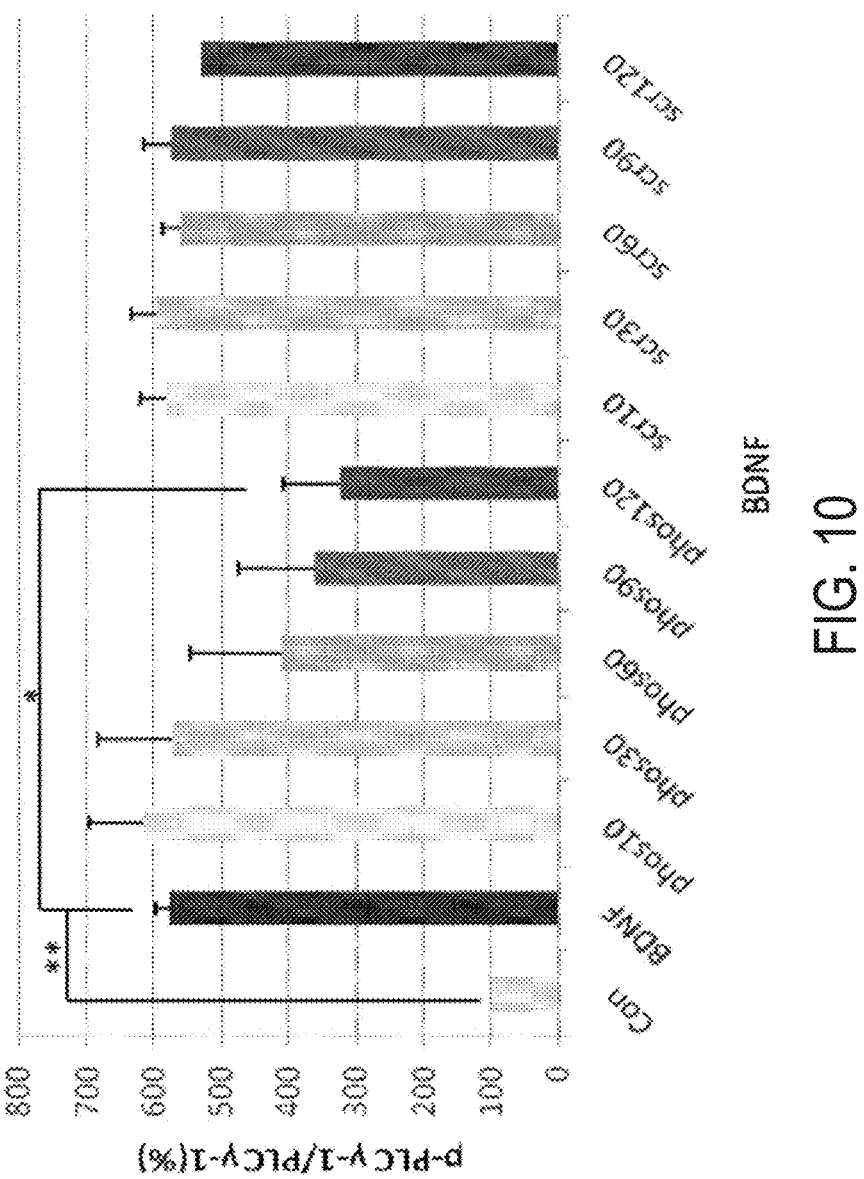

FIG. 10: The results presented in FIG. 9 were quantified and are presented in FIG. 10 in which values represent means±SEM of two or three experiments. Phospho-Tat-TrkBY816 peptide inhibited the BDNF-mediated increase of p-PLC γ-1/PLC γ-1 ratio in a time dependent manner (120 min pretreatment, *p<0.05) but the Scrambled-phospho-Tat-TrkBY816 peptide was ineffective. Neither peptide affected p-Akt/Akt or p-ERK/ERK ratio nor did the Scrambled-phospho-Tat-TrkBY816 peptide affect the p-PLC γ-1/PLC γ-1 ratio.

Figure 11:
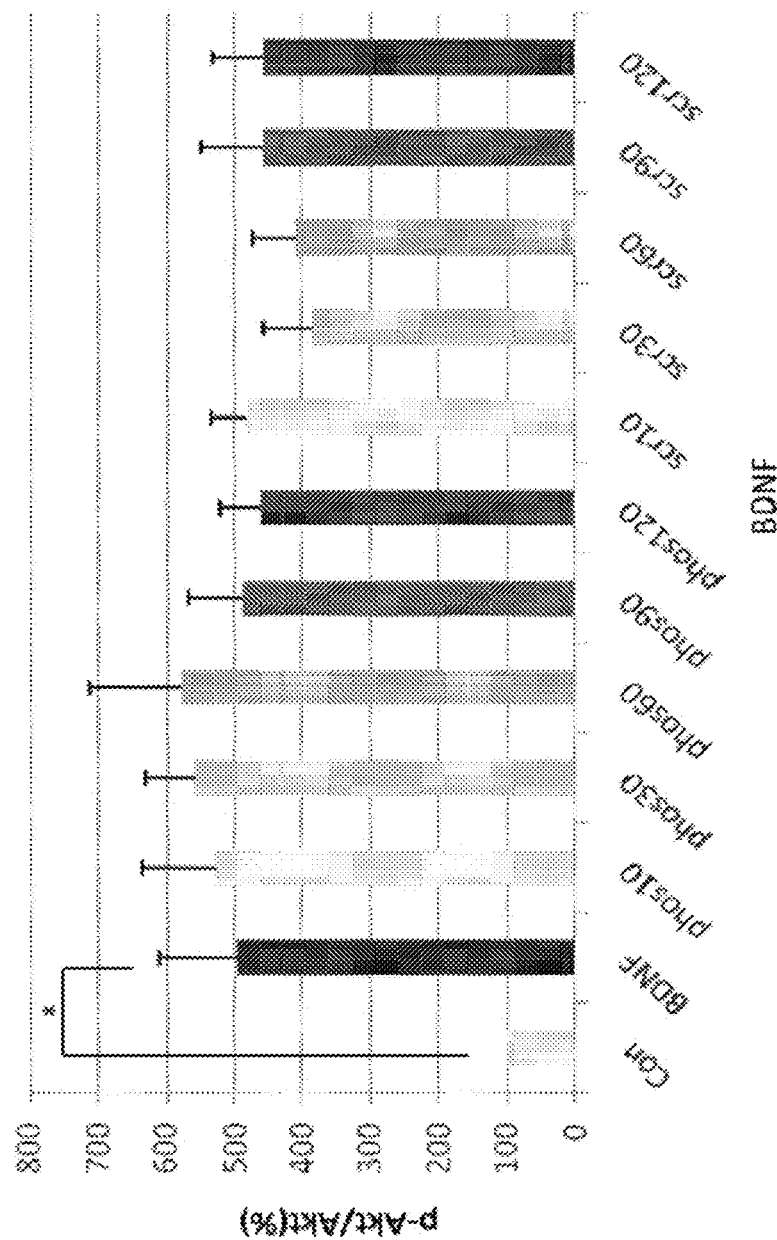

FIG. 11: The results presented in FIG. 9 were quantified and are presented in FIG. 11 in which values represent means±SEM of two or three experiments. Neither the Phospho-Tat-TrkBY816 nor the Scr-phospho-Tat-TrkBY816 peptide inhibited the BDNF-mediated increase of the p-Akt/Akt ratio.

Figure 12:
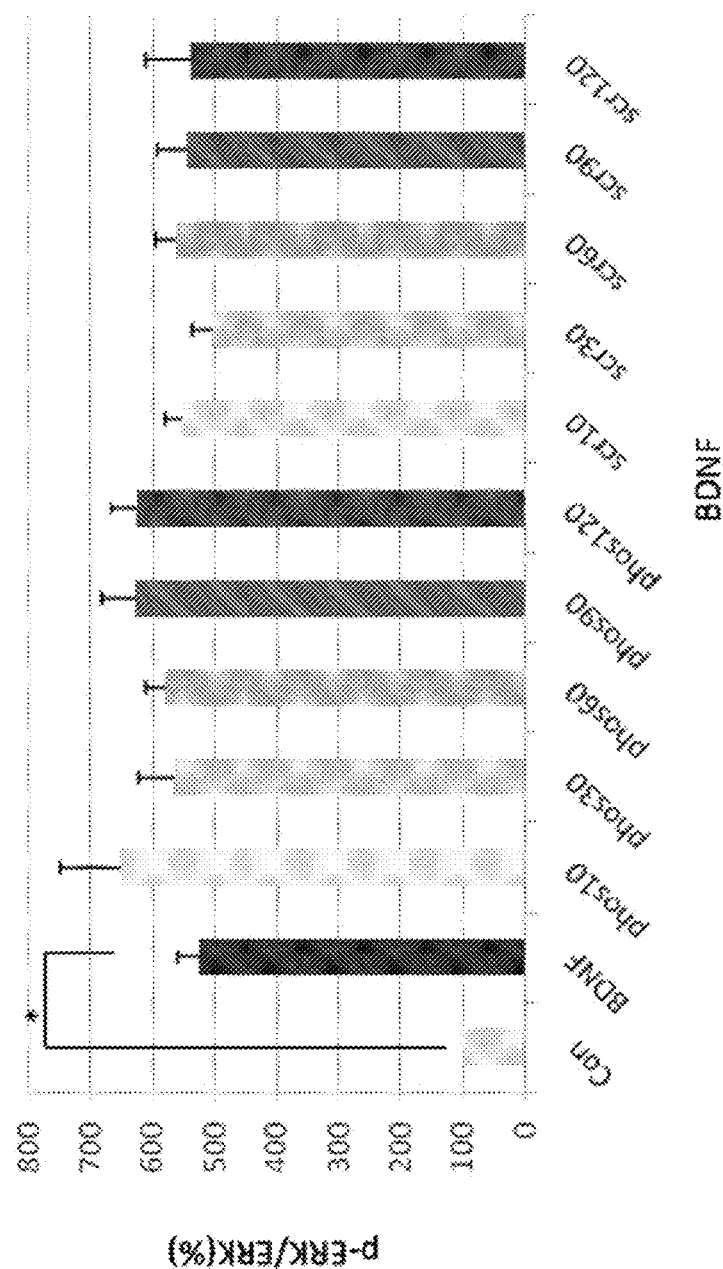

FIG. 12: The results presented in FIG. 9 were quantified and are presented in FIG. 12 in which values represent means±SEM of two or three experiments. Neither the Phospho-Tat-TrkBY816 nor the Scr-phospho-Tat-TrkBY816 peptide inhibited the BDNF-mediated increase of the p-ERK/ERK ratio.

Figure 13:
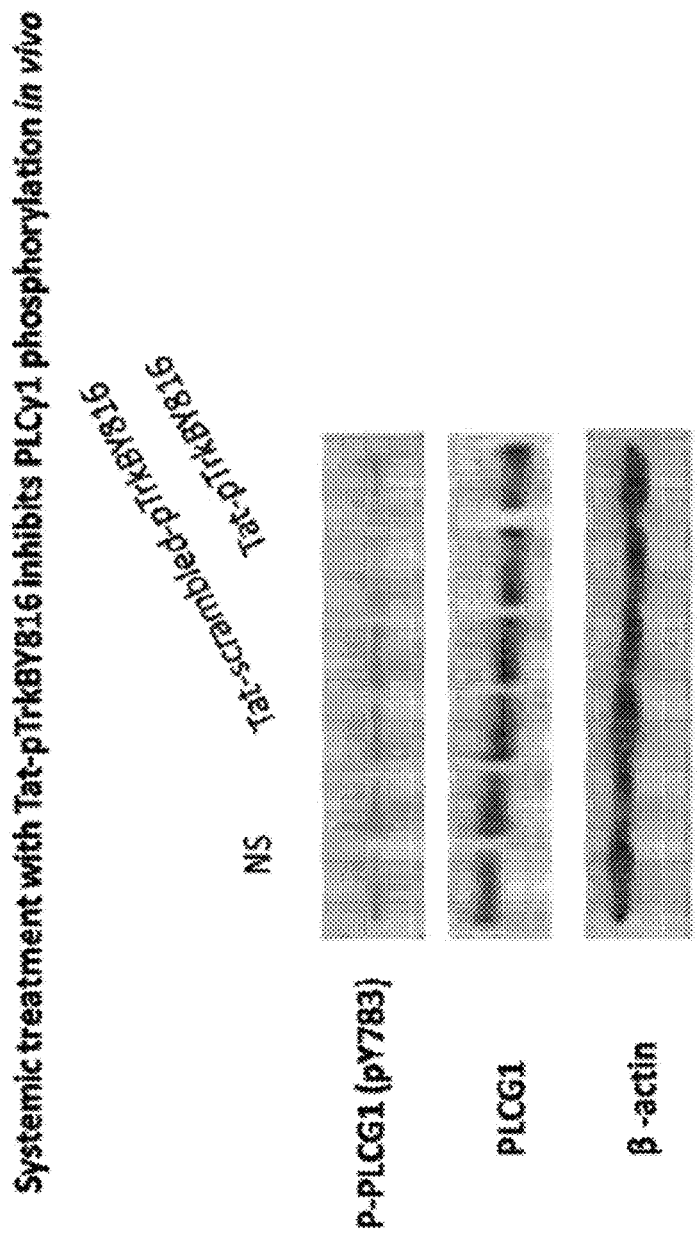

FIG. 13: Adult C57/B6 mice underwent tail vein injection of PBS or Tat-pTrkBY816 (10 mg/kg, 2 mice per group) Animals were sacrificed 3 hours later and cortex dissected and homogenate was prepared for western blotting. Top row reveals that Tat-pTrkBY816 reduced the phospho-PLCγ1 when compared to Tat-scrambled-pTrkBY816 or saline. Content of PLCγ1 (middle row) was not affected. Actin (bottom row) establishes similarity of loading and transfer among the various samples.

Figure 14:
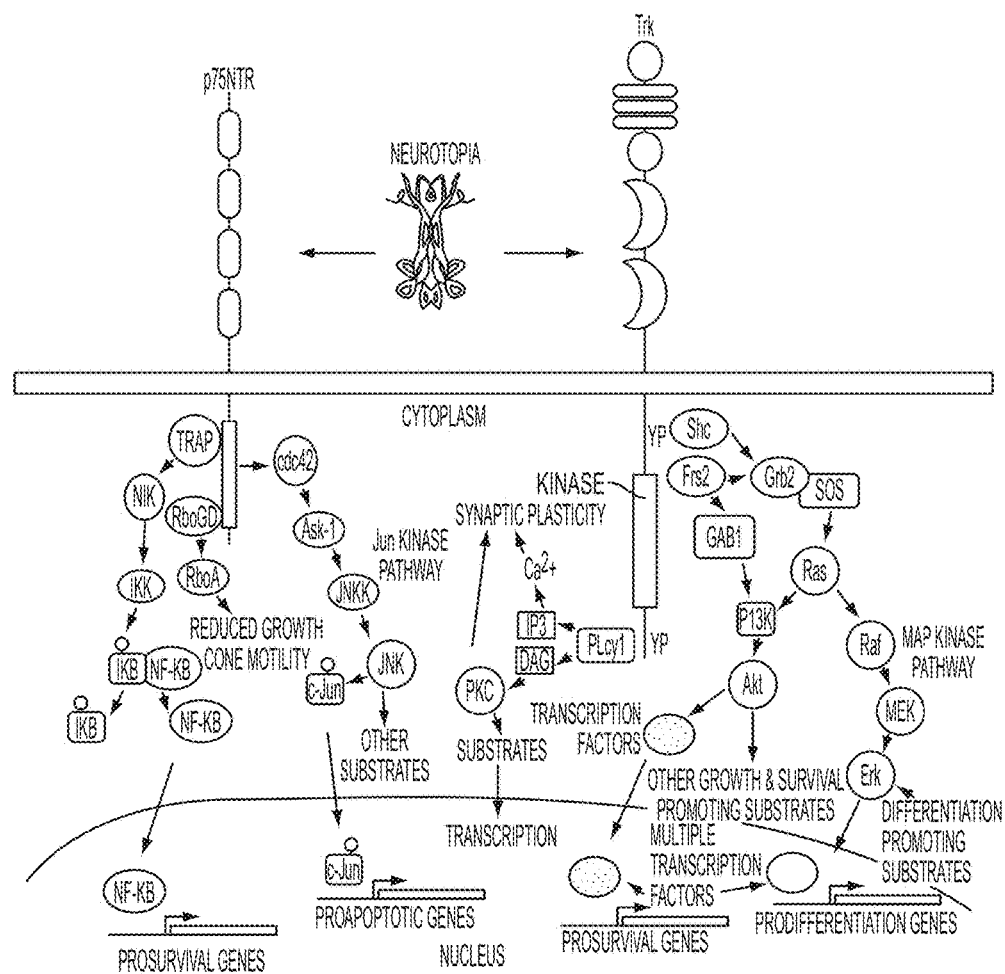

FIG. 14: A diagram showing the TrkB-PLCγ signaling pathway.

FIG. 15: Continuous limbic and tonic-clonic seizures (status epilepticus) were induced in awake, adult male WT C57BL/6 mice weighing 20-25 g by unilateral stereotaxic microinjection of 0.3 μg kainic acid (KA) in a volume of 0.2 μl PBS, pH 7.4, into the right basolateral amygdala nucleus. Seven to nine days prior to KA infusion, a guide cannula was placed in the right amygdala under pentobarbital anesthesia using the following stereotactic coordinates relative to bregma: AP, −0.94 mm; ML, −2.85 mm; and DV, −3.75 mm (AP, anterior-posterior; ML, medio-lateral; DV, dorso-ventral); additionally, a bipolar EEG recording electrode was implanted into contralateral dorsal hippocampus: AP, −2.00 mm; ML, 1.60 mm; and DV, −1.53 mm. Phospho-Tat-pTrkBY816 or Scr-phospho-Tat-pTrkBY816 was injected intravenously through tail vein before amygdala KA infusion. EEG and mice behavior were recorded by EEG recording device and video camera respectively for 45 min following infusion of KA. Design of the time course and dose response experiments are presented in top and bottom panels respectively.

Figure 16:
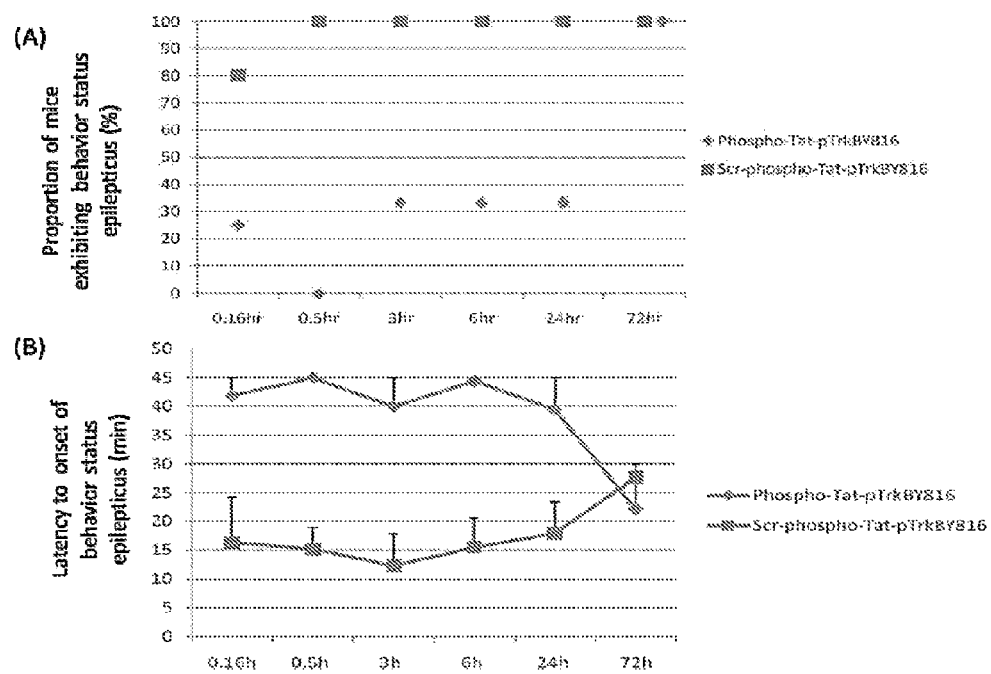

FIG. 16: Phospho-Tat-pTrkBY816 (pp) (10 mg/kg) or Scr-phospho-Tat-pTrkBY816 (sp) (10 mg/kg) was administered intravenously at the following intervals prior to infusion of KA into the right amygdala: 0.16 hr (pp, n=4; sp, n=5); 0.5 hr (pp, n=4; sp, n=2), 3 hr (pp, n=3; sp, n=3), 6 hr (pp, n=3; sp, n=3), 24 hr (pp, n=3; sp, n=3) or 72 hr (pp, n=4; sp, n=4). FIG. 16A: The proportion of animals exhibiting status epilepticus evidenced by continuous behavioral seizures (Y axis) at various intervals (X axis) is presented. All but a single animal receiving Scr-phospho-Tat-pTrkBY816 at various intervals exhibited behavioral status epilepticus. By contrast, infusion of Phospho-Tat-pTrkBY816 at multiple intervals prior to KA inhibited induction of status epilepticus; onset of inhibitory actions were evident at the earliest interval tested (0.16 hr), peaked at 0.5 hour, persisted for 24 hours, and remitted by 72 hours. FIG. 16B: The latency to onset of status epilepticus was plotted (Value 45 was assigned to the mice not developing status epilepticus within 45 min). Compared to Scr-phospho-Tat-pTrkBY816, infusion of Phospho-Tat-pTrkBY816 at multiple intervals from 0.16 hr to 24 hr prior to KA increased latency to onset of status epilepticus, and this effect was remitted by 72 hr pretreatment. Mean+SEM, * $p<0.05$, *** $p<0.001$.

Figure 17:
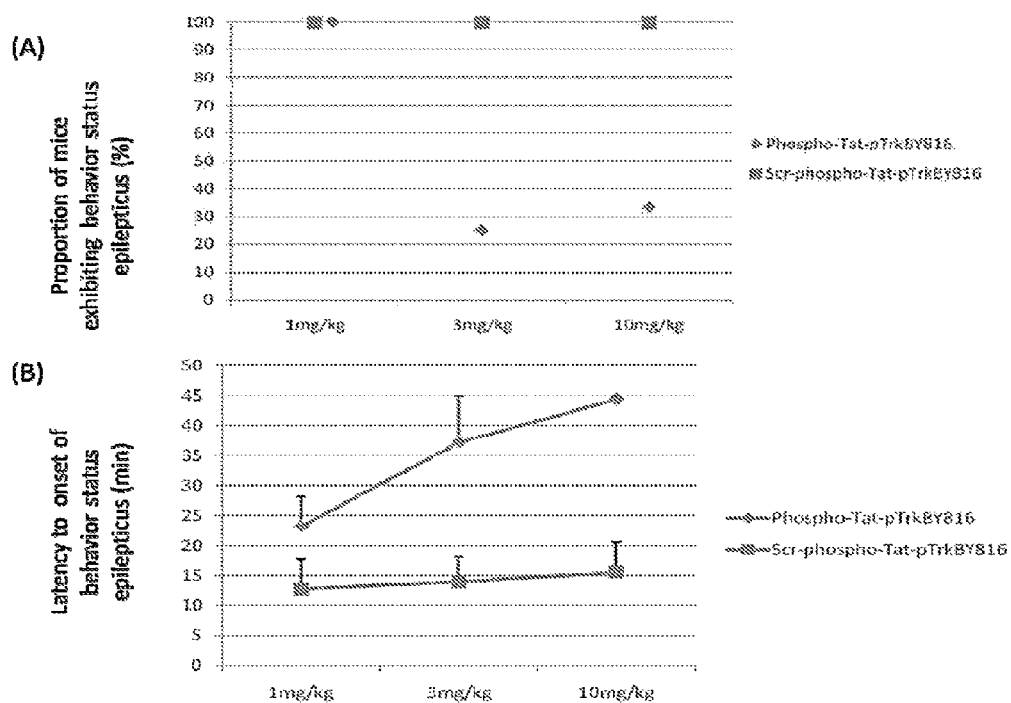

FIG. 17: Varying doses of Phospho-Tat-pTrkBY816 (pp) or Scr-phospho-Tat-pTrkBY816 (sp) (10 mg/kg) were administered intravenously at six hours prior to infusion of KA into the right amygdala: 1 mg/kg (pp, n=3; sp, n=4); 3 mg/kg (pp, n=4; sp, n=4) or 10 mg/kg (pp, n=3; sp, n=3). FIG. 17A: The proportion of animals exhibiting status epilepticus evidenced by continuous behavioral seizures (Y axis) at various doses (X axis) is presented. Whereas the control (Scr-phospho-Tat-pTrkBY816) peptide was ineffective regardless of dose, infusion of either 3 or 10 mg/kg of Phospho-Tat-pTrkBY816 inhibited induction of status epilepticus. FIG. 17B: The latency to onset of status epilepticus was plotted (Value 45 was assigned to the mice not developing status epilepticus within 45 min) Compared to Scr-phospho-Tat-pTrkBY816, infusion of Phospho-Tat-pTrkBY816, especially at 10 mg/kg significantly increased latency to onset of status epilepticus (by 3-fold). Mean+SEM, * $p<0.05$.

Figure 18:
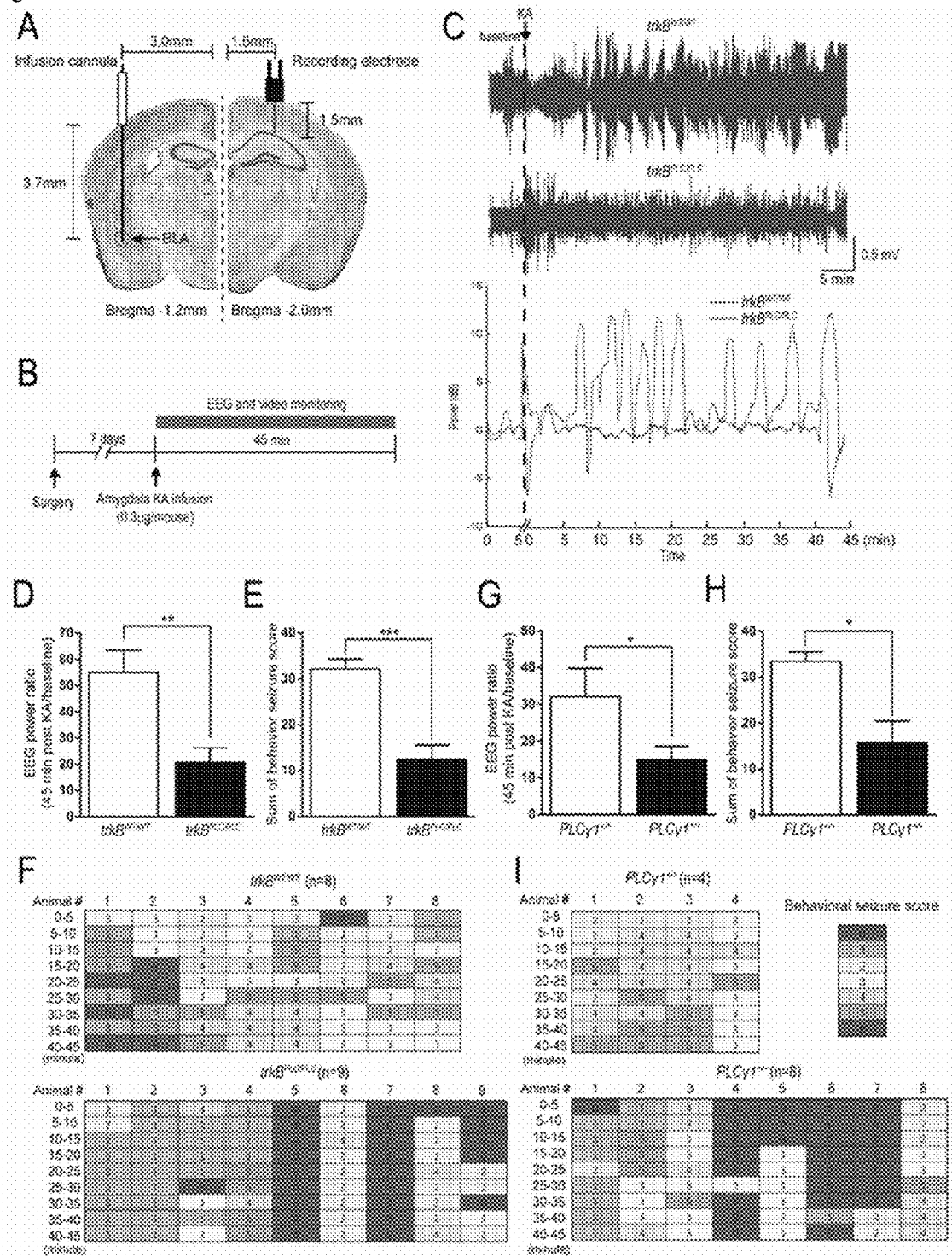
Figure 19:
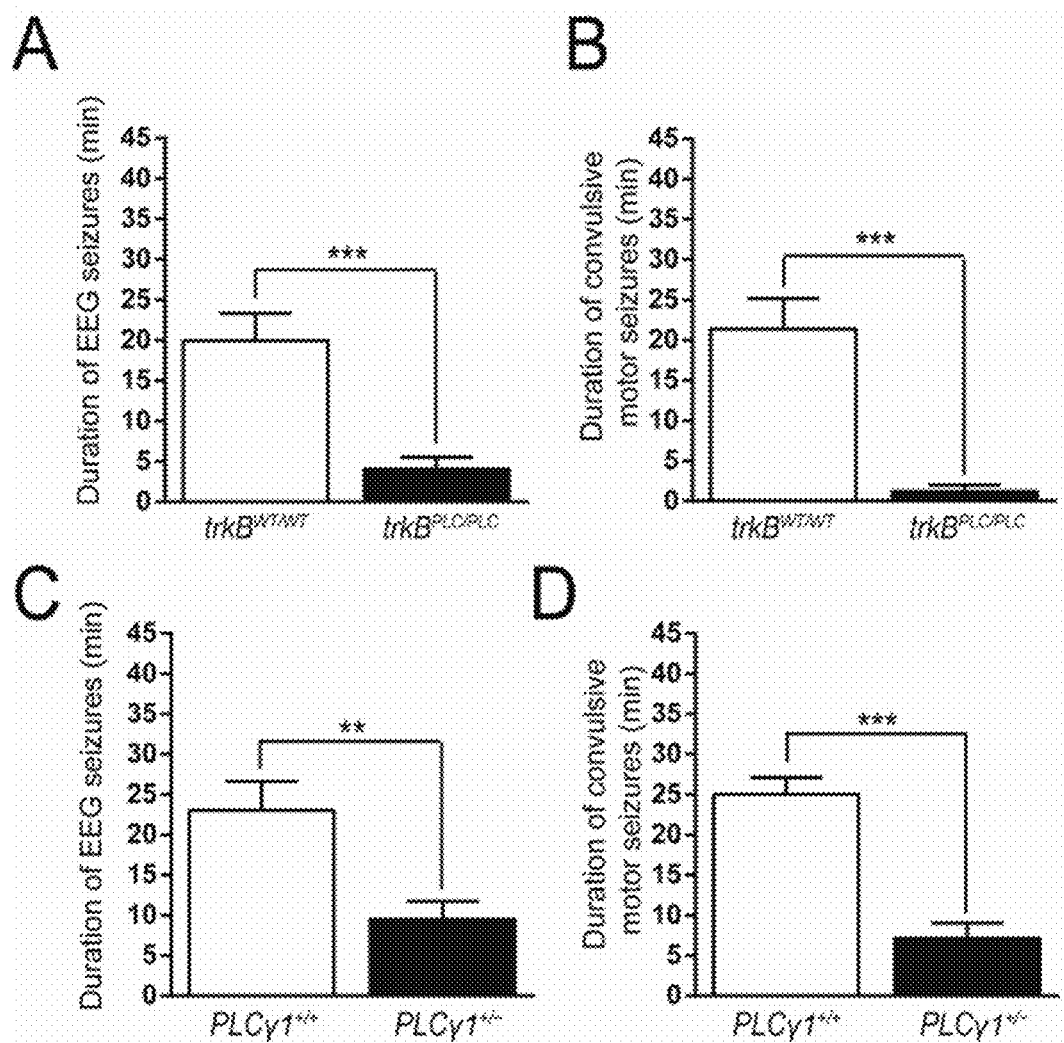

FIGS. 18A through 18I: Inhibition of TrkB-mediated PLCγ1 signaling inhibits chemoconvulsant-induced SE. FIG. 18A: Schematic of coordinates of infusion cannula and recording electrode. FIG. 18B: Schematic experiment design. Seven days after surgery, SE is evoked by infusion of 0.3 µg KA into basolateral nucleus of amygdala (BLA). EEG and video are monitored for 45 min following KA infusion. trkB$^{WT/WT}$ (n=8) or trkB$^{PLC/PLC}$ (n=9) mice (FIGS. 18 C-F) and PLC$^{+/+}$ (n=4) or PLCγ 1$^{+/-}$ (n=8) mice (G-I) were subjected to KA amygdala infusion. FIG. 18C: Representative EEG trace of trkB$^{WT/WT}$ (upper row) or trkB$^{PLC/PLC}$ (middle row) mouse during recording of 5 min prior to and 45 min after KA infusion. The representative plots of $\log_{10}$ power analyses of EEG recording adjusted to baseline power prior to KA infusion is presented immediately below, using a similar time scale. Note that compared to trkB$^{PLC/PLC}$ mouse, increases of power during 45 min in the plots of trkB$^{WT/WT}$ mouse correspond to electrographic seizure activity. EEG power normalized to 5 min baseline (FIG. 18D and FIG. 18G), total behavior seizure scores (FIG. 18E and FIG. 18H) and maximum behavior seizure score of every 5 min as shown in heatmap (FIG. 18F and FIG. 18I) were analyzed during 45 min following KA infusion. Data are presented as mean±SEM and analyzed using Student's t-test, n=4-9, $p<0.01$ and *$p<0.001$.

FIGS. 19A through 19D: Inhibition of TrkB-mediated PLCγ1 signaling inhibits chemoconvulsant-induced SE. Genetically disrupting TrkB-mediated PLCγ1 signaling inhibits SE induced by KA amygdala infusion. trkB$^{WT/WT}$ (n=8) or trkB$^{PLC/PLC}$ (n=9) mice (FIG. 19A and FIG. 19B) and PLC$^{+/+}$ (n=4) or PLCγ1$^{+/-}$ (n=8) mice (FIG. 19C and FIG. 19D) were subjected to KA amygdala infusion. Duration of EEG seizures (FIG. 19A and FIG. 19C) and duration of convulsive motor seizures (FIG. 19B and FIG. 19D) were analyzed during 45 min following KA amygdala infusion. Data are presented as mean±SEM and analyzed using Student's t-test, n=4-9, $p<0.01$ and *$p<0.001$.

Figure 20:
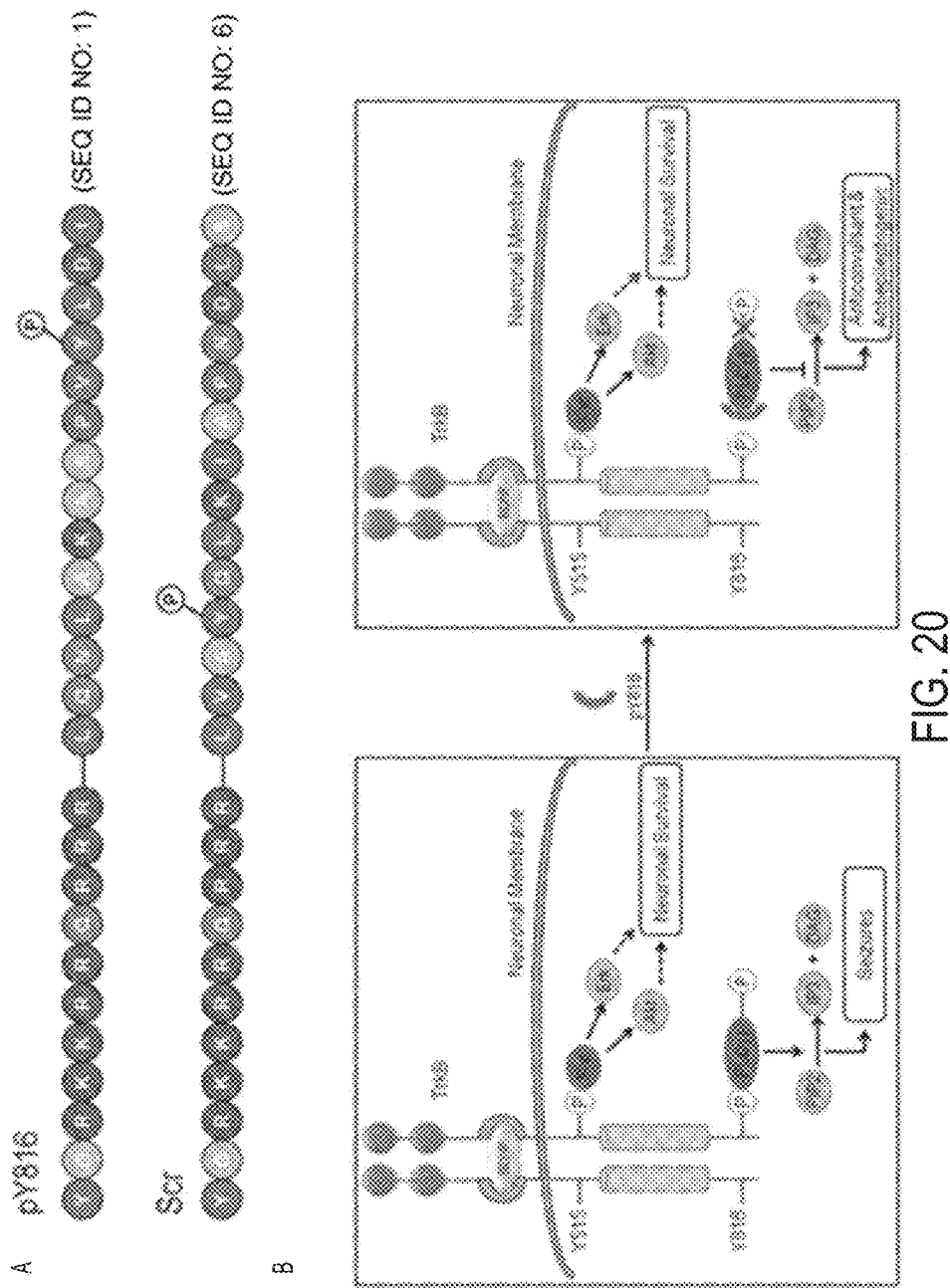

FIGS. 20A and 20B: Schematic of peptide sequence and main hypothesis. FIG. 20A: Sequence of pY816 (YGRK-KRRQRRR-LQNLAKASPVpYLDI) (SEQ ID NO: 1) and scrambled control peptide (Scr, YGRKKRRQRRR-LYApY-QLKIAPNDLS) (SEQ ID NO: 6). Tat protein transduction domain (YGRKKRRQRRR) (SEQ ID NO: 2) is conjugated to N-terminal of peptide to facilitate its the crossing blood-brain barrier and neuronal membranes. FIG. 20B: Cartoon illustrating the main hypothesis. pY816 peptide effectively and selectively inhibits TrkB-mediated PLCγ1 activation, thereby exhibiting both anticonvulsant and antiepileptogenic effects, leaving TrkB-Shc interaction intact.

Figure 21:
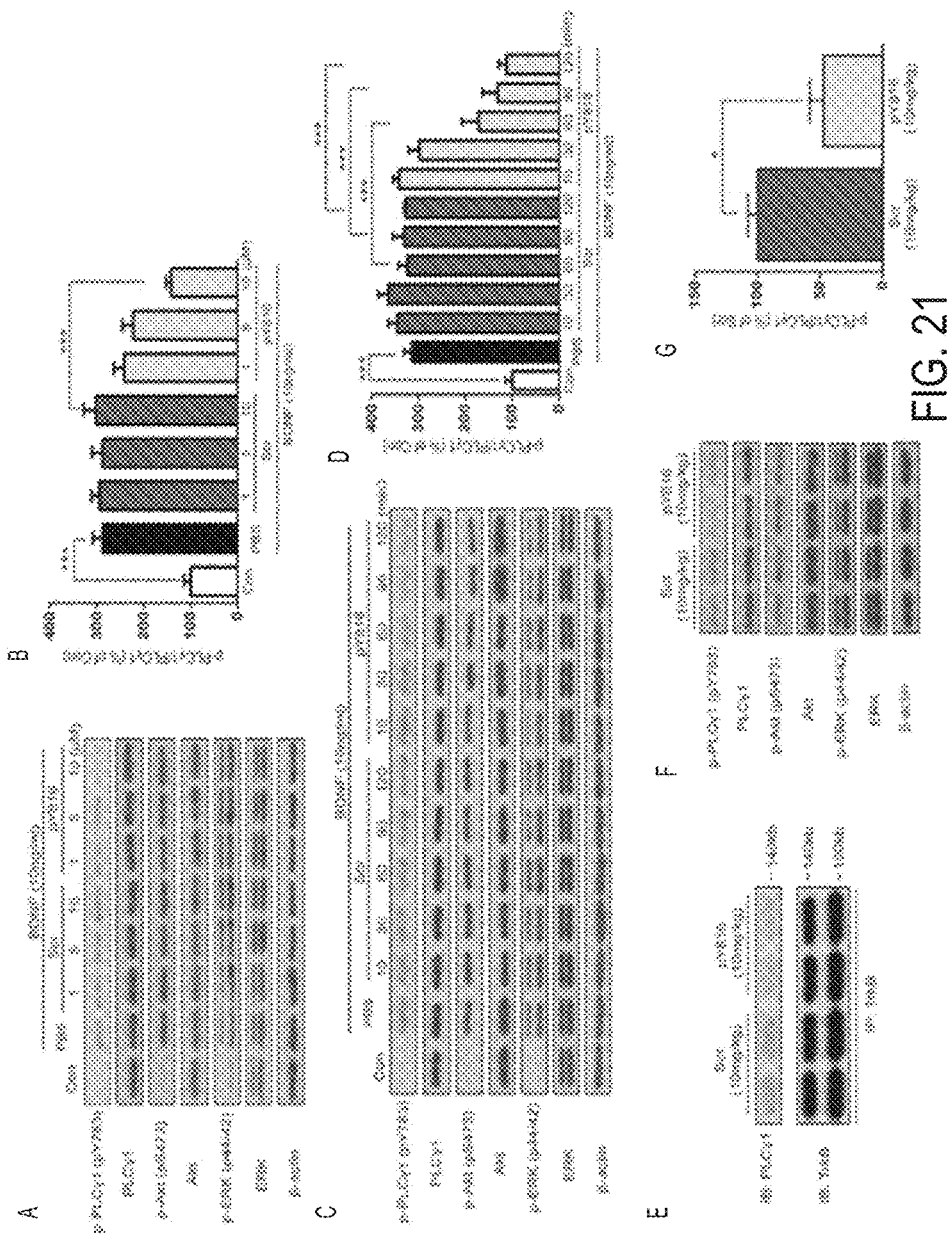

FIG. 21A through 21G: pY816 selectively inhibits PLCγ1 activation both in vitro and in vivo. For in vitro study, PBS, Scr or pY816 was preincubated with cultured neurons for 90 min at various concentrations of 1, 5 or 10 µM (FIG. 21A and FIG. 21B) or at a concentration of 10 µM for various periods of time (10, 30, 60, 90 and 120 min) (FIG. 21C and FIG. 21D) prior to addition of BDNF (100 ng/ml) for 15 min (n=3). Cells pretreated with PBS and stimulated with PBS served as controls (Con, n=3). Cells were lysed and subjected to western blotting. For in vivo study, Scr or pY816 (10 mg/kg) was injected (i.v.) into nave mice (n=4). Mice were sacrificed 3 hr after injection and hippocampal homogenates were immunoprecipitated with an anti-TrkB antibody followed by immunoblotting with anti-PLCγ1 or TrkB antibodies (FIG. 21E) or subjected to western blotting (FIG. 21F and FIG. 21G). Representative western blotting of p-PLCγ1 (pY783), PLCγ1, p-Aid (pS473), Akt, p-ERK (p44/p42), ERK and β-actin are shown (FIG. 21A, FIG. 21C and FIG. 21F) with quantification of immunoreactivity of p-PLCγ1 (pY783) to PLCγ1 ratio (FIG. 21B, FIG. 21D and FIG. 21G). Data are presented as mean±SEM and analyzed using One Way Anova with post hoc Tukey's test (FIG. 21B and FIG. 21D) and Student's t-test (FIG. 21G), n=3-4; *$p<0.05$, $p<0.01$ and *$p<0.001$.

FIG. 22A through 22F: Systemic administration of pY816 inhibits chemoconvulsant-induced SE. (FIG. 22A) Schematic of experimental design. Seven days after surgery, varying doses of pY816 or Scr peptide (1, 3 and 10 mg/kg) were injected i.v. 6 hr prior to infusion of KA into amygdala (FIG. 22B and FIG. 22C). In additional experiments, either pY816 or Scr peptide (10 mg/kg) was injected i.v. through tail vein at various intervals (15 min, 30 min, 3, 6, 24 and 72 hr) prior to infusion of KA into amygdala (FIG. 22D and FIG. 22E). EEG power normalized to 5 min baseline (FIG. 22B and FIG. 22D) and total behavior seizure scores (FIG. 22C and FIG. 22E) were analyzed during 45 min following KA infusion. No significant difference was detected among Scr-treated mice and these animals were combined (FIG. 22B and FIG. 22C, n=10; FIG. 22D and FIG. 22E, n=16) for analyses. (FIG. 22F) Maximum behavior seizure score of 5 min intervals during 45 min following KA infusion into mice treated with Scr (10 mg/kg, n=3) or pY816 (10 mg/kg, n=3) 6 hr before is shown in heatmap. Data are presented as mean±SEM and analyzed using One-way ANOVA with post hoc Tukey's test, n=3-16, *$p<0.05$, $p<0.01$ and *$p<0.001$.

Figure 23:
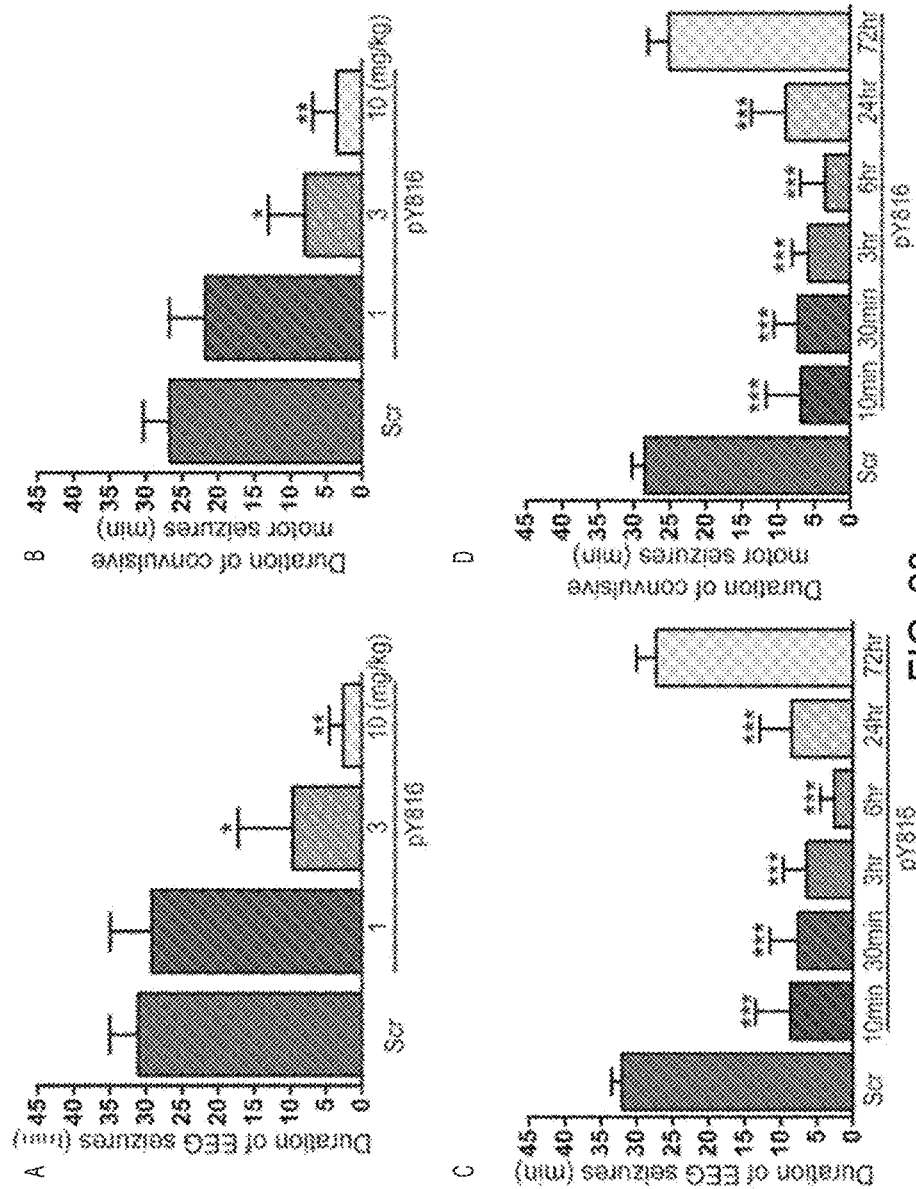

FIG. 23A through 23D: Systemic administration of pY816 inhibits chemoconvulsant-induced SE. Varying doses of pY816 or Scr peptide (1, 3 and 10 mg/kg) were injected i.v. 6 hr prior to infusion of KA into amygdala (FIG. 23A and FIG. 23B). In additional experiments, either pY816 or Scr peptide (10 mg/kg) was injected i.v. at various intervals (15 min, 30 min, 3, 6, 24 and 72 hr) prior to infusion of KA into amygdala (FIG. 23C and FIG. 23D). Duration of EEG seizures (FIG. 23A and FIG. 23C) and duration of convulsive motor seizures (FIG. 23B and FIG. 23D) were analyzed during 45 min following KA amygdala infusion. Data are presented as mean±SEM and analyzed using One-way ANOVA with post hoc Tukey's test, n=3-16, *p<0.05, p<0.01 and *p<0.001. No significant difference was found among Scr-treated mice, leading us to combine these groups for analyses (FIG. 23A and FIG. 23B, n=10; FIG. 23C and FIG. 23D, n=16).

FIG. 24A through 24F: Behavioral and EEG measures reveal similar severity of SE induced by KA prior to and following treatment with Scr or pY816. FIG. 24A: Maximum behavior seizure score of every 4 min during SE shown in heatmap. FIG. 24B: Total behavior seizure scores during SE in Scr or pY816 treated mice. FIG. 24C and FIG. 24D: EEG signal energy analyses of SE (FIG. 24C), 1 hr between treatment with diazepam and lorazepam and 1 hr post lorazepam (FIG. 23D) normalized to baseline. (FIG. 24E) and (FIG. 24F) quantification of duration (FIG. 24E) and number (FIG. 24F) of EEG seizures during 1 hr between treatment with diazepam and lorazepam and 1 hr after lorazepam. No significant (n.s.) differences of behavioral and electrographic seizures induced by infusion of KA into amygdala were found between Scr and pY816 treated mice during 40 min SE, during the 1 hr between diazepam and lorazepam, and during the 1 hr after lorazepam. Data are presented as mean±SEM and analyzed using unpaired t-test, n=8.

FIG. 25A through 25D: Treatment with pY816 following SE inhibits SE-induced activation of PLCγ1 in a dose-dependent manner. (FIG. 25A and FIG. 25B) Mice were sacrificed immediately (0 hr) and at various time points (6, 24, 48 and 72 hr) after the completion of SE induced by KA amygdala infusion. PBS infused mice served as controls. (FIG. 25C and FIG. 25D) PBS, Scr (20 mg/kg) or varying doses of pY816 (1, 10 and 20 mg/kg) were injected immediately after the completion of SE induced by KA amygdala infusion and sacrificed 6 hr later. Hippocampus ipsilateral to the infusion site was homogenized and subjected to Western blotting. Representative Western blotting of p-PLCγ1 (pY783), PLCγ1 and β-actin are shown (FIG. 25A and FIG. 25C) with quantification of immunoreactivity of p-PLCγ1 (pY783) to PLCγ1 ratio (FIG. 25B and FIG. 25D). Data are presented as mean±SEM and analyzed using One Way Anova with post hoc Tukey's test, n=3; *p<0.05, p<0.01 and *p<0.001

Figure 26:
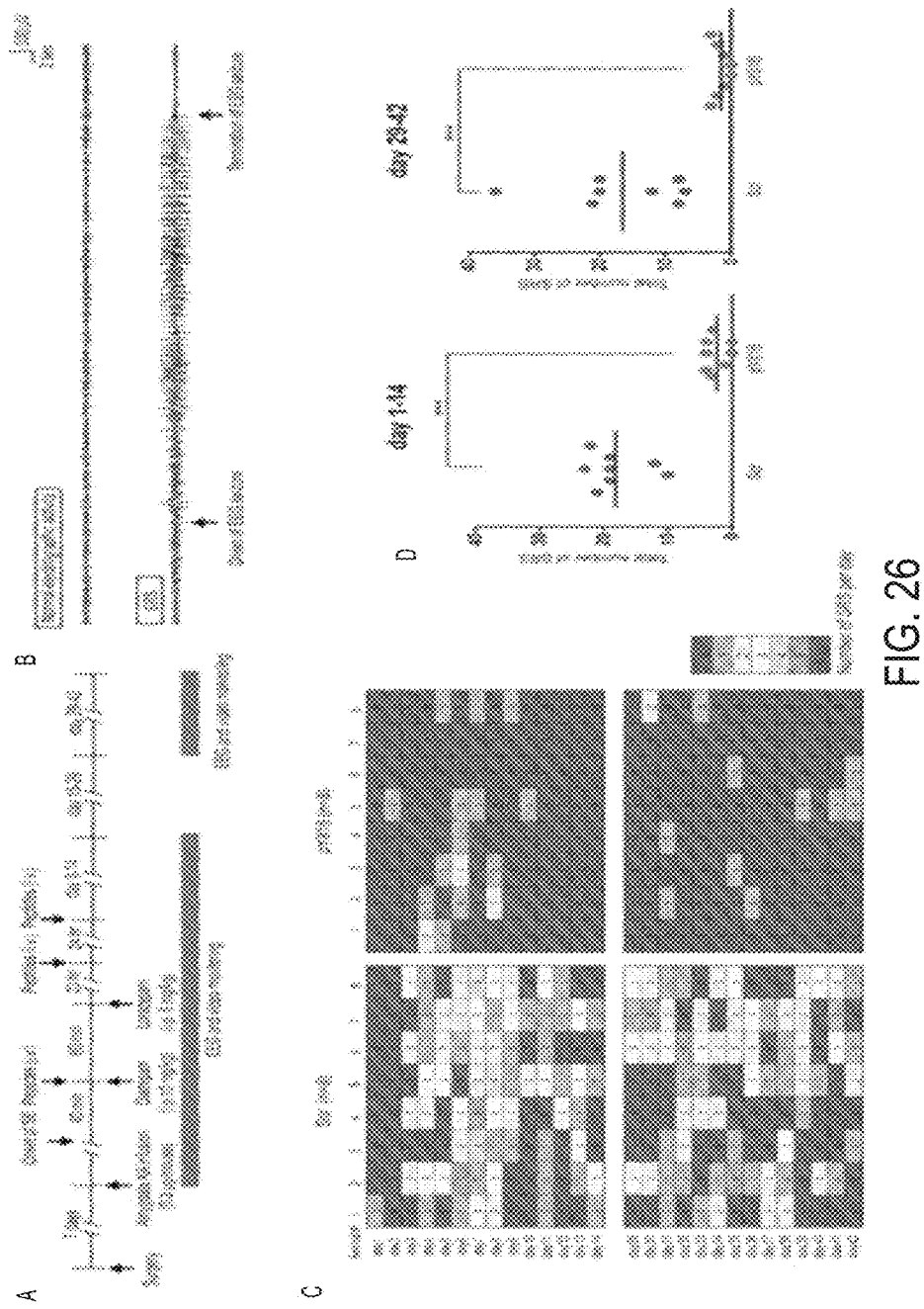

FIG. 26A through 26D: Treatment with pY816 for 3 days following SE inhibits SE-induced epilepsy assessed weeks later. FIG. 26A: Schematic of experimental design. Either Scr or pY816 (10 mg/kg) was injected (i.v.) immediately, 24 hr and 48 hr after the completion of 40 min KA-SE. Both EEG and behavior were monitored 24 hr per day during days 1-14 and again during days 29-42 after KA-SE. FIG. 26B: Representative electrographic trace of normal activity and SRSs. FIG. 26C: Heatmap presents number of SRSs detected per day during days 1-14 and days 29-42 after KA-SE treated with either Scr or pY816. FIG. 26D: Total number of SRSs during days 1-14 or days 29-42 after KA-SE treated with either Scr or PY816. Student's t-test, n=8; ***p<0.001.

Figure 27:
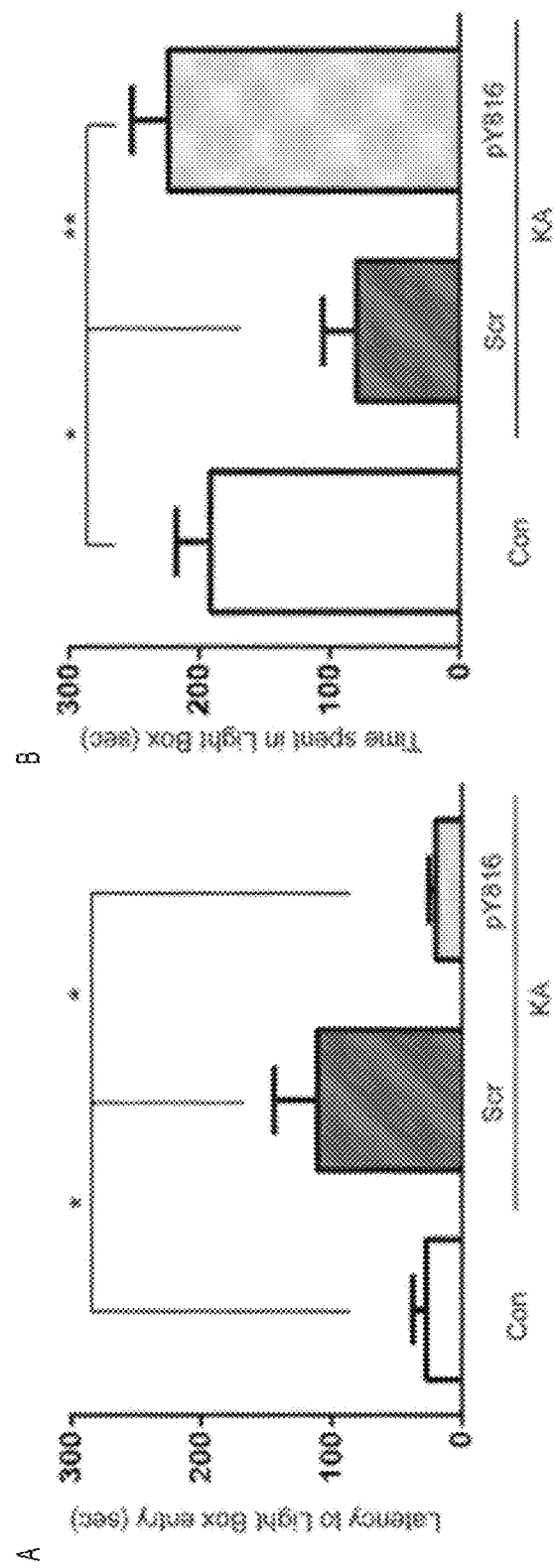

FIGS. 27A and 27B: Treatment with pY816 for 3 days following SE inhibits SE-induced anxiety-like behavior assessed 8 weeks after SE. (FIG. 27A and FIG. 27B) Mice undergoing SE and treated with Scr (n=8) or pY816 (n=8) for three days were subjected to Light and Dark box test eight weeks after SE. Mice with PBS amygdala infusion and treated with either Scr or pY816 (no difference between treatments, thereby combined for analyses) served as controls (Con, n=7). Latency to light-compartment entry (FIG. 27A) and time spent in lighted compartment (FIG. 27B) were analyzed. Data are presented as mean±SEM and analyzed using two-way ANOVA with Bonferroni corrections, *p<0.05 and **p<0.01.

Figure 28:
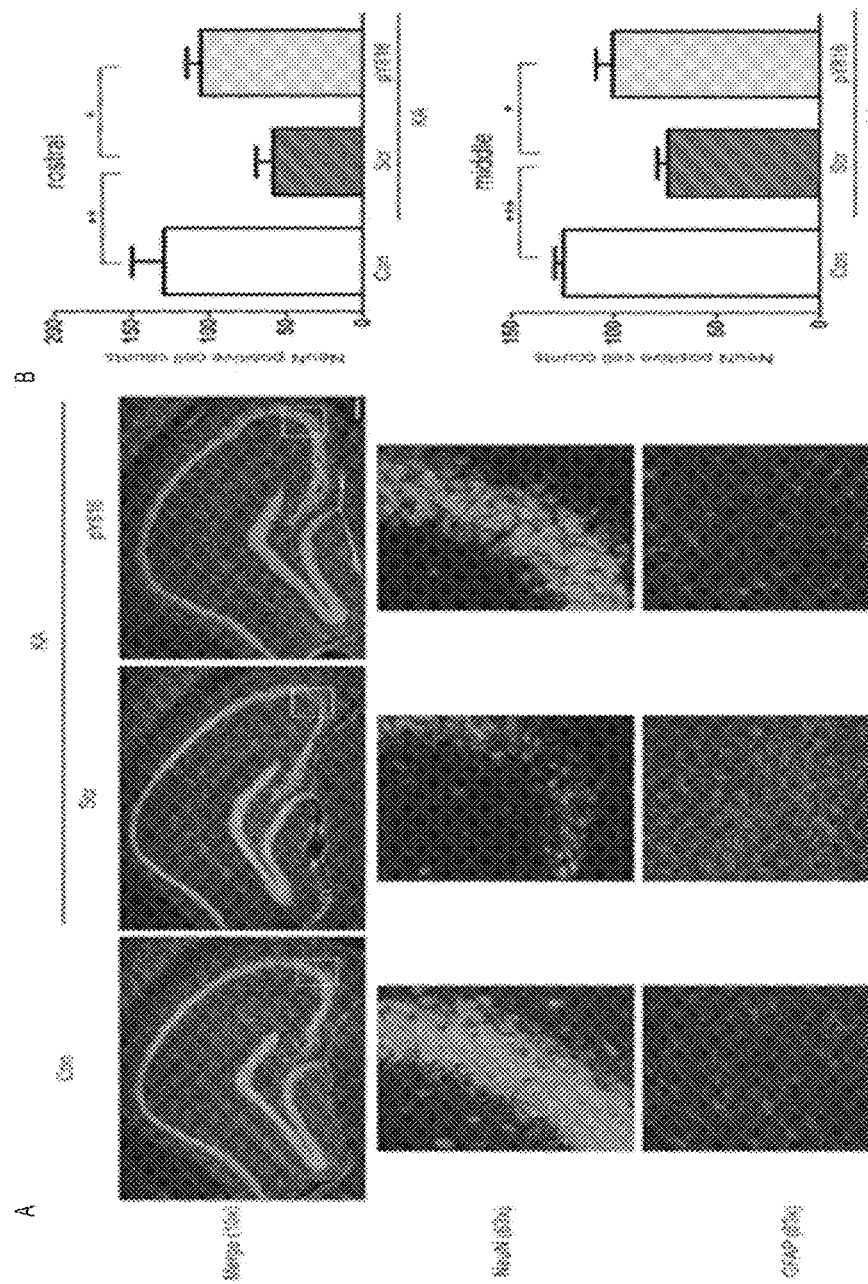

FIGS. 28A and 28B: Treatment with pY816 for 3 days following SE enhances survival of hippocampal neurons assessed 10 weeks after SE. FIG. 28A: Representative images of immunostaining of NeuN (green) and GFAP (red) in the hippocampus ipsilateral to the infusion site in PBS controls, KA-Scr treated, and KA-pY816 treated mice, scale bar=50 μM. Insets: Loss of NeuN positive cells together with enhanced GFAP immunoreactivity were evident in hippocampal area CA3b of KA-Scr treated mice (middle column); this hippocampal damage was attenuated by pY816 (right column), scale bar=20 μM. FIG. 28B: Counts of NeuN positive cells within rostral and middle levels of hippocampal area CA3b ipsilateral to infusion site of PBS controls (treated with either Scr or pY816, no difference between treatments, thereby combined for analyses, n=7), KA-Scr treated (n=8) and KA-pY816 treated (n=8) mice. Data are presented as mean±SEM and analyzed using two-way ANOVA with Bonferroni post hoc tests, *p<0.05, p<0.01 and *p<0.001.

DESCRIPTION OF EMBODIMENTS

Unless otherwise defined, all technical terms used herein have the same meaning as commonly understood by one of ordinary skill in the art to which this disclosure belongs.

The articles "a" and "an" are used herein to refer to one or to more than one (i.e. at least one) of the grammatical object of the article. By way of example, "an element" means at least one element and can include more than one element.

Definitions

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient.

As used herein, the term "kindling" or "kindling model" refers to the widely used model developed by Goddard and colleagues in the late 1960s for the development of seizures and epilepsy in which the duration and behavioral involvement of induced seizures increases after seizures are induced repeatedly (Sato, M., (2008) *Psychiatry and Clinical Neurosciences* 36(4): 440-441; Bertram, E., (2007) *Epilepsia* 48 (Supplement 2): 65-74). In such models, experimental animals are repeatedly stimulated, usually with electricity or chemicals, to induce the seizures (Bertram, E., (2007) *Epilepsia* 48 (Supplement 2): 65-74; Abel, M. S. et al. (1992) *Neuromethods: Animal Models of Neurological Disease*. Totoway, N.J.: Human Press. Pp 153-155. ISBN 0-89603-211-6). The seizure that occurs after the first such stimulation lasts a short time and is accompanied by a small amount or no behavioral effects compared with the seizures that result from repeated stimulations (Bertram, E., (2007) *Epilepsia* 48 (Supplement 2): 65-74). With further seizures, the accompanying behavior intensifies, for example, progressing from a freezing in early stimulations to convulsions in later ones (Morimoto, K. et al., (2004) *Prog. Neurobiol.* 73(1): 1-60). The lengthening of duration and intensification of behavioral accompaniment eventually reaches a plateau after repeated stimulations (Bertram, E., (2007) *Epilepsia* 48 (Supplement 2): 65-74).

As used herein, the term "disorder of the nervous system" refers to a pathological condition relating to the brain and/or nervous system. Preferably, the neurological disorder involves the TrkB/PLCγ1 signaling pathway. Such conditions include, but are not limited to, stroke, anxiety, epilepsy, head trauma, migraine, pain, which includes chronic and acute neuropathic pain, schizophrenia, depression, obsessive-compulsive disorder, affective disorders, such as mania (e.g., bipolar disorder, depression and other mood disorders), severe anxiety disorders, such as post-traumatic stress disorder, and addiction. As used herein, the terms "disorder(s) of the nervous system," "neurologic disease(s)," "psychiatric disorders," "neuropsychiatric disorders," and "neurologic disorder(s)" can be used interchangeably.

As used herein, the term "epilepsy" refers to any of the various neurological disorders marked by abnormal electrical discharges in the brain and often manifested by sudden brief episodes of altered or diminished consciousness, involuntary movements, or convulsions. There are over 40 different types of epilepsy, all of which are within the scope of the present disclosure. These include, but are not limited to: Absence seizures (petit mal), atonic seizures, benign Rolandic epilepsy, childhood absence, clonic seizures, complex partial seizures, frontal lobe epilepsy, Febrile seizures, Infantile spasms, Juvenile Myoclonic Epilepsy, Juvenile Absence Epilepsy, Lennox-Gastaut syndrome, Landau-Kleffner Syndrome, myoclonic seizures, Mitochondrial Disorders, Progressive Myoclonic Epilepsies, Psychogenic Seizures, Reflex Epilepsy, Rasmussen's Syndrome, Simple Partial Seizures and Epilepsy, Secondarily Generalized Seizures, Temporal Lobe Epilepsy, Toni-clonic seizures (gran mal), Tonic seizures, Psychomotor Seizures, Complex Partial Seizures and Epilepsy, Limbic Epilepsy, Partial-Onset Seizures, generalized-onset seizures, Status Epilepticus, Abdominal Epilepsy, Akinetic Seizures, Auto-nomic seizures, Massive Bilateral Myoclonus, Catamenial Epilepsy, Drop seizures, Emotional seizures, Focal seizures, Gelastic seizures, Jacksonian March, Lafora Disease, Motor seizures, Multifocal seizures, Neonatal seizures, Nocturnal seizures, Photosensitive seizure, Pseudo seizures, Sensory seizures, Subtle seizures, Sylvan Seizures, Withdrawal seizures, Visual Reflex Seizures amongst others. The most widespread classification of the epilepsies divides epilepsy syndromes by location or distribution of seizures (as revealed by the appearance of the seizures and by EEG) and by cause. Syndromes are divided into localization-related epilepsies, generalized epilepsies, or epilepsies of unknown localization.

As used herein, the term "pain" refers to the basic bodily sensation induced by a noxious stimulus, received by naked nerve endings, characterized by physical discomfort (e.g., pricking, throbbing, aching, etc.) and typically leading to an evasive action by the individual. As used herein, the term pain also includes chronic and acute neuropathic pain. The terms "neuropathic pain" or "neurogenic pain" can be used interchangeable and refer to pain that arises from direct stimulation of nervous tissue itself, central or peripheral and can persist in the absence of stimulus. The sensations that characterize neuropathic pain vary and are often multiple and include burning, gnawing, aching, and shooting. (See Rooper and Brown, (2005) *Adams and Victor's Principles of Neurology*, 8th ed., NY, McGraw-Hill). These damaged nerve fibers send incorrect signals to other pain centers. The impact of nerve fiber injury includes a change in nerve function both at the site of injury and areas around the injury. Chronic neuropathic pain often seems to have no obvious cause, however, some common causes may include, but are not limited to, alcoholism, amputation, back, leg and hip problems, chemotherapy, diabetes, facial nerve problems, HIV infection or AIDS, multiple sclerosis, shingles, and spine surgery. For example, one example of neuropathic pain is phantom limb syndrome, which occurs when an arm or leg has been removed because of illness or injury, but the brain still gets pain messages from the nerves that originally carried impulses from the missing limb.

As used herein, the term "addiction" refers to the compulsive need for and use of a habit forming substance, such as heroin, cocaine, nicotine, alcohol, etc., that is characterized by tolerance and by well-defined physiological symptoms upon withdrawal. Broadly, the term "addiction" refers to the persistent compulsive use of any substance known by the user to be harmful.

As used herein, the term "interfering molecule" refers to any molecule that is capable of disrupting an intracellular signaling pathway. In preferred embodiments, the "interfering molecule" is capable of disrupting the TrkB/PLCγ signaling pathway. In certain embodiments, the interfering molecule inhibits TrkB-mediated PLCγ activation and/or phosphorylation. Examples of suitable interfering molecules include, but are not limited to, small molecules, antibodies, antisense RNAs, cDNAs, dominant-negative forms of molecules such as TrkB or PLCγ, peptides, phosphorpeptides, amino acids, protein kinase inhibitors, combinations thereof, and the like.

In certain embodiments, the interfering molecule may be a small molecule. In such embodiments, the small molecules generally have a molecular weight of approximately 450 Da or less and may include, but are not limited to amino acids, monosaccharides, oligosaccharides, nucleotides, olionucleotides, salt compositions, and their derivatives. In preferred embodiments, the small molecules are capable of crossing the blood brain barrier.

In a preferred embodiment, the interfering molecule is a protein, peptide fragment, phosphopeptide, or amino acids. In one embodiment, the peptides generally have a molecular weight of 2.5 kDa. Accordingly, the present disclosure further provides polypeptides having one or more residues from the PLCγ1 binding site of TrkB, and polynucleotides encoding such polypeptides. In certain embodiments, a molecule is a polypeptide which corresponds to amino acids 806-819 of the human TrkB peptide. In preferred embodiments, the interfering molecule comprises the amino acid sequence LQNLAKASPVYLDI (SEQ ID NO:4). More preferably, the Y816 is phosphorylated. In preferred embodiments, the proteins or peptide fragments are capable of crossing the blood brain barrier.

As used herein, the terms "uncouples" and/or "uncoupling" refer to any means of disrupting the physical interaction of TrkB with its signaling effector. In a preferred embodiment the signaling effector is PLCγ1. In one embodiment, uncoupling can include but is not limited to the inhibition of TrkB interaction with its signaling effector, including PLCγ1, via an interfering molecule. In a preferred embodiment the interfering molecule is a protein, peptide fragment, phosphopeptide, or amino acids, such as for example, the peptide of SEQ ID. NO: 1.

As used herein, the phrase "inhibiting the physical interaction" refers to disruption of the physical association of a receptor tyrosine kinase (RTK) with a signaling effector. In a preferred embodiment the receptor tyrosine kinase is TrkB and its signaling effector is PLCγ1. An example of inhibiting the physical interaction of TrkB with PLCγ1 is disclosed herein. Wherein an interfering molecule (e.g., phosphopeptide pY816), is administered to cultured cortical neurons or adult mouse brain, the phosphopeptide disrupts the co-immunoprecipitation of TrkB and PLCγ1. (See FIG. 21). This disruption of the association of TrkB and PLCγ1 is one example of "inhibiting the physical interaction" of an RTK and its signaling effector.

As used herein, the term "signaling effector" refers to a protein that directly binds to the tyrosine-phosphorylated intracellular domain of a receptor tyrosine kinase and promotes activation of signaling pathways. As one example, PLCγ1 is a signaling effector of TrkB. Another signaling effector of TrkB is the Shc protein. As another example, both PLCγ1 and Shc are signaling effectors of other receptor tyrosine kinases, including the epidermal growth factor receptor.

The present application is also directed to nucleic acid molecules comprising, or alternatively, consisting of, a polynucleotide sequence at least 90%, 92%, 95%, 96%, 97%, 98%, or 99% identical to the polynucleotide sequence encoding the PLCγ1 binding site of TrkB polypeptide described above. The present invention also encompasses the above polynucleotide sequences fused to a heterologous polynucleotide sequence.

In certain embodiments, the polypeptide is fused with peptide sequence capable of allowing the polypeptide to cross the blood brain barrier and limit protein to protein interactions. Preferably, the peptide sequence comprises the viral TAT gene, or portions thereof. In preferred embodiments, the TAT sequence comprises YGRKKRRQRRR (SEQ ID NO:2). Accordingly, in a preferred embodiment, the polypeptide, herein referred to as a phosphopeptide, comprises the following sequence YGRKKRRQRRRLQNLAKASPVpYLDI (SEQ ID NO:3), wherein Y816 is phosphorylated (designated by p) and termed Phospho-Tat-pTrkBY816.

The present disclosure is also directed to nucleic acid molecules comprising, or alternatively, consisting of, a polynucleotide sequence at least 90%, 92%, 95%, 96%, 97%, 98%, or 99% identical to the polynucleotide sequence encoding the phosphor-Tat-pTrkBY816 polypeptide described above. The present disclosure also encompasses the above polynucleotide sequence fused to a heterologous polynucleotide sequence. The invention also provides polypeptides having one or more amino acids deleted, added, or substituted for from each of or both the amino and the carboxyl termini of Phospho-Tat-pTrkBY816. Polynucleotides encoding these polypeptides are also encompassed by the invention.

Also included are a nucleotide sequence encoding a polypeptide consisting of a portion of the complete TrkB amino acid sequence encoded by the cDNA clones contained in ATCC™ Deposit Nos. 37957, 37957D, 63055, 85442 and 85608.

As indicated, nucleic acid molecules of the present invention may be in the form of RNA, such as mRNA, are in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

The terms "neurotrophin" and "neurotrophic factor" and their grammatical variants are used interchangeably, and refer to a family of polypeptides comprising nerve growth factor (NGF) and sequentially related homologs. NGF, brain-derived neurotrophic factor (BDNF), neurotrophin-3 (NT-3), and neurotrophins-4 and -5 (NT-4/5) have so far been identified as members of this family.

The terms "neurotrophin" and "neurotrophic factor" include native neurotrophins of any (human or non-human) animal species, and their functional derivatives, whether purified from a native source, prepared by methods of recombinant DNA technology, or chemical synthesis, or any combination of these or other methods. "Native" or "native sequence" neurotrophic factors or neurotrophins have the amino acid sequence of a neurotrophin occurring in nature in any human or non-human animal species, including naturally-occurring truncated and variant forms, and naturally-occurring allelic variants.

The terms "trk", "trk polypeptide", "trk receptor" and their grammatical variants are used interchangeably and refer to polypeptides of the tropomyosin-related kinase family, which are capable of binding at least one native neurotrophic factor. Currently identified members of this family are trkA (p140$^{trKA}$), trkB, and trkC, but the definition specifically includes polypeptides that might be identified in the future as members of this receptor family. The terms "trk", "trk polypeptide" and "trk receptor", with or without an affixed capital letter (e.g., A, B or C) designating specific members within this family, specifically include "native" or "native sequence" receptors (wherein these terms are used interchangeably) from any animal species (e.g. human, murine, rabbit, porcine, equine, etc.), including full length receptors, their truncated and variant forms, such as those arising by alternate splicing and/or insertion, and naturally-occurring allelic variants, as well as functional derivatives of such receptors. Thus, a "native" or "native sequence" human trkB polypeptide has the amino acid sequence of any form of a trkB receptor as occurring in the human, including full length native human trkB, truncated, tyrosine kinase (TK) domain-deleted (spliced) forms of full length native human trkB, and insertion variants of full length or truncated native human trkB, wherein the insert is within the TK domain or within the extracellular domain, and any further naturally-occurring human trkB polypeptides that might be identified in the future.

As used herein, the term "TrkB-PLCγ signaling pathway" refers to the neurotrophin signaling pathway involving TrkB and PLCγ1. As shown in FIG. 14, upon binding of BDNF to TrkB receptors, TrkB receptors undergo dimerization and increased intrinsic kinase activity. TrkB activation induces tyrosine autophosphorylation within the intracellular domain, including Y515 and Y816, providing docking sites for signaling proteins Shc (thereby activating the Ras/MAP kinase signaling pathway) and PLCγ1 (thereby activating the PLCγ signaling pathway, the effects of which include increased intracellular calcium and enhanced PKC signaling), respectively. Therefore, it is within the scope of the present disclosure that an interfering molecule may target one or more of these tyrosine phosphorylation sites on the TrkB receptor, thereby disrupting signal transduction. In a preferred embodiment, such interfering molecule will be "removable", thereby not permanently disrupting the signal transduction pathway. The terms "PLCγ" and "PLCγ1" are used interchangeably herein.

"Fragments" comprise regions within the sequence of a mature native neurotrophic factor or trk receptor. Preferred fragments of trk receptors include amino acid sequences within the intracellular/cytoplasmic domain. The term "derivative" is used to define amino acid sequence and covalent modifications of a native polypeptide, whereas the term "variant" refers to amino acid sequence and phosphorylation or other variants within this definition. "Biological property" in the context of the definition of "functional derivatives" is defined as either 1) immunological cross-reactivity with at least one epitope of a native polypeptide (e.g. neurotrophin or trk receptor), or 2) the possession of at least one adhesive, regulatory or effector function qualitatively in common with a native polypeptides (e.g. neurotrophin or trk receptor).

"Isolated" nucleic acid or polypeptide in the context of the present disclosure is a nucleic acid or polypeptide that is identified and separated from contaminant nucleic acids or polypeptides present in the animal or human source of the nucleic acid or polypeptide. The nucleic acid or polypeptide may be labeled for diagnostic or probe purposes, using a label as described and defined further below in discussion of diagnostic assays.

In general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native amino acid sequence Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

The term "glycosylation variant" is used to refer to a polypeptide having a glycosylation profile different from that of a corresponding native polypeptide. Glycosylation of polypeptides is typically either N-linked or O-linked. N-linked refers to the attachment of the carbohydrate moiety to the side of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be involved in O-linked glycosylation. Any difference in the location and/or nature of the carbohydrate moieties present in a variant or fragment as compared to its native counterpart is within the scope herein.

"Covalent derivatives" include modifications of a native polypeptide or a fragment thereof with an organic proteinaceous or non-proteinaceous derivatizing agent, and post-translational modifications. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the trk receptor polypeptides of the present disclosure. Other post-translational modifications include hydroxylation of proline and lysine, phosphorylation of hydroxyl groups of seryl, tyrosine or threonyl residues, methylation of the .alpha.-amino groups of lysine, arginine, and histidine side chains (T. E. Creighton, (1983) *Proteins: Structure and Molecular Properties*, W.H. Freeman & Co., San Francisco, pp. 79-86).

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the polypeptide chain. The DNA sequence thus codes for the amino acid sequence.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancer.

Nucleic acid is "operably linked" when it is placed into a functional relationship with another nucleic acid sequence. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

In the context of the present disclosure the expressions "cell", "cell line", and "cell culture" are used interchangeably, and all such designations include progeny. Thus, the words "transformants" and "transformed (host) cells"

include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

An "exogenous" element is defined herein to mean nucleic acid sequence that is foreign to the cell, or homologous to the cell but in a position within the host cell nucleic acid in which the element is ordinarily not found.

Antibodies (Abs) and immunoglobulins (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one and ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., (1985) *J. Mol. Biol.* 186, 651-663; Novotny and Haber, (1985) *Proc. Natl. Acad. Sci. USA* 82, 4592-4596).

The variability is not evenly distributed through the variable regions of antibodies. It is concentrated in three segments called complementarity determining regions (CDRs) or hypervariable regions both in the light chain and the heavy chain variable regions. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies [see, e.g., Kabat, E. A. et al., (1987) *Sequences of Proteins of Immunological Interest* National Institute of Health, Bethesda, Md.). The constant domains are not involved directly in binding an antibody to an antigen, but exhibit various effector functions, such as participation of the antibody in antibody-dependent cellular toxicity.

Papain digestion of antibodies produces two identical antigen binding fragments, called Fab fragments, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$-$V_L$ dimer Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_{H\,1}$) of the heavy chain. Fab' fragments differ from Fab fragments by the addition of a few residues at the carboxy terminus of the heavy chain $C_{H\,1}$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other, chemical couplings of antibody fragments are also known.

The light chains of antibodies (immunoglobulins) from any vertebrate species can be assigned to one of two clearly distinct types, called kappa and lambda (λ) based on the amino acid sequences of their constant domains.

Depending on the amino acid sequence of the constant region of their heavy chains, immunoglobulins can be assigned to different classes. There are five major classes of immunoglobulins: IgA, IgD, IgE, IgG and IgM, and several of these may be further divided into subclasses (isotypes), e.g. IgG-1, IgG-2, IgG-3, and IgG-4; IgA-1 and IgA-2. The heavy chain constant regions that correspond to the different classes of immunoglobulins are called α, δ, ε, γ, and μ respectively. The subunit structures and three-dimensional configurations of different classes of immunoglobulins are well known. IgA-1 and IgA-2 are monomeric subclasses of IgA, which usually is in the form of dimers or larger polymers. Immunocytes in the gut produce mainly polymeric IgA (also referred to poly-IgA including dimers and higher polymers). Such poly-IgA contains a disulfide-linked polypeptide called the "joining" or "J" chain, and can be transported through the glandular epithelium together with the J-containing polymeric IgM (poly-IgM), comprising five subunits.

The term "antibody" is used in the broadest sense and specifically covers single anti-trk and/or anti-PLCγ monoclonal and polyclonal antibodies (including agonist and antagonist antibodies) and anti-trk and/or anti-PLCγ antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins.

The monoclonal antibodies herein include hybrid and recombinant antibodies produced by splicing a variable (including hypervariable) domain of an anti-trk and/or anti-PLCγ antibody with a constant domain (e.g. "humanized"

antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. [See, e.g. Cabilly, et al., U.S. Pat. No. 4,816,567; Mage & Lamoyi, (1987) *Monoclonal Antibody Production Techniques and Applications*, pp. 79-97 (Marcel Dekker, Inc., New York).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by generating hybridomas which are well known to those skilled in the art.

"Humanized" forms of non-human (e.g. murine) antibodies are specific chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

The term "administering" or "administered" as used herein is meant to include both parenteral and/or oral administration, all of which are described in more detail in the "pharmaceutical compositions" section below. By "parenteral" is meant intravenous, subcutaneous or intramuscular administration. In the methods of the subject disclosure, the interfering molecules of the present disclosure may be administered alone, simultaneously with one or more other interfering molecule, or the compounds may be administered sequentially, in either order. It will be appreciated that the actual preferred method and order of administration will vary according to, inter alia, the particular preparation of interfering molecules being utilized, the particular formulation(s) of the one or more other interfering molecules being utilized. The optimal method and order of administration of the compounds of the disclosure for a given set of conditions can be ascertained by those skilled in the art using conventional techniques and in view of the information set out herein. The term "administering" or "administered" also refers to oral sublingual, buccal, transnasal, transdermal, rectal, intramuscular, intravenous, intraventricular, intrathecal, and subcutaneous routes. In accordance with good clinical practice, it is preferred to administer the instant compounds at a concentration level which will produce effective beneficial effects without causing any harmful or untoward side effects.

According to the present disclosure, a "therapeutically effective amount" of a pharmaceutical composition is an amount which is sufficient for the desired pharmacological effect.

As used herein, the term "ameliorate" refers to the ability to make better, or more tolerable, or reduce, a neurological, psychiatric or neuropsychatric disorder, and may encompass "limiting progression," which refers to the lessening or limiting of the scope or severity of the neurological or psychiatric condition. The term "prevent" refers to the ability to keep a neurological, psychiatric or neuropsychatric disorder from developing, happening or existing. The term "treating" refers to the caring for, or dealing with, a neurological, psychiatric or neuropsychiatric condition either medically or surgically, and can include "ameliorating" and/or "limiting progression." Also within the scope of the term "treating" is the acting upon a subject with a neurological or psychiatric disorder with some agent, such as an interfering molecule, to amelioriate, improve, alter, or reduce the neurological, psychiatric or neuropsychiatric condition.

The terms "suppress", "inhibit", "block", "decrease", "attenuate," "downregulated" or the like, denote quantitative differences between two states, preferably referring to at least statistically significant differences between the two states.

According to the present disclosure, it has been discovered that the onset and progression of several neurological disorders, such as epilepsy, involve the TrkB-PLCγ signaling pathway. The TrkB-mediated activation of PLCγ1 is important for the molecular and cellular activation of downstream events, such as the long term potentiation of the mossy fiber-CA3 pyramid synapse and reduced expression of the K—Cl cotransporter, KCC2, that lead to the development or progression of epilepsy. Furthermore, inhibition of the TrkB kinase activity as well as abolition of the TrkB-PLCγ1 binding by mutating one key tyrosine site of TrkB significantly reduce the development and/or progression of epilepsy. Therefore, methods, compounds, and strategies directed to the interference of the TrkB-PLCγ signaling pathway will prevent, slow, or reduce the induction and/or progression of neurological disorders such as epilepsy. Additionally, the inventive methods, compounds, and strategies will impact signaling pathways contributing to neuropathic pain and thus will prevent, slow, or reduce the induction and/or progression of pain. More specifically, the present disclosure provides compositions and methods for uncoupling a receptor tyrosine kinase (RTK) from a signaling effector, the method comprising inhibiting the physical interaction of an RTK with its signaling effector.

According to one embodiment of the present disclosure, an interfering molecule is used to block or inhibit TrkB-mediated activation of PLCγ1. In certain embodiments, the interfering molecule is selected from the group consisting of proteins, polypeptides, phosphopeptides, peptide fragments, amino acids, antibodies, antisense or small interfering RNA molecules, small molecules, dominant-negative forms of PLCγ and combinations thereof. In certain embodiments, the interfering molecule is a small peptide. In preferred embodiments, the small peptide comprises the amino acid sequence YGRKKRRQRRRLQNLAKASPVpYLDI (SEQ ID NO: 3), wherein Y816 is phosphorylated (designated by p).

Pharmaceutical Compositions

As used herein, the term "pharmaceutical composition" means physically discrete coherent portions suitable for medical administration. The term "dosage unit form" or "unit dosage" means physically discrete coherent units suitable for medical administration, each containing a daily dose or a multiple (up to four times) or a sub-multiple (down to a fortieth) of a daily dose of the active compound in association with a carrier and/or enclosed within an envelope. Whether the composition contains a daily dose, or for example, a half, a third or a quarter of a daily dose, will depend on whether the pharmaceutical composition is to be administered once or, for example, twice, three times or four times a day, respectively.

The phosphopeptides of the present disclosure may be administered to the subject as a composition which comprises a pharmaceutically effective amount of phosphopeptide and an acceptable carrier and/or excipients. A pharmaceutically acceptable carrier includes any solvents, dispersion media, or coatings that are physiologically compatible. Preferably, the carrier is suitable for intravenous, intramuscular, oral, intraperitoneal, intradermal, transdermal, topical, nasal or subcutaneous administration. One exemplary pharmaceutically acceptable carrier is physiological saline. Other pharmaceutically acceptable carriers and their formulations are well-known and generally described in, for example, Remington's Pharmaceutical Science (18$^{th}$ Ed., ed. Gennaro, Mack Publishing Co., Easton, Pa., 1990). Various pharmaceutically acceptable excipients are well-known in the art and can be found in, for example, Handbook of Pharmaceutical Excipients (4$^{th}$ ed., Ed. Rowe et al. Pharmaceutical Press, Washington, D.C.). The composition can be formulated as a solution, microemulsion, liposome, capsule, tablet, or other suitable forms. The active component which comprises the phosphopeptide may be coated in a material to protect it from inactivation by the environment prior to reaching the target site of action. The pharmaceutical compositions of the present disclosure are preferably sterile and non-pyrogenic at the time of delivery, and are preferably stable under the conditions of manufacture and storage.

In other embodiments of the present disclosure, the pharmaceutical compositions are regulated-release formulations. Phosphopeptides of the present disclosure may be admixed with biologically compatible polymers or matrices which control the release rate of the copolymers into the immediate environment. Controlled or sustained release compositions include formulation in lipophilic depots (e.g., fatty acids, waxes, oils).

In some embodiments of the present disclosure, pharmaceutical compositions comprise phosphopeptides formulated with oil and emulsifier to form water-in-oil microparticles and/or emulsions. The oil may be any non-toxic hydrophobic material liquid at ambient temperature to about body temperature, such as edible vegetable oils including safflower oil, soybean oil, corn oil, and canola oil; or mineral oil. Chemically defined oil substance such as lauryl glycol may also be used. The emulsifier useful for this embodiment includes Span 20 (sorbitan monolaurate) and phosphatidylcholine. In some embodiments, a phosphopeptides composition is prepared as an aqueous solution and is prepared into an water-in-oil emulsion dispersed in 95 to 65% oil such as mineral oil, and 5 to 35% emulsifier such as Span 20. In another embodiment of the disclosure, the emulsion is formed with alum rather than with oil and emulsifier. These emulsions and microparticles reduce the speed of uptake of phosphopeptides, and achieve controlled delivery. In other embodiments, the pharmaceutical compositions also include additional therapeutically active agents.

In some embodiments, the additional active therapeutically active agent is selected from the group consisting of anti-psychotic drugs, anti-epileptic drugs, anti-depressive drugs and the like.

The present disclosure further provides a kit comprising (i) a composition comprising a phosphopeptide and (ii) instructions for administering the composition to a subject in need thereof at intervals greater than 24 hours, more preferably greater than 36 hours, for the treatment of disorders of the nervous system. In one embodiment, the disorder of the nervous system is epilepsy. In a preferred embodiment, the phosphopeptide is phosphor-Tat-pTrkBY816. In one embodiment, the phosphopeptide is formulated in dosages for administration multiple times daily including hourly, every 2 hours, three hours, four hours, six hours, eight hours, or twice daily including 12 hours, or any intervening interval thereof. In another embodiment, the phophopeptide is formulated in dosages for administration of greater than about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or any intervening interval thereof. In another embodiment of the kits described herein, the instructions indicate that the phosphopeptide is to be administered every about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or any interval in between. Kits may comprise additional components, such as packaging and one or more apparatuses for the administration of the phosphopeptide, such as a hypodermic syringe.

In general, an embodiment of the present disclosure is to administer a suitable dose of a therapeutic phosphopeptide composition that will be the lowest effective dose to produce a therapeutic effect, for example, mitigating symptoms. In certain embodiments, the therapeutic phosphopeptides are administered at a dose per subject, which corresponds to a dose per day of at least about 2 mg, at least about 5 mg, at least about 10 mg, or at least about 20 mg as appropriate minimal starting dosages, or about x mg, wherein x is an integer between 1 and 20. In one embodiment of the methods described herein, a dose of about 0.01 to about 500 mg/kg can be administered. In general, the effective dosage of the compound of the present disclosure is can readily be determined as routine practice by one of skill in the art. Thus the embodiments above are not meant to be a limiting, but merely representative dosage examples.

However, it is understood by one skilled in the art that the dose of the composition of the present disclosure will vary depending on the subject and upon the particular route of administration used. It is routine in the art to adjust the dosage to suit the individual subjects. Additionally, the effective amount may be based upon, among other things, the size of the compound, the biodegradability of the compound, the bioactivity of the compound and the bioavailability of the compound. If the compound does not degrade quickly, is bioavailable and highly active, a smaller amount will be required to be effective. The actual dosage suitable for a subject can easily be determined as a routine practice by one skilled in the art, for example a physician or a veterinarian given a general starting point. For example, the physician or veterinarian could start doses of the compound of the invention employed in the pharmaceutical composition at a level lower than that required in order to achieve the desired therapeutic effect, and increase the dosage with time until the desired effect is achieved.

In the context of the present disclosure, the term "treatment regimen" is meant to encompass therapeutic, palliative and prophylactic modalities of administration of one or more compositions comprising one or more phosphopeptides. A particular treatment regimen may last for a period of time which will vary depending upon the nature of the particular disease or disorder, its severity and the overall condition of the patient, and may extend from multiple daily doses, once daily, or more preferably once every 36 hours or 48 hours or longer, to once every month or several months. Following treatment, the patient is monitored for changes in his/her condition and for alleviation of the symptoms of the disorder or disease state. The dosage of the phosphopeptides may either be increased in the event the patient does not respond significantly to current dosage levels, or the dose may be decreased if an alleviation of the symptoms of the disorder or disease state is observed, or if the disorder or disease state has been ablated, or if an unacceptable side effects are seen with the starting dosage.

In one embodiment, a therapeutically effective amount of the phosphopeptide is administered to the subject in a treatment regimen comprising intervals of at least 36 hours, or more preferably 48 hours, between dosages. In another embodiment, the phosphopeptide is administered at intervals of at least 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or the equivalent amount of days. In some embodiments, the agent is administered every other day, while in other embodiments it is administered weekly. If two phosphopeptides are administered to the subject, such phosphopeptides may be administered at the same time, such as simultaneously, or essentially at the same time, such as in succession. Alternatively, their administration may be staggered. For example, two phosphopeptides which are each administered every 48 hours may both be administered on the same days, or one may be administered one day and the other on the next day and so on in an alternating fashion.

In other embodiments, the phosphopeptide is administered in a treatment regimen which comprises at least one uneven time interval, wherein at least one of the time intervals is at least 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or the equivalent amount of days.

In one embodiment, the phosphopeptide is administered to be subject at least three times during a treatment regimen, such that there are at least two time intervals between administrations. These intervals may be denoted $I_1$ and $I_2$. If the phosphopeptides is administered four times, then there would be an additional interval between the third and fourth administrations, $I_3$, such that the number of intervals for a given number "n" of administrations is n−1. In one embodiment, the interval for administration is multiple times daily including hourly, every 2 hours, three hours, four hours, six hours, eight hours, or twice daily including 12 hours, or any intervening interval thereof. Accordingly, in one embodiment, at least one of the time intervals between administrations is greater than about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours. In another embodiment, at least 1%, 2%, 3%, 4%, 5%, 10%, 15%, 20%, 25%, 30%, 40%, 50%, 60%, 70%, 80%, 90% or 95% of the total number n−1 of time intervals are at least about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours.

In yet another embodiment, the average time interval between administrations $((I_1+I_2+ \ldots +I_{n-1})/n-1)$ is at least 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or at least two weeks.

In another embodiment, the dosage regimen consists of two or more different interval sets. For example, a first part of the dosage regimen is administered to a subject multiple daily, daily, every other day, or every third day, for example, at about 22 mg phosphopeptide/m² body surface area of the subject, wherein the subject is a human. In some embodiment of the invention, the dosing regimen starts with dosing the subject every other day, every third day, weekly, biweekly, or monthly. The dosage for administration every other day or every third day may be up to about 65 mg/m² and 110 mg/m² respectively. For a dosing regimen comprising dosing of the phosphopeptide every week, the dose comprises up to about 500 mg/m², and for a dosing regimen comprising dosing of the phosphopeptide every two weeks or every month, up to 1.5 g/m² may be administered. The first part of the dosing regimen may be administered for up to 30 days, for example, 7, 14, 21, or 30 days. A subsequent second part of the dosing regimen with a different, longer interval administration with usually lower exposure (step-down dosage), administered weekly, every 14 days, or monthly may optionally follow, for example, at 500 mg/m² body surface area weekly, up to maximum of about 1.5 g/m² body surface area, continuing for 4 weeks up to two years, for example, 4, 6, 8, 12, 16, 26, 32, 40, 52, 63, 68, 78, or 104 weeks. Alternatively, if the disorder of the nervous system goes into remission or generally improves, the dosage may be maintained or kept at lower than maximum amount, for example, at 140 mg/m² body surface area weekly. If, during the step-down dosage regimen, the disease condition relapses, the first dosage regimen may be resumed until effect is seen, and the second dosing regimen may be implemented. This cycle may be repeated multiple times as necessary.

More specifically, one aspect of the disclosure is treatment of disorders of the nervous system treatable with a phosphopeptide, such as epilepsy. One embodiment of the disclosure is a method for treating disorders of the nervous system treatable with phosphopeptides of the composition YGRKKRRQRRRLQNLAKASPVpYLDI (SEQ ID NO: 3) (Phospho-Tat-pTrkBY816) in a molar input ratio of about 1.0:1.0:10.0:6.0 respectively, synthesized by solid phase chemistry, wherein the copolymer has a length of 25 amino acids, by administering said phosphopeptide to a human subject in need of treatment a first part of a dosing regimen comprising a dose of about 22 mg/m² body surface area daily. In some embodiment of the disclosure, the dosing regimen starts with dosing the subject every other day, every third day, weekly, biweekly, or monthly. The dosage for administration every other day or every third day may be up to about 65 mg/m² and 110 mg/m² respectively. For a dosing regimen comprising dosing of the phosphopeptide every week, the dose comprises up to about 500 mg/m², and for a dosing regimen comprising dosing of the phosphopeptide every two weeks or every month, up to 1.5 g/m² may be administered. The first part of the dosing regimen may be administered for up to 30 days, for example, 7, 14, 21, or 30 days. A subsequent second part of the dosing regimen with a different, longer interval administration with usually lower exposure (step-down dosage), administered weekly, every 14 days, or monthly may optionally follow, for example, at 500 mg/m$^2$ body surface area weekly, up to maximum of about 1.5 g/m$^2$ body surface area, continuing for 4 weeks up to two years, for example, 4, 6, 8, 12, 16, 26, 32, 40, 52, 63, 68, 78, or 104 weeks. Alternatively, if the disease goes into remission or generally improves, the dosage may be maintained or kept at lower than maximum amount, for example, at 140 mg/m$^2$ body surface area weekly. If, during the step-down dosage regimen, the disease condition relapses, the first dosage regimen may be resumed until effect is seen, and the second dosing regimen may be implemented. This cycle may be repeated multiple times as necessary.

Any of the methods and means may be practiced using compositions and formulations described in this application.

In other embodiments of the present disclosure, any of the methods of the disclosure may be practiced using sustained release formulation comprising a phosphopeptide. When administering a phosphopeptide of the disclosure using a sustained release formula, the overall exposure to the phosphopeptide is generally lower than in bolus administration. For example, a first part of the dosage regimen is administered to a subject daily, every other day, or every third day, for example, at about 22 mg phosphopeptide/m$^2$ body surface area of the subject, wherein the subject is a human. In some embodiment of the present disclosure, the dosing regimen uses sustained release formula, dosing the subject every other day, every third day, weekly, biweekly, or monthly so that the phosphopeptide is released during the interval. The dosage for administration every other day or every third day may be up to about 35 mg/m$^2$ and 65 mg/m$^2$ respectively. For a dosing regimen comprising dosing of the phosphopeptide every week, the dose comprises up to about 140 mg/m$^2$, and for a dosing regimen comprising dosing of the phosphopeptide every two weeks or every month, up to 750 mg/m$^2$ may be administered. The first part of the dosing regimen may be administered for up to 30 days, for example, 7, 14, 21, or 30 days. A subsequent second part of the dosing regimen with a different, longer interval administration with usually lower exposure (step-down dosage), administered weekly, every 14 days, or monthly may optionally follow, for example, at 140 mg/m$^2$ body surface area weekly, up to maximum of about 1.5 g/m$^2$ body surface area, continuing for 4 weeks up to two years, for example, 4, 6, 8, 12, 16, 26, 32, 40, 52, 63, 68, 78, or 104 weeks. Alternatively, if the disease goes into remission or generally improves, the dosage may be maintained or kept at lower than maximum amount, for example, at 140 mg/m$^2$ body surface area weekly. If, during the step-down dosage regimen, the disease condition relapses, the first dosage regimen may be resumed until effect is seen, and the second dosing regimen may be implemented. This cycle may be repeated multiple times as necessary.

In certain embodiment of the methods described herein, the route of administration can be oral, intraperitoneal, transdermal, subcutaneous, by intravenous or intramuscular injection, by inhalation, topical, intralesional, infusion; liposome-mediated delivery; topical, intrathecal, gingival pocket, rectal, intravaginal, intrabronchial, nasal, transmucosal, intestinal, ocular or otic delivery, or any other methods known in the art as one skilled in the art may easily perceive. Other embodiments of the compositions of the present disclosure incorporate particulate forms protective coatings, protease inhibitors or permeation enhancers for various routes of administration, including parenteral, pulmonary, nasal and oral. Administration can be systemic or local. In a preferred embodiment, the phosphopeptide is administered subcutaneously.

An embodiment of the methods of present disclosure relates to the administration of the copolymers of the present invention in a sustained release form. Such method comprises applying a sustained-release transdermal patch or implanting a sustained-release capsule or a coated implantable medical device so that a therapeutically effective dose of the phosphopeptide of the present disclosure is delivered at defined time intervals to a subject of such a method. The compounds and/or agents of the subject disclosure may be delivered via a capsule which allows regulated-release of the phosphopeptide over a period of time. Controlled or sustained-release compositions include formulation in lipophilic depots (e.g., fatty acids, waxes, oils). Also comprehended by the invention are particulate compositions coated with polymers (e.g., poloxamers or poloxamines).

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pre-gelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well-known in the art.

When the phosphopeptide is introduced orally, it may be mixed with other food forms and consumed in solid, semi-solid, suspension, or emulsion form; and it may be mixed with pharmaceutically acceptable carriers, including water, suspending agents, emulsifying agents, flavor enhancers, and the like. In one embodiment, the oral composition is enterically-coated. Use of enteric coatings is well known in the art. For example, Lehman (1971) teaches enteric coatings such as Eudragit S and Eudragit L. The Handbook of Pharmaceutical Excipients, 2.sup.nd Ed., also teaches Eudragit S and Eudragit L applications. Preparations for oral administration may be suitably formulated to give controlled release of the active compound.

For buccal administration, the compositions may take the form of tablets or lozenges formulated in conventional manner. The compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

The compositions may also be formulated in compositions for administration via inhalation. For such administration, the compositions for use according to the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

In certain embodiments, compositions comprising phosphopeptide are formulated in accordance with routine procedures as pharmaceutical compositions adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together. Where the composition is to be administered by infusion, it can be dispensed with an infusion bottle containing sterile pharmaceutical grade water or saline, with the intervals between administrations being greater than 24 hours, 32 hours, or more preferably greater than 36 or 48 hours. Where the composition is administered by injection, an ampoule of sterile water or saline for injection can be provided so that the ingredients may be mixed prior to administration.

In certain embodiments, the methods described herein allow continuous treatment of disorders of the nervous system by a sustained-release carrier such as transdermal patches, implantable medical devices coated with sustained-release formulations, or implantable or injectable pharmaceutical formulation suitable for sustained-release of the active components. In such embodiments, the intervals between administrations are preferably greater than 24 hours, 32 hours, or more preferably greater than 36 or 48 hours. For instance, an implantable device or a sustained released formulation which releases the phosphopeptide over a 2 day period may the implanted every four days into the patient, such that the interval during which no phosphopeptide is administered to the subject is 2 days. In related embodiments, the such interval where during which no administration occurs is at least 24+x hours, wherein x represents any positive integer.

In another embodiment, the phosphopeptides are formulated to have a therapeutic effect when administered to a subject in need thereof at time intervals of at least 24 hours. In a specific embodiment, the phosphopeptides are formulated for a long-lasting therapeutic affect such that a therapeutic effect in treating the disease is observed when the phosphopeptides are administered to the subject at time intervals of at least 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours between administrations.

In other embodiments of the methods described herein, additional therapeutically active agents are administered to the subject. In one embodiment, compositions comprising additional therapeutic agents(s) are administered to the subject as separate compositions from those comprising the phosphopeptide. For example, a subject may be administered a composition comprising a phosphopeptide subcutaneously while a composition comprising another therapeutic agent may be administered orally. The additional therapeutically active agents may treat the same disease as the phosphopeptide, a related disease, or may be intended to treat an undesirable side effect of administration of the copolymer, such as to reduce swelling at a site of intradermal injection.

EXAMPLES

The Examples which follow are illustrative of specific embodiments of the invention, and various uses thereof. They set forth for explanatory purposes only, and are not to be taken as limiting the invention.

Example 1

Biochemical Study of TrkB and PLCγ1 Signaling During Limbic Epileptogenesis

Induction of continuous seizure activity for a couple hours by systemically administered pilocarpine is followed by emergence of spontaneous recurrent seizures arising weeks thereafter, thereby recapitulating some features of temporal lobe epilepsy (TLE) in humans (Lemos, T. and Cavalheiro, E. A., (1995) *Exp. Brain Res.* 102(3): 423-428; Klitgaard, H. et al., (2002) *Epilepsy Res.* 51 (1-2): 93-107). A single intraperitoneal (i.p.) injection of pilocarpine, a muscarinic cholinergic agonist, was administered to induce status epilepticus (SE). To minimize peripheral cholinergic effects, male and female C57BL/6 mice of age 2-3 months were treated with N-methyl scopolamine nitrate (Sigma) (1 mg/kg, i.p.). Fifteen minutes later, either pilocarpine (375 mg/kg) (Sigma) or vehicle (normal saline) was injected i.p. and mice were observed for the next 3-4 hours. After 3 h of continuous seizure activity, diazepam (10 mg/kg, i.p.) was administered to mice to terminate SE. Pilocarpine-treated animals that failed to develop or did not survive SE were excluded from the study. Unless specified otherwise, both pilocarpine- and saline-mice were decapitated 6 h after the onset of SE for biochemical and immunohistochemical experiments. Following decapitation, the mouse head was quickly dipped into liquid nitrogen for 4 seconds to rapidly cool the brain. The hippocampi were rapidly dissected on ice and homogenized in lysis buffer [20 mM Tris (pH 8.0), 137 mM NaCl, 1% NP40, 10% glycerol, 1 mM sodium orthovanadate (NaOV), 1 mM phenylmethylsulfonylfuoride (PMSF), and 1 Complete Mini protease inhibitor tablet (Mini, Roche, Mannheim, Germany)/10 ml]. The supernatant was saved following centrifugation at 16,000 g for 10 min, aliquoted and stored at −80° C. for further biochemical analysis.

In experiments studying a synaptosomal membrane fraction, hippocampi were homogenized in an isotonic sucrose buffer (0.32 M sucrose, 4 mM HEPES, 1 mM NaOV, 1 mM PMSF, and 1 Mini tablet/10 ml, pH 7.4), centrifuged at 325 g for 10 min at 4° C., and the supernatant was collected and centrifuged at 16,000 g for 15 min to provide a crude synaptosomal pellet. Crude synaptosomes underwent osmotic shock by addition of ice cold deionized $H_2O$ and rapidly returned to osmotic balance with 1M HEPES pH 7.4; following centrifugation at 16,000 g for 30 min, the pellet consisting of an enriched synaptosomal membrane fraction was collected. BCA kit (Thermo Scientific, Rockford) was used to determine the protein concentration.

Western blotting was performed to analyze phosphorylated and nonphosphorylated TrkB and PLCγ1 using procedures as described previously (He X. P. et al. (2004) *Neuron* 43(1): 31-42; Huang Y. Z. et al., (2008) *Neuron* 57(4), 546-558). The following antibodies were used in these experiments: p-Trk (Y816) (a gift from Dr. Moses Chao of New York University); p-PLCγ1 (Y783) (Biosource); TrkB (BD Biosciences); PLCγ1 (Cell Signaling); actin (Sigma). The results from Western blotting were quantified by a method described previously (Huang Y. Z. et al., (2008) *Neuron* 57(4), 546-558). Briefly, the immunoreactivity of individual bands on Western blots was measured by ImageQuant software and normalized to TrkB or β-actin content; similar results were obtained with the two methods. Student's t test and one way ANOVA were used for statistical analyses. Results are presented as mean±S.E.M. for the designated number of experiments.

To test whether TrkB and PLCγ1 underwent activation in the pilocarpine model, Western blots were prepared from hippocampal homogenates isolated from wild type (+/+) mice six hours following the onset of status epilepticus induced by injection of pilocarpine Animals were handled according to National Institutes of Health Guide for the Care and Use of the Laboratory Animals and approved by Duke University Animal Care and Welfare Committee. Status epilepticus was associated with increased tyrosine phosphorylation of Trk as evidenced by increased immunoreactivity of a 145 kDa band detected by an antibody specific to pY816 Trk (FIG. 1A, top). No significant increase of TrkB content was detected (FIG. 1A, top). Quantification of pY816 immunoreactivity revealed a 2.29 fold increase in animals sacrificed six hours after status epilepticus (FIG. 1A, middle, n=7, p=0.048). The increased pY816 immunoreactivity was time dependent as revealed by modest increases evident at 30 minutes and 3 hours, more marked increases at 6-24 hours, and a return to baseline values one week later (FIG. 1A, bottom).

Because phosphorylation of Y816 of TrkB activates PLCγ1 signaling in vitro in cultured neurons and recombinant systems, the increased pY816 immunoreactivity predicted enhanced activation of PLCγ1 itself. Consistent with this prediction, increased immunoreactivity of a 150 kDa band detected by an antibody specific to pY783 PLCγ1 was detected in hippocampal homogenates isolated six hours after onset of pilocarpine-induced status epilepticus (FIG. 1B, top). No change in content of PLCγ1 itself was found (FIG. 1B). Quantification of pY783 immunoreactivity revealed a 1.79 fold increase in animals sacrificed six hours after status epilepticus (FIG. 1B, middle, n=7, p=0.004). The increased pY783 immunoreactivity was also time dependent as revealed by modest increases evident at 30 minutes and 3 hours, more marked increases at 6-12 hours, and a return to baseline values one week later (FIG. 1B, bottom).

To test whether TrkB and PLCγ signaling were activated in a distinct model of limbic epileptogenesis, Western blots were prepared from hippocampal homogenates isolated from wild type mice six hours following a Class 4/5 kindled seizure evoked by amgydala stimulation. Twelve+/+, twelve TrkB$^{WT/WT}$ and ten TrkB$^{PLC/PLC}$ mice were included in the kindling experiment. Procedures for surgery and kindling were performed as described previously by an individual blinded to genotype of the animals (He X. P. et al., (2002) *J Neurosci* 22(17): 7502-7508; He X. P. et al., (2004) *Neuron* 43(1): 31-42). Briefly, under pentobarbital (60 mg/kg) anesthesia, a bipolar electrode used for stimulation and recording was stereotactically implanted in the right amygdala. Following a post-operative recovery period of 2 weeks, the electrographic seizure threshold (EST) in the amygdala was determined and stimulations at the intensity of the EST were subsequently administered twice daily, five days per week as described previously (He X. P. et al., (2002) *J Neurosci* 22(17): 7502-7508; He X. P. et al., (2004) *Neuron* 43(1): 31-42). The behavioral manifestations of seizures were classified according to a modification of the description of Racine as described previously. (Racine R. J. et al. (1972) *Electroencephalogr Clin Neurophysiol.* 32(3):281-294). Mice were stimulated until fully kindled as defined by the occurrence of 3 consecutive seizures of class 4 or greater. Unstimulated control animals of each genotype underwent surgical implantation of an electrode in amygdala and were handled identically but were not stimulated. Six hours after the last stimulation, the stimulated and unstimulated mice were decapitated for further study. Accuracy of electrode placements were verified by histological analysis and only animals with correct electrode placement in the amygdala were included in the statistical analysis for kindling experiment. All kindling data are presented as mean±S.E.M. and analyzed by one-way ANOVA with post hoc Bonferroni's test.

The kindled seizure also resulted in increased pY816 Trk immunoreactivity (FIG. 2A, top). No significant increase of TrkB content was detected (FIG. 2A, top). Quantification of pY816 immunoreactivity revealed a 1.78 fold increase in animals sacrificed six hours after a Class 4/5 kindled seizure (n=4, p=0.037) (FIG. 2A, bottom). Consistent with this increase of pY816 Trk immunoreactivity, a kindled seizure also induced increased tyrosine phosphorylation of PLCγ1 itself six hours afterwards as evidenced by increased pY783 PLCγ1 immunoreactivity (FIG. 2B, top). No change in content of PLCγ1 itself was detected (FIG. 2B, top). Quantification of p-PLCγ1 immunoreactivity revealed a 1.92 fold increase in animals sacrificed six hours after a Class 4/5 kindled seizure (n=4, p=0.034) (FIG. 2B, bottom).

The correlation of increased pY816 Trk and pY783 PLCγ1 immunoreactivity in two distinct models of limbic epileptogenesis together with similarity of time course in the pilocarpine model provided circumstantial evidence that the enhanced PLCγ1 activation induced by status epilepticus was a consequence of activation of TrkB. The availability of trkB$^{PLC/PLC}$ mice in which substitution of phenylalanine for tyrosine at residue 816 of TrkB selectively eliminates binding and phosphorylation of PLCγ1 by TrkB enabled us to test directly in vivo whether activation of PLCγ1 during status epilepticus was a consequence of activation of TrkB.

trkB$^{PLC/PLC}$ mutant mice in a C57BL/6 background were generated by cDNA knock in approach as described previously (Minichiello L. et al., (2002) *Neuron* 36(1), 121-137). In brief, PCR-based site-directed mutagenesis was used on mouse TrkB cDNA to induce a single point mutation (A to T position 2958) that resulted in substituting phenylalanine for tyrosine 816 (Y816F), thereby disrupting the binding of PLCγ. The mutant TrkB cDNA (TrkB$^{PLC}$) and control wild-type (WT) TrkB cDNA (TrkB$^{WT}$) were knocked into the juxtamembrane exon of the mouse trkB gene. Wild type (+/+), homozygous mutant trkB (trkB$^{PLC/PLC}$) and WT knock in trkB (trkB$^{WT/WT}$) mice were used in this study. In addition, trkB$^{SHC/SHC}$ mutant mice were used in one experiment. trkB$^{SHC/SHC}$ mutant mice were generated as described previously[14] (Minichiello L. et al. (1998) *Neuron* 21(2), 335-345). In brief, PCR-aided mutagenesis was used to introduce a single point mutation (A to T, position 2055) in the trkB receptor that substituted phenylalanine for tyrosine 515 (Y515F). Nonphosphorylatable F515 disrupted the binding of adaptor protein Shc to trkB and abolished Shc site-mediated down-stream signaling events.

The genotype of each animal was assessed twice using PCR of genomic DNA isolated from tails (before and after experiments) as previously described (Croll, S. D. et al., (1999) *Neuroscience* 93(4):1491-1506). In addition to PCR, the genotype of all mice used in the kindling experiments was confirmed by sequencing.

We first examined pY816 Trk immunoreactivity in synaptic membranes isolated from trkB$^{WT/WT}$ and trkB$^{PLC/PLC}$ mice isolated six hours following status epilepticus. Consistent with findings in FIGS. 1A and 1B, status epilepticus was associated with increased pY816 Trk immunoreactivity in hippocampal synaptic membranes isolated from trkB$^{WT/WT}$ mice (FIG. 3A, top). Quantification of pY816 immunoreactivity revealed a 1.62 fold increase in trkB$^{WT/WT}$ animals sacrificed six hours after status epilepticus (FIG. 3A, bottom, n=3, p=0.013). Analysis of pY816 immunoreactivity in trkB$^{PLC/PLC}$ following treatment with normal saline revealed a 40% reduction in comparison to trkB$^{WT/WT}$ animals (FIG. 3A, top and FIG. 3A, bottom, n=3, p=0.023), demonstrating that phosphorylation of pY816 of TrkB itself contributes to pY816 immunoreactivity measured under basal conditions. Likewise following status epilepticus, the pY816 immunoreactivity in trkB$^{WT/WT}$ exceeded that in trkB$^{PLC/PLC}$ mice by 1.79 fold (FIG. 3A, top and FIG. 3A, bottom, n=3, p=0.001), demonstrating that the increased pY816 immunoreactivity following status epilepticus is due mainly to phosphorylation of TrkB. A small increase of pY816 immunoreactivity of 145 kd band was evident following status epilepticus in trkB$^{PLC/PLC}$ mice (FIG. 3A, top and FIG. 3A, bottom, n=3, p=0.033), raising the possibility that status epilepticus may also result in increased pY816 immunoreactivity of TrkC.

Next we asked whether the status epilepticus-induced activation of PLCγ1 was dependent upon TrkB activation, again probing Western blots of hippocampal synaptic membranes isolated from trkB$^{WT/WT}$ and trkB$^{PLC/PLC}$ with an antibody specific to pY783 PLCγ1. Increased pY783 PLCγ1 immunoreactivity was evident following status epilepticus in trkB$^{WT/WT}$ mice (FIG. 3B, top). Quantification of the pY783 immunoreactivity revealed a 1.96 fold increase in trkB$^{WT/WT}$ animals sacrificed six hours after status epilepticus (FIG. 3B, bottom, n=3, p=0.051). Analysis of pY783 PLCγ1 immunoreactivity in trkB$^{PLC/PLC}$ following treatment with normal saline revealed a 38% reduction in comparison to trkB$^{WT/WT}$ animals which was not statistically significant (FIG. 3B, top and FIG. 3B, bottom, n=3, p=0.291). Following status epilepticus, pY783 PLCγ1 immunoreactivity in trkB$^{WT/WT}$ exceeded that in trkB$^{PLC/PLC}$ mice by 1.84 fold (FIG. 3B, top and FIG. 3B, bottom, n=3, p=0.030), demonstrating that the status epilepticus-induced increase of pY783 PLCγ1 is almost exclusively a consequence of TrkB activation. The small absolute increase of pY783 PLCγ1 immunoreactivity in trkB$^{PLC/PLC}$ mice following status epilepticus (FIG. 3B, top and FIG. 3B, bottom, n=3, p=0.421) was not statistically significant.

Example 2

Effect of Limiting TrkB-Dependent PLCγ1 Signaling on Limbic Epileptogenesis In Vivo The evidence of enhanced TrkB dependent activation of PLCγ1 signaling during status epilepticus together with evidence of a requirement for TrkB for induction of epileptogenesis in the kindling model raised the question as to whether TrkB activation of PLCγ1 signaling is critical to epileptogenesis (He, X. P., et al., (2004) *Neuron* 43(1): 31-42). To address this question, epileptogenesis was examined in the kindling model in trkB$^{PLC/PLC}$ mice, which selectively prevents activation of the PLCγ1 signaling pathway by TrkB. trkB$^{PLC/PLC}$ mice exhibited a marked inhibition of limbic epileptogenesis, as evident in the increased number of stimulations required to elicit behavioral seizures in comparison to both +/+ and trkB$^{WT/WT}$ mice (FIG. 4A). The number of stimulations required to evoke a limbic seizure termed class 1 or 2 (FIG. 4B) was increased by more than 3 fold in trkB$^{PLC/PLC}$ mice (n=10, 9.5±2.5) compared to either of two controls (+/+2.5±0.5, n=12, p=0.004) (trkB$^{WT/WT}$, 2.8±0.4, n=12, p=0.006). Likewise the number of stimulations required to evoke the third consecutive clonic tonic seizure (Class 4 or greater) (FIG. 4B) was increased by more than 2 fold in trkB$^{PLC/PLC}$ (26.2±4.6) compared to either of two controls (+1±12.0±0.9, p=0.002) or trkB$^{WT/WT}$ (11.1±1.0, p=0.001). By contrast, no significant difference was evident in the electrographic seizure duration during kindling development among 3 genotypes. Likewise no significant differences were detected in the current required to evoke an initial electrographic seizure duration in the three groups (trkB$^{PLC/PLC}$ 128±14.1 µA; +/+150.0±27.3 µA; trkB$^{WT/WT}$ 172.7±24.5 µA; p=0.203). Together, these results demonstrate that selectively limiting activation of PLCγ signaling by TrkB markedly inhibits epileptogenesis in the kindling model.

Example 3

Immunohistochemical Localization of pY816 Trk Immunoreactivity in Limbic Epileptogenesis The pivotal role of TrkB dependent PLCγ1 signaling in limbic epileptogenesis in the kindling model raised the question as to potential cellular consequences of the enhanced activation of TrkB and PLCγ1 that might contribute to epileptogenesis. Insight into the anatomic locale of the enhanced TrkB activation would provide a valuable clue as to the nature and locale of potential cellular mechanisms. Previous studies provided immunohistochemical evidence that TrkB receptors undergo increased phosphorylation during epileptogenesis in a spatially specific pattern in the hippocampus, that is, increased phospho-Trk (pY515) was evident in the mossy fiber pathway in multiple models (Binder, D. K. et al., (1999) *J. Neurosci.* 19(11): 4616-4626; He, X. P. et al., (2002) *J. Neurosci.* 22(17): 7502-7508). That said, the anatomic locale of enhanced pY816 Trk immunoreactivity during epileptogenesis is unknown. To address this question, we performed pY816 immunohistochemistry in 2 models of limbic epileptogenesis, namely pilocarpine-induced status epilepticus and kindling.

P-Trk immunohistochemistry was performed using the protocol described previously (Danzer, S. C. et al., (2009) *Hippocampus* (in press); Danzer, S. C. et al., (2004) *J. Neurosci.* 24(50): 11346-11355). Briefly, under pentobarbital anesthesia (100 mg/kg), mice were perfused with 4% paraformaldehyde in PBS and the brains were removed, post-fixed and cryoprotected. Forty µm coronal sections were cut and used for immunofluorescent staining After 1 h incubation with blocking solution (5% NGS, 0.5% NP40 in PBS buffer with 1 mM NaOV), pY816 antibody was applied to floating sections overnight at 4° C. Alexa Fluor 594 goat anti-rabbit secondary antibody (Invitrogen) was used to visualize the immunofluorescent staining. The sections from experimental and control animals of different genotypes were processed simultaneously in the same incubation plates using the identical solutions and protocol so that valid comparisons could be made. Images were captured and quantified using a Leica (Nussloch, Germany) TCS SL confocal system. Immunoreactivity over the corpus callosum was sampled in each section because of its low immunoreactivity and used as internal control; in addition values were collected from a square of fixed size over CA1 stratum oriens, CA1 stratum lacunosum-moleculare, and CA3a stratum lucidum (FIG. 7B) and presented as percent of value of corpus callosum. The specificity of pY816 antibody for TrkB pY816 was verified by the marked reductions of immunoreactivity in stratum lucidum of trkB$^{PLC/PLC}$ compared to control mice (FIG. 7A). All results from experimental mice and their controls were analyzed by Student's t test.

The immunohistochemical pattern in sections prepared from WT mice sacrificed 6 h after onset of status epilepticus revealed increased pY816 Trk immunoreactivity in the stratum lucidum of CA3a bilaterally (only one hippocampus shown) in all brain sections examined (FIG. 5A, top); no overt changes of p-Trk immunoreactivity were noted elsewhere in the hippocampus. Quantification revealed a 1.66 fold increase of pY816 immunoreactivity in CA3a stratum lucidum in pilocarpine (n=6) compared to normal saline (n=5) treated animals (p=0.015) (FIG. 5A, bottom). By contrast, no significant changes were detected in stratum oriens or lacunosum-moleculare of CA1. Like the pilocarpine model, increased pY816 Trk immunoreactivity was detected in the mossy fiber pathway of hippocampus bilaterally of animals sacrificed 6 hours after the last Class 4/5 seizure evoked by amygdala stimulation in the kindling model compared to sham-stimulated controls (FIG. 5B, top). Quantification revealed 2.60 fold increase of pY816 immunoreactivity in CA3a stratum lucidum in kindled (n=4) compared to control group (n=3) (p=0.033) (FIG. 5B, bottom). By contrast, no significant changes were detected in stratum oriens or lacunosum-moleculare of CA1.

Example 4

Inhibition of Long-Term Potentiation (LTP) of Mossy Fiber-CA3 Pyramid Synapse in trkB$^{PLC/PLC}$ Mice The anatomic localization of the increased pY816 Trk immunoreactivity to the mossy fiber pathway directed study of potential cellular consequences of TrkB activation to this locale. The presence of status epilepticus-induced increases of pY816 Trk and pY783 PLCγ1 immunoreactivity in synaptic membranes (FIGS. 3A and 3B) directed study of cellular consequences to synaptic events in particular. One consequence of TrkB activation at synapses in this locale that might promote limbic epileptogenesis is development of LTP of the excitatory synapse of mf axons of dentate granule cells with CA3 pyramidal cells. Our previous studies demonstrated that inhibiting TrkB kinase activity eliminated LTP of this synapse induced by high frequency stimulation (HFS) of the dentate granule cells (Huang, Y. et al., (2008) Neuron 57 (4):546-558). To determine whether TrkB signaling through PLCγ in particular is required for LTP of this synapse, the effects of HFS of the mossy fibers (mfs) on the efficacy of this synapse were compared in trkB$^{PLC/PLC}$ and control mice.

For hippocampal slice preparation and electrophysiology, mice (P28-P42) were anesthetized with pentobarbital and decapitated. The brain was quickly removed and placed in ice-cold buffer containing (in mM): sucrose 110, NaCl 60, KCl 3, NaH$_2$PO$_4$ 1.25, NaHCO$_3$ 28, CaCl$_2$ 0.5, MgCl$_2$ 7.0, and dextrose 5, saturated with 95% O$_2$ plus 5% CO$_2$, pH 7.4. Following dissection of hippocampi, transverse slices (400 µm in thickness) were cut with a vibratome and incubated in oxygenated artificial cerebrospinal fluid (ACSF) containing (in mM): NaCl 124, KCl 1.75, KH$_2$PO$_4$ 1.25, NaHCO$_3$ 26, CaCl$_2$ 2.4, MgCl$_2$ 1.3, and Dextrose 10 for at least 1 hour at 32-34° before recording. The slices were then transferred to a recording chamber mounted on Zeiss Axioskop upright microscope.

The following criteria were applied to be considered a mossy fiber excitatory postsynaptic field potentials (fEPSP): a) the ratio for paired pulse facilitation (PPF) at 60 msec interval was 1.75 or greater; b) frequency facilitation at 20 Hz was 2.0 or greater as determined by the ratio of the amplitude of the response to the third pulse compared to the first pulse; and c) application of the Group II metabotropic glutamate receptor (mGluR) II agonist 2-(2,3-dicarboxycyclopropy) glycine (DCG-IV) 1 µM at the end of the experiment reduced the amplitude of the evoked fEPSP by at least 70% (Toth, K. et al. (2000) J. Neurosci. 20(22): 8279-8289). Addition of picrotoxin, which blocks feed forward inhibition of CA3 pyramids evoked by mossy fiber activation of interneurons in stratum lucidum did not modify the latency, amplitude, or waveform of the mf-CA3 pyramid fEPSP. The mossy fiber-CA3 pyramid fEPSPs were induced by a bipolar tungsten stimulating electrode placed at the junction of the granule cell layer and hilus near the midpoint of the suprapyramidal blade of the dentate. Extracellular recordings were obtained with a glass micropipette filled with 2 M NaCl, 2-6 MCl resistance placed in stratum lucidum near the junction of CA3a and CA3b. An input-output curve was obtained by hilar stimulation (0.2 ms square pulses delivered at 0.03 Hz) with a Digitmer constant current stimulator (DS3). A stimulus intensity sufficient to induce a fEPSP amplitude approximating 30% of the maximum amplitude was used for these experiments. D, L-APV (100 µM) was included in perfusion solution to eliminate contamination of associational-commissural afferents (Li, Y. et al. (2001) J. Neurosci. 21(20): 8015-8025). LTP was induced by applying a total of 4 trains of high frequency stimulation (HFS) (each train consisting of 200 µsec pulses at 100 Hz and intensity sufficient to induce maximum fEPSP amplitude and intertrain interval of 10 s. To assure objectivity, the individual performing all experiments with wild type and mutant mice was blinded as to genotype.

For the LTP experiment, the amplitude of fEPSPs was measured and LTP was plotted as mean percentage change in the fEPSP amplitude 50-60 min after HFS relative to the 10 min of fEPSP amplitude immediately preceding the HFS. The numbers listed in the Figure legends and text refer to the number of animals. Results are typically obtained and averaged from at least two slices from each animal and the average value is presented as a single value for each animal. Data were collected from slices at room temperature using a Multi 700A amplifier and pClamp 9.2 software (Axon Instruments). The synaptic responses were filtered at 2 kHz and digitized at 5 kHz. All data were presented as mean±S.E.M. and analyzed by Student's t test with Excel (Microsoft) and Prism (GraphPad Software) software.

Significant (p<0.01) impairments of HFS-induced LTP of the mf-CA3 pyramid synapse were detected in slices isolated from trkB$^{PLC/PLC}$ (115±3%, n=7) compared to WT (155±9%, n=8) or trkB$^{WT/WT}$(148±3.9%, n=7) control mice (FIGS. 6A and 6B). Importantly, no differences in basal synaptic transmission were detected between TrkB$^{PLC/PLC}$ and control mice as evident in part by similar ratios of paired pulse facilitation of the fEPSP in the three groups (PPF: +/+, 2.56±0.5, n=5; trkB$^{PLC/PLC}$, 1.83±0.3, n=5, p>0.05, t test and trkB$^{WT/WT}$1.95±0.3, n=5, P>0.05, t test). Moreover, the impairment of mf-LTP was specific to the PLCγ1 signaling pathway because no differences in LTP of the mf-CA3 pyramid synapse were detected in trkB$^{SHC/SHC}$ compared to WT control mice (+/+, 144±7%, n=6; trkB$^{SHC/SHC}$, 145±7%, n=5, P>0.05, t test). Together, these data demonstrate that TrkB-dependent signaling through the PLCγ1 but not the Shc pathway is required for LTP of the mf-CA3 pyramid synapse.

To determine whether neurotrophin receptor, TrkB, promotes limbic epileptogenesis by activation of the PLCγ1 signaling pathway, biochemical, immunohistochemical, and electrophysiological studies utilizing trkB$^{WT/WT}$ and trkB$^{PLC/PLC}$ mice were performed. Again, trkB$^{PLC/PLC}$ mice have a substitution of phenylalanine for tyrosine at residue 816 of TrkB (pY816 TrkB), which selectively eliminates binding and phosphorylation of PLCγ1 by TrkB, thereby permitting study of functional consequences of TrkB-mediated activation of PLCγ1 in vivo (Minichiello L. et al., (2002) Neuron 36(1), 121-137).

Based on these studies, it was found that time-dependent increases of both pY816 Trk and pY783 PLCγ1 immunoreactivity were detected in hippocampi of WT mice in the pilocarpine and kindling models. The enhanced pY783 PLCγ1 immunoreactivity in the pilocarpine model was decreased in hippocampi isolated from trkB$^{PLC/PLC}$ mice. It was also discovered that limbic epileptogenesis as measured by development of kindling was markedly inhibited in trkB$^{PLC/PLC}$ mice. Furthermore, enhanced pY816 Trk immunoreactivity in WT mice was localized to the mossy fiber pathway within hippocampus in these models, and LTP of the mossy fiber-CA3 pyramid synapse was impaired in slices of trkB$^{PLC/PLC}$ mice. We conclude that activation of pY783 PLCγ1 is due to TrkB activation in these models and that TrkB-induced PLCγ1 signaling promotes limbic epileptogenesis.

The biochemical data provide evidence of enhanced activation of both TrkB and PLCγ1 signaling in hippocampus of WT mice in both the pilocarpine and kindling models of limbic epileptogenesis. The time course data demonstrated that activation of both TrkB and PLCγ1 signaling begins shortly after onset of status epilepticus, peaks in magnitude at 6-24 hours, and returns to baseline by one week afterwards. Similarity in the time course of the increased immunoreactivity of TrkB and PLCγ1 (FIGS. 1A and 1B) provided circumstantial evidence that TrkB activation causes the activation of PLCγ1. Remarkably, the enhanced activation of PLCγ1 following status epilepticus was markedly reduced in the trkB$^{PLC/PLC}$ mice, providing direct evidence that TrkB activation caused PLCγ1 activation in vivo and that other signaling pathways had little or no effect in PLCγ1 activation. The increased pY816 Trk immunoreactivity extends previous evidence of increased pY515 TrkB immunoreactivity in the kindling and kainic acid models, suggesting that TrkB enhances signaling via both Shc and PLCγ1 pathways during limbic epileptogenesis (He, X. P. et al. (2002) J. Neurosci. 22(17): 7502-7508; He, X. P. et al., (2004) Neuron 43(1): 31-42). Activation of PLCγ1 results in hydrolysis of phosphatidyl inositol bisphosphate (PIP2) and formation of DAG and IP3, the subsequent IP3-mediated activation of IP3 receptors of endoplasmic reticulum (ER) resulting in increased calcium release from the ER. The present findings suggest that TrkB-mediated activation of PLCγ1 may contribute to the increased IP3 detected in hippocampus following kainic acid evoked seizures (Carmant, L. et al. (1995) Brain Res. Dev. Brain Res. 89(1): 67-72). Likewise, excessive activation of TrkB-mediated PLCγ1 signaling likely contributes to sustained increases of cytoplasmic calcium and impaired uptake of calcium by ER Ca-ATPase evident in hippocampal CA1 pyramidal cells after pilocarpine status epilepticus (Raza, M. et al., (2004) Proc. Natl. Acad. Sci. USA 101(50): 17522-17527).

The biochemical evidence of TrkB-dependent activation of PLCγ1 signaling notwithstanding, the question arose as to whether activation of this signaling pathway contributes to epileptogenesis in vivo. The marked inhibition of development of kindling of trkB$^{PLC/PLC}$ compared to control mice establishes a causal role for TrkB-dependent PLCγ1 signaling in limbic epileptogenesis in vivo. The specificity of distinct pathways downstream of TrkB with respect to this pathological phenotype is remarkable. That is, the increases of both pY515 and pY816 immunoreactivity in diverse models of limbic epileptogenesis suggests that TrkB enhances activation of both she and PLCγ1 signaling (Binder, D. K. et al., (1999) J. Neurosci. 19(11): 4616-4626). Yet in contrast to the marked inhibition of development of kindling in trkB$^{PLC/PLC}$ mice, no differences in development of kindling were detected between WT and trkB$^{SHC/SHC}$ mice (He, X. et al., (2002) J. Neurosci. 22(17): 7502-7508).

Although inhibition of kindling is marked in trkB$^{PLC/PLC}$ mice, the magnitude of inhibition was less than reported previously with conditional trkB null mutants in which trkB was recombined from CNS neurons by crossing synapsin-cre with floxed trkB mice (He, X. P. et al., (2004) Neuron 43(1): 31-42). Notably, the mutation of the trkB$^{PLC/PLC}$ is in the germline whereas the onset of trkB recombination is delayed until late in embryonic development in the synapsin-cre trkB$^{FLOX/FLOX}$; perhaps the expression of the perturbation of TrkB signaling earlier in the life of the trkB$^{PLC/PLC}$ mice compared to the conditional null mutants facilitates emergence of a compensatory mechanism that underlies persistence of epileptogenesis. Alternatively, some residual TrkB-dependent signaling persisting in the trkB$^{PLC/PLC}$ mice may contribute to epileptogenesis whereas elimination of TrkB protein itself in the conditional null mutants would eliminate all TrkB-dependent signaling.

The inhibition of epileptogenesis in the trkB$^{PLC/PLC}$ mice provides a valuable insight as to a cellular mechanism by which enhanced activation of TrkB may promote limbic epileptogenesis. Both ex vivo and in vivo studies of animal models advance LTP of excitatory synapses between principal cells as an attractive cellular mechanism of limbic epileptogenesis wherein potentiation of these synapses appears to facilitate propagation of seizure activity through synaptically coupled neuronal populations widely throughout the limbic system and beyond (Sutula, T. et al., (1987) Brain Res. 420(1): 109-117; Mody, I. and Heinemann U. (1987) Nature 326(6114): 701.704). LTP of the excitatory synapse between Schaffer collateral axons of CA3 pyramids with CA1 pyramids was previously shown to be impaired in slices isolated from trkB$^{PLC/PLC}$ mice but to be normal in slices from trkB$^{SHC/SHC}$ mice (Minichiello, L. et al., (2002) Neuron 36(1): 121-137). The localization of the increased pY816 TrkB immunoreactivity specifically to the mossy fiber pathway of hippocampus in both the pilocarpine and kindling models provided the rationale for testing whether TrkB-dependent PLCγ1 signaling is required for LTP of the synapse between mossy fiber axons of dentate granule cells with CA3 pyramidal cells. Like earlier studies of the Schaffer collateral-CA1 synapse, LTP of the mf-CA3 synapse was partially impaired in slices isolated from trkB$^{PLC/PLC}$ compared to control mice. Earlier studies demonstrated that the mf-CA3 pyramid synapse undergoes LTP in vivo in the kainic acid model of limbic epileptogenesis (Goussakov, I. V. et al., (2000) J. Neurosci. 20(9): 3434-3441). The requirement for TrkB-dependent PLCγ1 signaling for LTP of this synapse together with evidence of increased pY816 immunoreactivity specifically to the mossy fiber pathway of the hippocampus in both pilocarpine and kindling models provides a rationale for examining whether TrkB-dependent PLCγ1 signaling is required for LTP of the synapse between mossy fiber axons. Notably, the fact that LTP of the mf-CA3 synapse in the trkB$^{SHC/SHC}$ mice was similar to controls parallels the similarity in rate of development of kindling in trkB$^{SHC/SHC}$ and control mice (He, X. et al., (2002) *J. Neurosci.* 22(17): 7502-7508). Enhanced excitability in models of epilepsy is often accompanied and likely caused by both enhanced function of excitatory synapses and impaired function of inhibitory synapses. Collectively, study of human epileptic tissue (Cohen et al., 2002; Huberfeld et al., 2007) buttressed by study of diverse in vivo and in vitro models (Woo et al., 2002; Rivera et al., 2002, 2004; Pathak et al., 2007; Li et al., 2008; Blaesse et al., 2009) advance reduced expression of KCC2 and resulting accumulation of [Cl-]$_i$ as an important molecular and cellular mechanism contributing to limbic epilepsy. Interestingly, in vitro studies reveal that TrkB-mediated activation of PLCγ1 signaling can suppress KCC2 expression (Rivera et al., 2002, 2004). Whether TrkB-mediated activation of PLCγ1 signaling promotes reductions of KCC2 expression described in the kindling and pilocarpine models (Rivera et al., 2002; Li et al., 2008) in vivo is unclear.

TrkB is only one of three cell surface receptors whose activation has been causally linked to epileptogenesis in adults, the other two being the NMDA and metabotropic glutamate receptors (McNamara, J. O. et al., (2006) *Sci STKE* 356:re12). Diverse antagonists of the NMDA receptor partially inhibit epileptogenesis in a multitude of in vitro and in vivo models (Holmes, K. H. et al., (1990) *Brain Res.* 506(2):227-235; McNamara, J. O. et al., (1988) *Neuropharmacology* 27(6): 563-568; Stasheff, S. F., et al., (1989) *Science* 245(4918): 648-651; Prasad, A. et al., (2002) *Ann. Neurol.* 51(2): 175-181). Although NR2A containing NMDA receptors in particular have been implicated in epileptogenesis in the kindling model in vivo, the signaling pathways activated by NR2A containing NMDA receptors that promote epileptogenesis are unknown. With respect to metabotropic glutamate receptors, bath application of a Group 1 metabotropic glutamate receptor agonist, DHPG, to hippocampal slices induced persistent epileptiform activity in vitro (Sprengel, R. et al., (1998) *Cell* 92(2): 279-289; Merlin, L. R. et al., (1997) *J. Neurophysiol.* 78(1): 539-544). In contrast to receptor tyrosine kinases like TrkB which are coupled to PLCγ, the Group 1 metabotropic receptors are coupled to G-proteins and through G-proteins to PLCβ7 (Rebecchi, M. J. et al., (2000) *C. Physiol. Rev.* 80(4): 1291-1335). Interestingly, induction of epileptogenesis by DHPG was inhibited by a PLC inhibitor in vitro and also in slices isolated from PLCβ1 null mutant mice, suggesting that activation of PLCβ1 signaling mediates metabotropic glutamate receptor induced epileptogenesis. Whether activation of Group 1 metabotropic receptors by endogenous glutamate induces epileptogenesis in vivo is unknown. Paradoxically, PLCβ1 null mutant mice exhibit epileptic seizures underscoring the importance of elucidating the contribution of Group 1 metabotropic glutamate receptor-mediated PLCβ (activation to epileptogenesis in vivo (Kim, D. et al., (1997) *Nature* 389(6648): 290-293).

In closing, the studies provided above identify a single signaling pathway activated by a single receptor contributing to epileptogenesis in vivo, namely TrkB dependent activation of PLCγ1 signaling. Whereas a pharmacological approach might inhibit PLCγ1 activated by diverse membrane receptors, only PLCγ1 activated by TrkB is inhibited in the trkB$^{PLC/PLC}$ mutant mice. The present report is novel among studies of CNS disorders in that it implicates a specific signaling pathway directly coupled to a single membrane receptor in vivo. The specificity of TrkB-dependent PLCγ1 signaling is remarkable in that TrkB-dependent activation of signaling via the she adaptor protein has no effect on epileptogenesis in vivo. Give the great diversity of signaling pathways activated during a process as complex as epileptogenesis, the causal role of a single signaling pathway activated by a single receptor is striking (Huang, Y. Z. et al., (2008) *Neuron* 57(4): 546-558). The fact that epileptogenesis is inhibited in trkB$^{PLC/PLC}$ but not trkB$^{SHC/SHC}$ mice implies that anti-epileptogenic therapies need not necessarily target TrkB itself, thereby circumventing potential unwanted consequences of global inhibition of TrkB. Novel downstream targets suggested by the present findings include inhibition of PLCγ1 itself or preventing the interaction between TrkB and PLCγ1. Our findings illustrate that dissecting signaling pathways directly coupled to a single cell membrane receptor in vivo aids in the elucidation of novel targets for specific and effective therapeutic intervention of CNS disorders.

Example 5

Identification of Phosphopeptides that Effectively and Selectively Inhibit TrkB-Mediated Activation of PLCγ1: Peptide Construction BDNF is a secreted 14 kDa polypeptide that binds to the ectodomain of TrkB, inducing receptor dimerization, resulting in increased intrinsic kinase activity and autophosphorylation of tyrosines including Y705/Y706, Y515, and Y816 within the intracellular domain, in turn triggering activation of downstream signaling pathways including PLCγ1. A diversity of scientific evidence supports the conclusion that enhanced activation of PLCγ1 signaling by TrkB promotes epileptogenesis and neuropathic pain. Thus developing a selective inhibitor of TrkB-mediated activation of PLCγ1 signaling should provide a valuable tool for inhibiting epileptogenesis and neuropathic pain. Availability of phosphopeptide that selectively inhibited TrkB-mediated activation of PLCγ1 signaling is one approach to developing a therapeutic agent. That said, the neuronal circuits mediating epileptogenesis and neuropathic pain reside in the central nervous system and access of molecules like peptides to these circuits is limited by the blood-brain barrier. Interestingly, recent studies have established the feasibility of systemically administered peptides including a tat sequence permeating the blood-brain barrier and limiting protein-protein interactions and exerting beneficial effects in animal models of CNS disorders. We therefore sought to identify a peptide fused to a tat sequence that would permeate the plasma membrane of cultured neurons and the blood-brain barrier of rodent brain, and selectively and effectively limit activation of PLCγ1 signaling by TrkB.

Phospho-Tat-pTrkBY816 (YGRKKRRQRRRLQN-LAKASPVpYLDI) (SEQ ID NO: 3) peptide was synthesized and purified by Tufts University Core Facility. The peptide LQNLAKASPVpYLDI (SEQ ID NO: 5) corresponds to amino acids 806-819 of human TrkB. This peptide sequence is identical in TrkB among human, rat, and mouse. Our success in raising antibodies that recognize conformational epitopes in mouse TrkB with this phosphopeptide suggested that this synthesized peptide is able to mimic the conformation of p-TrkY816 in vivo and likely binds to its substrate PLCγ1. Because this sequence of TrkB is considered to be critical to bind PLCγ1 with increased affinity when Y816 is phosphorylated, a peptide with the identical amino acids but in which the sequence was scrambled (Scr-phospho-Tat-pTrkBY816) was also obtained. The sequence of Scr-phospho-Tat-pTrkBY816 is: YGRK-KRRQRRRLVApYQLKIAPNDLS (SEQ ID NO: 6). The sequence YGRKKRRQRRR (SEQ ID NO: 2) corresponds to HIV tat peptide 47-57; fusion peptides containing this sequence have been shown to permeate plasma membranes of cells in vitro in addition to permeating the blood-brain barrier in vivo.

Example 6

Preincubation of Cortical Neurons with Phospho-Tat-pTrkBY816 Inhibits BDNF-Mediated Activation of PLCγ1 in a Concentration-Dependent Manner Primary cortical neuron culture was performed as follows. Mixed neuronal-glia primary cultures of rat cortex were prepared from rat embryos (E18-19). In brief, the cortices were isolated in and cells were plated on poly-L-lysine-treated plates and cultured in Neural Basal medium with B27 supplement containing 10% fetal bovine serum (FBS) and other supplements including 33 mM glucose and 100 U/ml penicillin/streptomycin for the initial 24 hr at 37° C. in 5% CO2. The medium was switched to FBS free medium from 2 DIV. Half of the medium was changed every 3 days. Neurons cultured for 14 days were used for the experiments described below.

Primary cultured cortical neurons were treated with Tat-pTrkBY816 at 0.1 μM, 1 μM or 10 μM for 90 mins, BDNF was added for 15 mins and cell lysate was prepared for immunoblotting. Phosphorylation of PLCγ1 at tyrosine 783 was used as a surrogate measure of PLCγ1 activation. Addition of BDNF (10 ng/ml) for 15 mins resulted in increased pPLCγ1 783 immunoreactivity (compare lane 2 with lane 1, FIG. 8). Preincubation of the neurons with Tat-pTrkBY816 0.1 μM did not inhibit BDNF-mediated activation of PLCγ1 whereas 1 μM and 10 μM limited the BDNF-induced increase of pPLCγ1 783 in a concentration dependent manner (lanes 3, 4, 5 of FIG. 8).

For Western blot analysis, cultured cells were lysed in modified RIPA buffer (50 mM Tris-HCl, pH 7.4, 150 mM NaCl, 1% NP 40, 0.25% sodium deoxycholate) with 1 mM EDTA, 1 mM EGTA, 1 mM sodium orthovanadate and proteinase inhibitors and briefly centrifuged. The supernatant was mixed at a volume ratio of 4:1 to 10 mmol/L TrisHCl buffer (pH 6.8) containing 10% glycerol, 2% sodium dodecylsulfate, 0.01% bromophenol blue and 5% mercaptoethanol, followed by mixing and boiling at 100° C. for 10 min. Aliquots (10 μg protein) were loaded on a 8% polyacrylamide gel for electrophoresis at a constant voltage at 115 v for 90 min at 25° C. After electrophoresis, the protein bands were electrotransferred onto a nitrocellulose membrane. The membrane was then blocked by 5% bovine serum albumin (BSA) dissolved in 20 mmol/L TrisHCl buffer (pH 7.5) containing 137 mmol/L NaCl and 0.05% Tween 20 and the membrane subsequently incubated with anti-pan Trk, pTrkBY816, pTrkBY515, PLCγ1, pPLCG1Y763, pERK, pAkt and beta-tubulin respectively (dilution ratio 1:1000), diluted with the buffer containing 1% BSA overnight, followed by the reaction with horseradish peroxidase-conjugated anti-rabbit IgG (dilution ratio 1:1000) or anti-mouse IgG (dilution ratio 1:5000) for 1 h at 25° C. respectively. Proteins reactive with those antibodies were detected with the aid of enhanced chemiluminescence detection reagents through exposure to X-ray films.

Example 7

Preincubation of Cortical Neurons with Phospho-Tat-pTrkBY816 Inhibits BDNF-Mediated Activation of PLCγ1 in a Selective and Time-Dependent Manner Embryonic (E18) rat cortical neurons cultured for 12 DIV were used in these experiments. Either phospho-Tat-TrkBY816 peptide (10 μM) or Scr-phospho-Tat-TrkBY816 was added to the neurons for varying periods of time (10, 30, 60, 90 and 120 mins) prior to addition to BDNF (10 ng/ml). Following 15 min incubation with BDNF or vehicle, cells were solubilized and lysates were subjected to SDS-PAGE and western blotting with a diversity of antibodies. Preincubation with phospho-Tat-TrkBY816 peptide (10 μM) for periods ranging from 60-120 min inhibited BDNF-mediated increased p-PLCγ1 783; this inhibition was selective in that BDNF-mediated increases of pAkt and pErk were not affected (FIG. 9). The inhibition of p-PLCγ1 783 by phospho-Tat-TrkBY816 was also selective in that no inhibition was evident in neurons preincubated with scrambled phospho-Tat-TrkBY816 (10 μM) (FIG. 9). The results evident in FIG. 9 were quantified and are presented in FIGS. 10, 11, and 12 in which values represent means±SEM of two or three experiments.

Example 8

Systemic Administration of Tat-pTRKBY816 Inhibits PLCγ1 In Vivo

An important issue with respect to usefulness of Tat-pTRKBY816 is whether, following peripheral administration, the peptide can inhibit PLCγ1 activation in the brain in vivo. To test this idea, adult C57/B6 mice underwent tail vein injection of vehicle (normal saline [NS]) or Tat-scrambled-pTrkY816 or Tat-pTrkBY816 (10 mg/kg, 2 mice per group) Animals were sacrificed 3 hours post administration, the hippocampus dissected and homogenate prepared for western blotting. As shown in FIG. 13, top row, Tat-pTrkBY816 reduced the phosphor-PLCγ1 in comparison to either saline or Tat-scrambled-pTRKBY816. Content of PLCγ1 (FIG. 13, bottom row) was not affected. These findings support the assertion that the peptide passes through the blood brain barrier and inhibits PLCγ1 activation in vivo.

Example 9

Intravenous Administration of Peptide Tat-pTrkBY816 Inhibits Chemoconvulsant-Induced Status Epilepticus In Vivo To demonstrate the efficacy of systemically administered Tat-pTrkBY816 in vivo, we examined its effects on status epilepticus induced by microinjection of the chemoconvulsant, kainic acid, into the right amygdala of adult mice using the method described by Moria G. et al., (2008) *Brain Research* 1213, 140-151. As described previously, microinjection of kainic acid into the right amygdala of awake, adult mice reliably induces continuous limbic and clonic motor seizures accompanied by electrographic evidence of seizure activity as detected by EEG recording electrode in the contralateral hippocampus. Status epilepticus is terminated by intraperitoneal administration of diazepam 45 minutes following infusion of kainic acid. Treated animals typically exhibit normal behavior when observed 24 hours thereafter; importantly, epileptic seizures arise 3-4 days thereafter and persist for at least 4-6 weeks (Moria G. et al., (2008) *Brain Research* 1213, 140-151, unpublished confirmation from our laboratory).

We asked whether intravenous infusion of Tat-pTrkBY816 via tail vein inhibited status epilepticus induced by microinjection of kainic acid into the right amygdala (FIG. 15) Animals were pretreated with infusion of Tat-pTrkBY816 (10 mg/kg) or a scrambled control peptide scr-Tat-pTrkBY816 (10 mg/kg) at different times prior to kainic acid administration and animals were observed for development of status epilepticus as assessed by behavioral evidence of limbic and tonic-clonic seizures (FIG. 16). Kainic acid induced status epilepticus in 23 of 24 animals pretreated with scrambled control peptide (FIG. 16, top); by contrast, pretreatment with Tat-pTrkBY816 (10 mg/kg) produced a striking time dependent inhibition of status epilepticus ((FIG. 16, top). Onset of inhibition was detected at the earliest time tested (0.16 hour), peaked at 0.5 hour when status epilepticus was eliminated altogether, persisted for 24 hours, and remitted by 72 hours. The latency to the onset of status epilepticus was also prolonged in animals treated with Tat-pTrkBY816 (10 mg/kg) compared to the scrambled control peptide scr-Tat-pTrkBY816 (10 mg/kg) (FIG. 16, bottom). The inhibition of status epilepticus was also dose dependent Animals were pretreated with infusion of varying doses of Tat-pTrkBY816 or a scrambled control peptide scr-Tat-pTrkBY816 six hours prior to kainic acid administration and animals were observed for development of status epilepticus as assessed by behavioral evidence of limbic and tonic-clonic seizures (FIG. 17). Whereas a dose of 1 mg/kg of Tat-pTrkBY816 was ineffective, doses of 3 mg/kg and 10 mg/kg effected a striking inhibition such that status epilepticus was prevented in at least 70% of animals (FIG. 17, top). By contrast, kainic acid induced status epilepticus in all animals pretreated with the control scr-Tat-pTrkBY816 regardless of dose (FIG. 17, top). Likewise pretreatment with Tat-pTrkBY816 but not control scr-Tat-pTrkBY816 peptide increased the latency to onset of behavioral status epilepticus in a dose dependent fashion (FIG. 17, bottom).

Example 10

Anticonvulsant Effects of Genetic Inhibition of TrkB-Mediated PLCγ1 Signaling

An anticonvulsant effect of TrkB kinase inhibition has been observed in seizures evoked by electrical stimulation (Liu et al., 2014 in press) but the responsible signaling pathway downstream of TrkB is unknown. The pivotal role of TrkB-PLCγ1 signaling in limbic epileptogenesis (He, X. P. et al., (2010) *J Neurosci* 30:6188-6196; He, X. P. et al., (2014) *Epilepsia* 55(3):456-463, led to the examination of the following hypothesis: limiting TrkB-mediated activation of PLCγ1 in particular would suppress limbic seizures. To test this hypothesis, initial experiments utilized trkB$^{PLC/PLC}$ mice in which a phenylalanine is substituted for tyrosine at residue 816 TrkB, thereby disrupting TrkB-mediated PLCγ1 signaling (Minichiello, L. et al., (2002) *Neuron* (36) 121-137). Continuous seizures (SE) were induced by local infusion of the chemoconvulsant, kainic acid (KA), into the right amygdala of adult mice and both behavior and EEG were monitored continuously for 45 min following KA infusion (FIGS. 18A and 18B, schematic diagram of experimental design). Infusion of KA induced prolonged convulsive motor and electrographic seizures in each wild type control animal (trkB$^{WT/WT}$, 21.4±3.8 min and 20.0±3.3 min, respectively, n=8) (FIG. 18C, 18E, 18F and FIG. 19). By contrast, the duration of convulsive motor and electrographic seizures were reduced by 80-90%, in trkB$^{PLC/PLC}$ mice (1.2±0.8 min and 4.1±1.5 min, respectively, p<0.001 for each compared to controls, n=9) (FIGS. 18C, 18E, 18F and FIG. 19). Quantification of EEG power during 45 min following KA infusion revealed significant reductions in trkB$^{PLC/PLC}$ compared to trkB$^{WT/WT}$ mice (FIGS. 18C and 18D). These findings demonstrate that genetically uncoupling TrkB from adaptor proteins and enzymes that bind the motif containing Y816 result in powerful anticonvulsant effects.

Evidence that the pY816 motif of TrkB mediates the binding and activation of PLCγ1 suggested that the mechanism by which seizures were suppressed in trkB$^{PLC/PLC}$ mice was mediated by inhibiting PLCγ1 signaling. That said, multiple adaptor proteins and enzymes can bind a given motif of a RTK. To test whether limiting signaling thru PLCγ1 in particular is the mechanism of the anticonvulsant effects in the trkB$^{PLC/PLC}$ mice, the responses to KA infusion in mice heterozygous for PLCγ1 (PLCγ1$^{+/-}$) in comparison to wild type control were tested. Notably, hippocampal expression of PLCγ1 protein is reduced by approximately 50% in PLCγ1$^{+/-}$ mice (He, X. P. et al., (2014) *Epilepsia* 55(3):456-463; Ji, Q. S. et al., (1997) *P NATL ACAD SCI USA* 94:2999-3003). Infusion of KA induced prolonged convulsive motor and electrographic seizures in each wild type control animal (25.0±2.0 min and 23.0±3.6 min, respectively, n=4) (FIGS. 18G, 18H, and 18I and FIGS. 19C and 19D). By comparison, the duration of convulsive motor and electrographic seizures were reduced by 60-70% in PLCγ1$^{+/-}$ mice (7.1±1.9 min and 9.5±2.2 min, p<0.001 and 0.01, respectively, n=8) (FIGS. 18G, 18H, and 18I and FIG. 19C). Quantification of EEG power during 45 min following KA infusion revealed significant reductions in PLCγ1$^{+/-}$ compared to wild type control mice (FIG. 1G). These findings demonstrate that reducing the expression of PLCγ1 results in powerful anticonvulsant effects and support the conclusion that the dominant mechanism underlying the anticonvulsant effects of the trkB$^{PLC/PLC}$ mutation involves inhibition of PLCγ1 activation. Collectively, these findings provide a strong rationale for development of therapeutic agents that disrupt the interaction of TrkB with PLCγ1.

In the animal studies described for Examples 10-14, Adult male C57BL/6 mice (25-30 g) and embryonic 18 (E18) pregnant Sprague Dawley rats were obtained from Charles River Laboratory. TrkB 816 site point mutant mice (trkB$^{PLC/PLC}$) and wild-type (WT) knockin trkB controls (trkB$^{WT/WT}$) were generated as previously described (Minichiello, L. et al., (2002) *Neuron* (36) 121-137). Heterozygotes of PLCγ1 mutant mice (PLCγ1$^{+/-}$) and WT littermates (PLCγ1$^{+/-}$) were generated as previously described (Ji, Q. S. et al., (1997) *PNAS USA* 94:2999-3003). Animals were housed under a 12 hr light/dark cycle with food and water ad libitum. Animals were handled according to National Institutes of Health Guide for the Care and Use of the Laboratory Animals and approved by Duke University Animal Care and Welfare Committee.

trkB$^{WT/WT}$ and trkB$^{PLC/PLC}$ mutant mice on a C57BL/6-129 background were generated by cDNA knockin approach as described previously (Minichiello, L. et al., (2002) *Neuron* (36) 121-137). In brief, PCR-based site-directed mutagenesis was used on mouse TrkB cDNA to induce a single point mutation (A to T position 2958) that resulted in substituting phenylalanine for tyrosine 816 (Y816F), thereby disrupting the binding of PLCγ1. The mutant TrkB cDNA (TrkB$^{PLC}$) and control wild-type (WT) TrkB cDNA (TrkB$^{WT}$) were knocked into the juxtamembrane exon of the mouse trkB gene. Adult male and female homozygous mutant trkB (trkB$^{PLC/PLC}$) and WT knockin trkB (trkB$^{WT/WT}$) mice were used in this study. PLCγ 1 mutant mice were generated by targeted deletion of genomic sequences encoding the X domain and both SH2 domains of PLCγ1 as described previously (Ji, Q. S. et al., (1997) *PNAS USA* 94:2999-3003). Inbred strains of PLCγ1 mutant mice were crossed on a 129/SvJ background to C57BL/6 for six generations. Note that the line generated with replacement vector TV-1 was used in these experiments. Homozygous disruption of PLCγ1 (−/−) results in embryonic lethality at approximately embryonic day 9.0-9.5. Therefore, adult male and female heterozygotes of PLCγ1 (PLCγ1$^{+/−}$) and WT littermates (PLCγ1$^{+/+}$) were used in studies. The genotype of each animal was assessed using polymerase chain reaction (PCR) of genomic DNA isolated from tails.

Surgery and microinfusion studies provided in Examples 10-14 were performed as described here. Surgery and microinfusion of KA into right amygdala of adult mice was performed as previously described (Liu, G. et al., (2013) *Neuron* 79:31-38). Briefly, mice were anesthetized with pentobarbital (60 mg/kg, intraperitoneally [i.p.]) and placed in a stereotaxic frame. A guide cannula was stereotactically placed above the right amygdala (coordinates from bregma: AP=−1.2 mm; ML=−3.0 mm). A bipolar electrode was placed in the left dorsal hippocampus (coordinates from bregma: AP=−2.0 mm; ML=−1.6 mm; DV=−1.5 mm). A ground electrode connected to a screw was placed in the skull above the cerebellum. After a postoperative recovery period of 7 days, the animal was gently restrained and an infusion cannula was inserted into the right amygdala through the guide cannula at the depth of 3.7 mm below dura. Either KA (0.3 μg in 0.5 μl PBS) or vehicle control (0.5 μl of PBS) was infused into the right basolateral amygdala at the rate of 0.11 μl per minute. The infusion cannula was left in the right amygdala for two additional minutes before being withdrawn from the guide cannula. Animals were housed individually for time locked electroencephalogram (EEG) telemetry and video monitoring with food and water ad libitum.

Emergence of SE was typically evident in EEG recordings 5-10 min after KA infusion. The behavioral seizures associated with electrographic seizures typically consisted of immobility, followed by facial automatisms, unilateral or bilateral forelimb clonus, and whole body clonus. Tonic-clonic seizures with loss of posture and jumping also occurred during the seizures (Mouri, G. et al., (2008) *Brain Res* 1213:140-151). For experiments in which p816 or Scr was administered prior to SE, mice were monitored for 45 min following KA infusion. EEG patterns consistent with electrographic SE included any of the following: 1. discrete electrographic seizures; 2. waxing and waning epileptiform activity; 3. continuous, high amplitude, rapid spiking; 4. periodic epileptiform discharges on a relatively flat background as described by Treiman, D. M. et al., (1990) *Epilepsy Res* 5:49-60 and Walton, et. al., (1988) *Exp Neurol* 101:267-275. Behavioral patterns consistent with seizures included Classes 3-6 as described in the following section (Racine, R. J. (1972) *Electroencephalogr Clin Neurophysiol* 32:281-294; Borges, K. et al., (2003) *Exp Neurol* 182:21-34). The duration of behavioral and electrographic SE were determined by analyses of video and EEG data by trained observers blinded to treatment of mice. A similar method was used in experiments examining effects of mutations (trkB$^{PLC/PLC}$ and PLCγ1$^{+/−}$) on SE induced by KA. For experiments in which p816 or Scr was administered following SE, diazepam (10 mg/kg, i.p.) was administered 40 minutes after the onset of SE followed by lorazepam (6 mg/kg, i.p.) one hour later to suppress SE and limit the mortality and morbidity of this model. Animals underwent continuous video-EEG monitoring 24 hr per day, 7 days per week for first two weeks post-SE (day 1-14). At the end of the second week post-SE, monitoring was discontinued and animals were returned to home cages. After a two-week interval, monitoring was resumed for an additional two weeks (day 29-42). Spontaneous recurrent seizures were identified by review of video-EEG files by independently by each of two trained readers blinded to treatment of mice. The consistency of identifying SRS between readers was ~90%; in instances in which readers disagreed, the events were excluded from this study. SRS was defined electrographically as high frequency (>5 Hz), high amplitude (>2× baseline) rhythmic epileptiform activity with a minimal duration of 5 s and behaviorally with video-monitoring (see behavioral-seizure scoring).

Behavioral seizures during SE and SRS were classified according to a modification of Racine scale for mice (Racine, R. J. (1972) *Electroencephalogr Clin Neurophysiol* 32:281-294; Borges, K. et al., (2003) *Exp Neurol* 182:21-34): 0, normal activity; 1, arrest and rigid posture; 2, head nodding; 3, partial body clonus (unilateral forelimb clonus); 4, rearing with bilateral forelimbs clonus; 5, rearing and falling (loss of postural control); 6, tonic-clonic seizures with running and/or jumping.

Continuous hippocampal EEG telemetry (Grass Instrument Co.) and time-locked video were monitored using Harmonie software (Stellate Systems, Natus Medical). Monitoring started 15 min before amygdala KA infusion for recording baseline EEG and behavioral activity. Animals underwent continuous video-EEG monitoring 24 hr per day and behavioral and EEG data were analyzed by an observer blinded to genotype and treatment as previously described (Liu, G. et al., (2013) *Neuron* 79:31-38). Quantitative analysis of EEG energy content was performed using the method described by (Lehmkuhle, M. J. et al., (2009) *J Neurophysiol* 101:1660-1670). For experiments in which p816 or Scr was administered following SE, the EEG energy content during 40 min of SE (FIG. 19C), during the 60 min interval between treatment with diazepam and lorazepam, and during the 60 min interval after lorazepam (FIG. 19D) were normalized to 5 min of baseline collected prior to KA infusion. For experiments in which p816 or Scr was administered prior to SE, the EEG energy content was measured during 45 min after infusion of KA and compared to 5 min of baseline collected prior to KA infusion; a similar method was used in experiments examining effects of mutations (trkB$^{PLC/PLC}$ and PLCγ1$^{+/−}$) on SE induced by KA.

All data are presented as the mean±standard error of the mean (SEM). Unless otherwise stated, comparisons between two groups were analyzed using unpaired Student's t-test, while multi-group comparisons were analyzed using one-way ANOVA followed by Tukey's post-hoc tests. A p<0.05 was considered significant.

Example 11 pY816 Inhibits PLCγ1 Activation Both In Vitro and In Vivo

In order to selectively uncouple PLCγ1 from activated TrkB, an interfering molecule was designed. A membranepermeable peptide comprising HIV-1 Tat protein transduction domain and a sequence of human TrkB, which is required for binding of PLCγ1 to the motif of TrkB containing tyrosine 816, was generated (pY816, YGRK-KRRQRRR-LQNLAKASPVpYLDI) (SEQ ID NO: 1) (Obermeier, A. et al., (1993) *The EMBO journal* 12:933-941). A HIV-1 Tat conjugated randomly scrambled peptide (Scr, YGRKKRRQRRR-LYApYQLKIAPNDLS) (SEQ ID NO: 6) served as a negative control for this study (Figure S1A).

HIV-1 Tat protein transduction domain (YGRK-KRRQRRR) (SEQ ID NO: 2) was conjugated to a sequence on the N-terminus of human TrkB (807-820) with tyrosine (residue 817 of human and 816 of mouse and rat) phosphorylated (pY816, YGRKKRRQRRR-LQN-LAKASPVpYLDI) (SEQ ID NO: 1). A HIV-1 Tat protein transduction domain conjugated to a scrambled peptide (YGRKKRRQRRR-LVApYQLKIAPNDLS) (SEQ ID NO: 6) served as control. Peptides were synthesized and purified by Tufts Peptide Core Facility. Peptides were dissolved in phosphate-buffered saline (PBS) at 2 mg/ml and stored at −80° C. until use. Frozen aliquots of pY816 and Scr were thawed and injected intravenously (i.v.) shortly thereafter. All reagents were purchased from Sigma unless specified otherwise.

The following hypothesis were tested: 1) whether preincubation of pY816 can selectively inhibit TrkB-mediated PLCγ1 activation in cultured neurons in vitro; and 2) whether systemic administration of pY816 can disrupt TrkB-PLCγ1 binding and inhibit PLCγ1 activation in nave mice in vivo. To examine the concentration dependence of pY816-mediated inhibition of TrkB mediated PLCγ1 activation in vitro, pY816 or Scr was preincubated at various concentrations (1, 5 or 10 μM) 90 min prior to addition of BDNF (10 ng/ml) to cultured neurons. Cell lysates were subjected to Western blotting and quantification of p-PLCγ1 (pY783), a surrogate measure of PLCγ1 activation (Segal, R. A. et al., (1996) *J Biol Chem* 271:20175-20181). Preincubation of pY816 (10 μM) produced an 79.3% inhibition of BDNF mediated PLCγ1 activation (FIGS. 21A and 21B, compared to Scr, p<0.001). To assess the time course of inhibition, either pY816 or Scr (each 10 μM) was preincubated at varying intervals (10, 30, 60, 90 and 120 min) prior to addition of BDNF to cultured neurons. Preincubation of pY816 for 60 or 120 min prior to addition of BDNF produced marked inhibition of BDNF-mediated PLCγ1 activation (68.2% and 94.5%, respectively) (FIGS. 21C and 21D, compared to Scr, p<0.001). Importantly, pY816-mediated inhibition was selective to PLCγ1 in that BDNF-mediated increases of p-Akt and p-ERK were not affected (FIGS. 21A and 21C, rows 3 and 5).

Dissociated neuronal cultures were prepared as described previously (Huang, Y. Z. et al., (2008) *Neuron* 57:546-558). Briefly, cortical mixed neuron and glia cultures were prepared from pups of E18 pregnant SD rats. Cells were cultured in Neurobasal with B27 supplement for 12-17 days in vitro (DIV) before use. Medium was replaced with artificial cerebrospinal fluid (ACSF) buffer before BDNF (10 ng/ml, Chemicon) stimulation. 15 min after addition of BDNF, cells were lysed in modified RIPA buffer (20 mM Tris, pH 7.5, 137 mM sodium chloride, 1% NP40, 0.25% sodium deoxycholate, 1 mM sodium orthovanadate, 1 mM PMSF, and one complete Mini protease inhibitor cocktail tablet [Roche]/10 ml), briefly centrifuged, and the supernatant was used for western blotting.

Animals were anesthetized with pentobarbital (200 mg/kg i.p.) and decapitated, and the head was quickly immersed in liquid nitrogen for 4 s to rapidly cool the brain. The hippocampi were rapidly dissected on ice and homogenized in RIPA buffer, incubated on ice for 15 min, and centrifuged at 200,000×g for 10 min at 4° C. The supernatant was collected and stored at −80° C. until further analysis. TrkB was immunoprecipitated using TrkB antibody (1:1000, Millipore) and the lysates were incubated with 100 μL of protein A-Sepharose beads (Roche) overnight in 4° C. The beads/immune complexes were pelleted in a microcentrifuge and then resuspended in RIPA buffer and this procedure was repeated two additional times before adding 2×SDS PAGE sample buffer and boiled. After SDS PAGE, the gels were probed with TrkB and PLCγ1 antibody (1:1000, Cell signaling). Western blotting was conducted as previously described (He et al., 2010). Cell lysate and hippocampal homogenate were probed with p-PLCγ1 (pY783), PLCγ1, p-Akt (pS473), Akt, p-ERK (p44/p42) and ERK (1:1000, Cell signaling). The immunoreactivity of individual bands on western blots was measured by ImageJ software (National Institutes of Health) and normalized to PLCγ1, Akt or ERK contents. Equivalent protein loading among samples was monitored by β-actin (1:10000; Sigma) levels. Shown are representative results of immunoblotting from at least three independent experiments.

A key question regarding the usefulness of pY816 is whether it can effectively and selectively disrupt TrkB-PLCγ1 binding and inhibit PLCγ1 activation in brain in vivo following peripheral administration. To address this question, either Scr or pY816 (10 mg/kg) was injected intravenously (i.v.) into nave C57BL/6 mice and animals were euthanized 3 hr later, hippocampi dissected, and biochemical studies performed. Compared to Scr, injection of pY816 inhibited the co-imunoprecipitation of TrkB and PLCγ1 (FIG. 21E). Systemic infusion of pY816 also reduced p-PLCγ1 (pY783) immunoreactivity by ~50% in comparison to Scr injection as revealed by Western blotting of hippocampal lysates (FIGS. 21F and 21G, p<0.01). Importantly, the effect of pY816 was selective to PLCγ in that neither p-Akt nor p-ERK was affected (FIG. 21F, rows 3 and 5). Collectively, these experiments demonstrate that pY816 selectively inhibits BDNF-mediated TrkB dependent PLCγ1 activation in a time- and concentration-dependent manner in vitro and selectively inhibits PLCγ1 activation in brain following systemic administration in vivo.

Neurons and astrocytes were visualized using antibodies against neuronal nuclei (mouse monoclonal to NeuN, 1:500; Millipore) and glial fibrillary acidic protein (rabbit polyclonal to GFAP, 1:1000; Sigma) detected with Alexafluor 488 coupled anti-mouse and Alexafluor 594 coupled anti-rabbit secondary antibodies (Molecular Probes), respectively. Images were captured using a Leica TCS SL confocal microscopy system equipped with a 63× oil-immersion objective lens. NeuN-positive cell counting was performed by an investigator blinded to the genotype and treatment conditions with ImageJ software (Ferreira, T. et al., (2011). *The ImageJ User Guide*) in a 260×260 μm field within the CA3b pyramidal cell layer. Mean counts were obtained from two adjacent rostral and two adjacent middle hippocampal sections ipsilateral to the infused amygdala.

Example 12

Anticonvulsant Effects of Pharmacological Inhibition of TrkB-Mediated PLCγ1 Signaling The genetic evidence that disrupting TrkB from PLCγ1 exerts anticonvulsant effects together with facts that pY816 is able to inhibit PLCγ1 activation in vitro and in vivo led to the examination of whether systemic administration of pY816 exerted anticonvulsant effects in the KA model. Towards this end, either pY816 or Scr was administered (i.v.) prior to KA infusion and both behavior and EEG seizures were monitored for 45 min following KA infusion (FIG. 22A, schematic diagram of experimental design). To optimize the effects, we asked how varying doses and intervals of administration affected seizures evoked by KA. Infusion of KA locally into amygdala induced prolonged convulsive motor and electrographic seizures following i.v. infusion of Scr (FIGS. 22B, 22C, and 22F). By contrast, i.v. infusion of pY816 (6 hr prior to KA) inhibited convulsive motor and electrographic seizures in a dose-dependent manner, the maximal inhibition of 90% obtained with 10 mg/kg, (FIGS. 22B, 22C, and 22F and FIG. 23). The inhibition of convulsive motor and electrographic seizures by i.v. infused pY816 (10 mg/kg) was also time dependent (FIGS. 22D and 22E). Inhibitory effects were evident as early as 10 min following i.v. infusion and inhibition of 80-90% persisted for 24 hr, returning to control levels by 72 hr (FIGS. 22D and 22E). Collectively, these results support the conclusion that pY816 inhibits SE induced by KA infusion in a manner that is dependent on both dose and time.

Example 13

Figure 24:
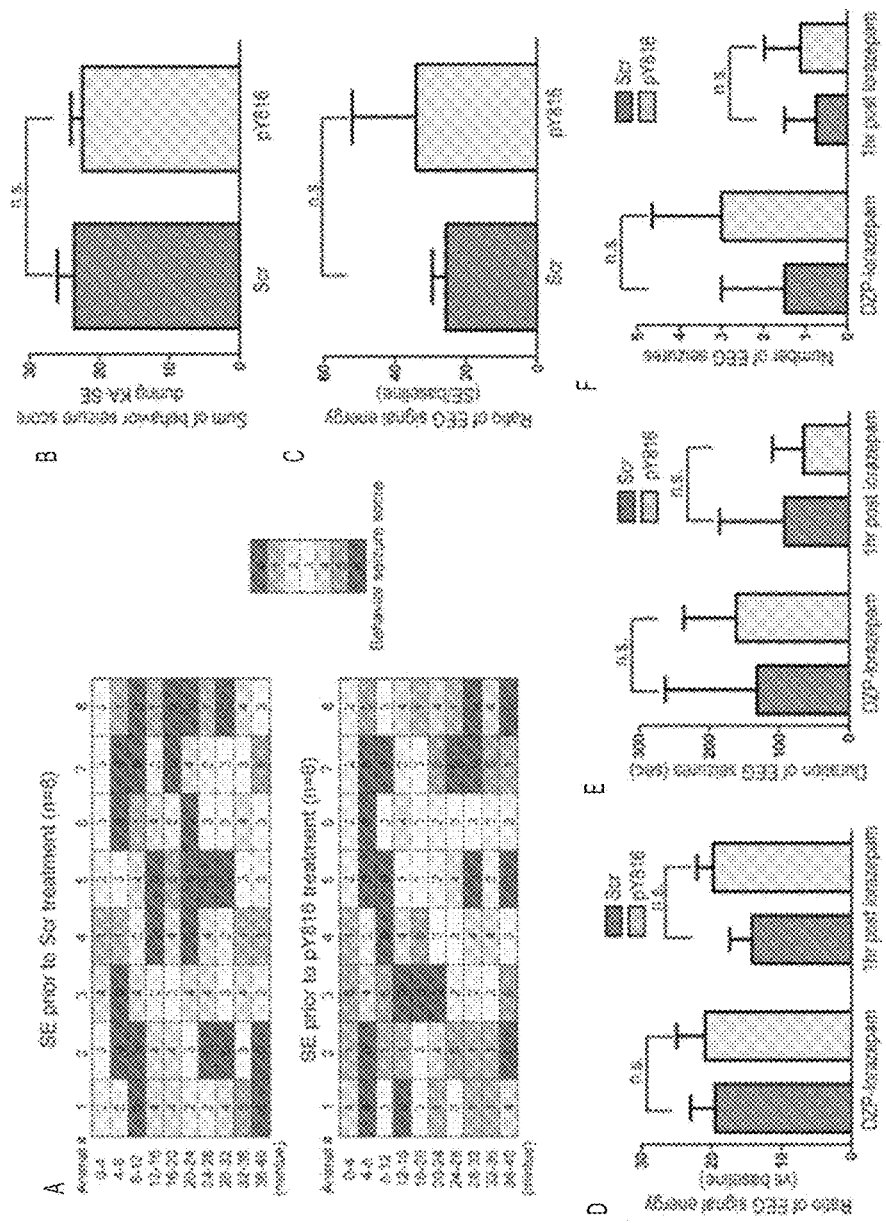

Antiepileptogenic and Antianxiogenic Effects of Transient Inhibition of TrkB-Mediated PLCγ1 Signaling Following KA-SE Transient inhibition of TrkB kinase initiated following SE was recently demonstrated to prevent SE-induced epilepsy and anxiety-like behavior (Liu, G. et al., (2013) *Neuron* 79:31-38). The experiments presented in the preceding paragraph demonstrate that administration of pY816 prior to the chemoconvulsant inhibited the chemoconvulsant-evoked seizures. Herein it was then assessed whether administration of pY816 following chemoconvulsant-evoked SE prevented SE-induced epilepsy and anxiety-like behavior. Importantly, to address this question, it is necessary to withhold pharmacological intervention until completion of the insult, thereby permitting comparison of effects of pY816 and Scr control on animals that experienced insults (SE) of similar severity. (FIG. 24).

To guide design of this experiment, an understanding of the time course of SE-induced activation of PLCγ1 was important in that a critical period of enhanced activation following SE would provide a therapeutic window during which inhibition of TrkB-PLCγ1 signaling could potentially prevent emergence of spontaneous recurrent seizure (SRS). To address this question, SE was induced by infusion of KA into the amygdala and terminated after 40 min by injection of diazepam (10 mg/kg, i.p.). Mice were sacrificed immediately (0 hr), 6 hr, 24 hr, 48 hr and 72 hr after diazepam treatment and the hippocampus ipsilateral to infusion site was prepared for Western blotting. SE-induced activation of PLCγ1 (detected as ratio of p-PLCγ1 [pY783] to PLCγ1 immunoreactivity) approximating 2-3 fold that was maximal in first 24 hr following SE and returned to normal by 72 hr (0 and 6 hr, $p<0.01$; 24 hr, $p<0.05$, n=3) (FIGS. 25A and 25B). To determine whether SE-induced activation of PLCγ1 could be inhibited by pY816, we injected varying doses of pY816 (1, 10, and 20 mg/kg, i.v.) or Scr control (20 mg/kg, i.v.) immediately after treatment with diazepam and euthanized the mice 6 hr later (FIGS. 25C and 25D). Injection of pY816 produced a dose-dependent inhibition of SE-induced activation of PLCγ1, inhibition approximating 75% with doses of 10 and 20 mg/kg (FIGS. 25C and 25D, $p<0.05$, n=3).

Figure 22:
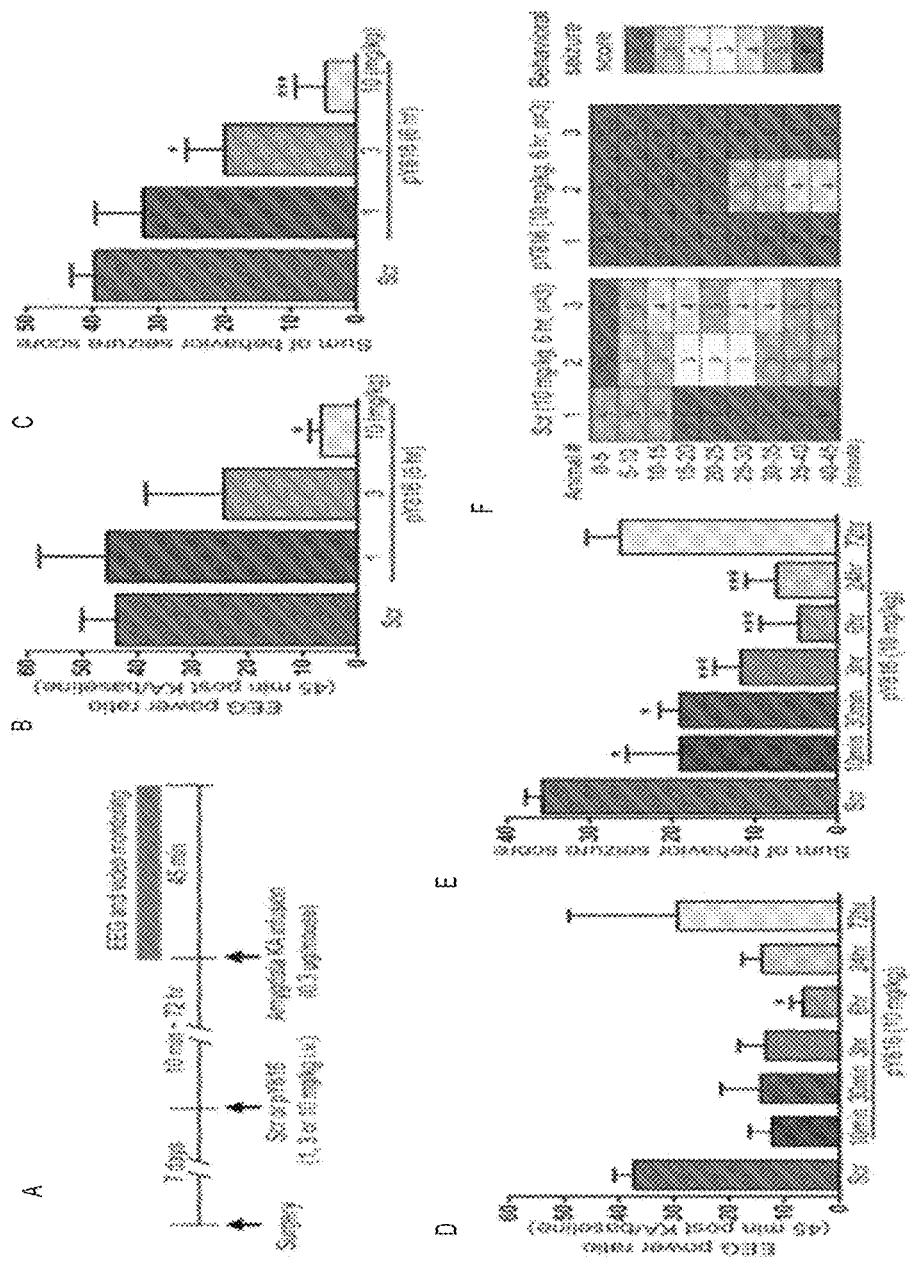
Figure 25:
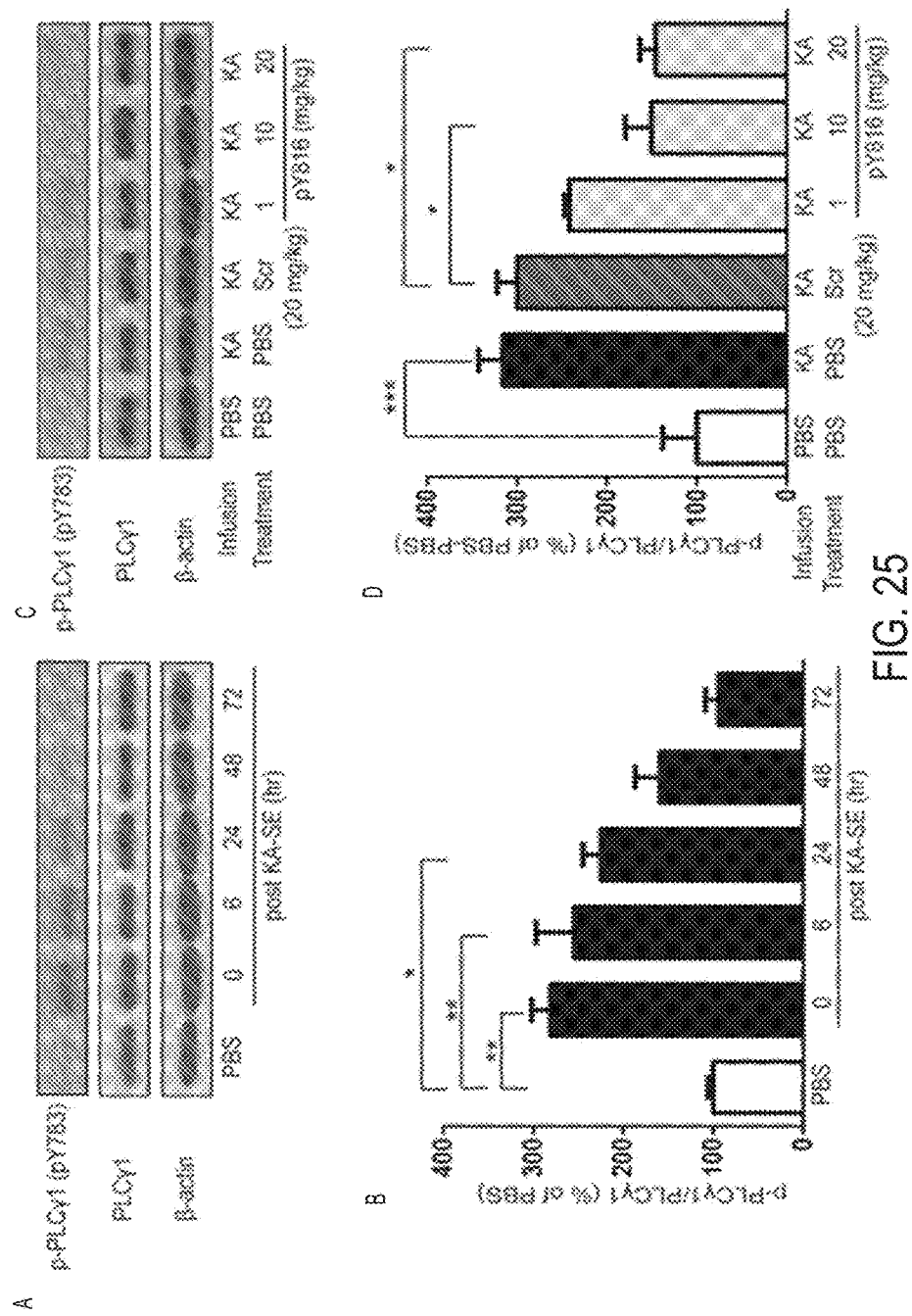

Information obtained from the experiments presented above was used to design an experiment addressing whether treatment with pY816 initiated following SE could prevent SE-induced epilepsy and anxiety-like behavior. Knowledge of the time course of SE-induced PLCγ1 activation, of the dose of pY816 required to inhibit SE-induced PLCγ1 activation, and of the duration of pY816-mediated suppression of KA-evoked seizures (FIGS. 22 and 25) led to administering pY816 (10 mg/kg, i.v.) immediately, 24 hr and 48 hr after diazepam treatment. Continuous video-EEG recordings to detect seizures were conducted during days 1-14 and day 29-42 after SE (FIG. 26A, schematic diagram of experimental design). Analyses of results collected during days 1-14 revealed protective effects of pY816 (FIG. 26C top panels and 26D). The latency to the onset of the first spontaneous seizure was delayed in pY816 compared to control animals. The initial spontaneous seizure was observed in 5 of 8 control animals within 3 days following SE whereas a single pY816 infused animal exhibited a seizure in this interval. Moreover, a marked reduction (86%) in the number of spontaneous seizures was observed in pY816 compared to Scr control animals (Scr: 18.1±1.7; pY816: 2.4±0.6. $p<0.001$, n=8) (FIG. 26D, left panel). Additional video-EEG recordings were conducted during a two week epoch (Days 29-42) initiated approximately four weeks after the last dose of pY816. This long interval was selected to assure elimination of pY816; notably, measures of biochemical and seizure suppressant effects of pY816 revealed that efficacy of an i.v. dose had dissipated three days thereafter (FIGS. 22 and 25). Once again, a marked reduction (90%) in the number of spontaneous seizures was observed in pY816 compared to Scr control animals (Scr: 16.5±3.5; pY816: 1.5±0.4. $p<0.001$, n=8) (FIG. 26D, right panel). Among the eight animals treated with pY816, two exhibited no seizures and the remaining six animals exhibited only 1-3 seizures. By contrast, control animals exhibited 7-36 spontaneous recurrent seizures during this same interval (FIGS. 26C and 26D).

Patients with TLE commonly exhibit anxiety disorders and anxiety-like behavior has been documented in animal models of TLE (Beyenburg, S. et al., (2005) *Epilepsy Behav* 7:161-171). Anxiety-like behavior has been observed months following SE in the model studied here and was found to be prevented by transient inhibition of TrkB kinase commencing after SE (Liu, G. et al., (2013) *Neuron* 79:31-38). It was therefore tested whether this SE-induced behavioral abnormality could also be prevented by treatment with pY816 initiated following SE. To address this question, following completion of video-EEG recording during days 29-42, anxiety-like behavior was assessed using the light-dark emergence test (Bourin, M. et al., (2003) *Eur J Pharmacol* 463:55-65).

Specifically, a plexiglas arena (40×40×40 cm) was placed in a room with homogenous illumination (~300 lux). The arena was subdivided into sixteen 10×10 cm squares by lines marked on the floor. Each mouse was placed in the center of the open field and allowed to explore freely the apparatus for 5 minutes. The apparatus (20×40×40 cm) consisted of two acrylic compartments. The dark compartment (30×40 cm) and light compartment (40×40×40 cm, brightly illuminated at 600 lux) were separated by a divider with a 5.5×5.5 cm opening at floor level. Mice were placed into the dark side and allowed to move freely between the two chambers with the door open for 5 minutes. During behavior tests, a video camera was mounted directly above the arena to monitor animal activity and movement. An investigator unaware of the treatment reviewed the video and recorded: 1) line crossing (frequency of crossing grid lines with all four paws) and the frequency of rearing (standing on hind legs or leaning against the walls of the arena) to assess locomotor activity in open field test; and 2) the latency to first entry into lighted compartment (entering the lighted side with all four paws) and the total time spent on the lighted side to assess anxiety-like behavior in light/dark box test.

Following completion of video-EEG monitoring for recurrent seizures, all KA-infused mice were subjected to open field and light/dark box tests at 8 weeks post-SE. Control animals underwent infusion of PBS into the amygdala and subsequently i.v. infusion of Scr or pY816 peptide and were tested 8 weeks after PBS infusion. No differences were found between Scr and pY816 treated control animals and these groups were combined for analyses.

In comparison to controls (n=7) in which PBS was infused into the amygdala and treated with either Scr or pY816 (no differences were found between treatment, thereby combined for analyses), mice undergoing SE followed by treatment with Scr exhibited a prolonged latency to enter the lighted compartment (p<0.05) (FIG. 27A) and spent less time in lighted compartment (p<0.05) (FIG. 27B). By comparison to the Scr, mice given pY816 for 3 days following SE exhibited a significantly reduced latency to enter the lighted compartment (p<0.05) (FIG. 27A) and spent increased time in the lighted compartment (p<0.01) (FIG. 27B). Similarities in locomotor activity in an open field between two groups undergoing SE excluded differences in spontaneous activity as a confounding variable in the light-dark emergence results (data not shown). Collectively, these results demonstrate that treatment with pY816 for three days commencing after SE prevents SE-induced anxiety-like behavior, providing evidence of anti-anxiogenic effects of this peptide.

Example 14

Neuroprotective Effects of Inhibition of PLCγ1 Following SE

Death of hippocampal neurons and reactive gliosis are well recognized neuropathological features of TLE in humans (Mathern, G. W. et al., (1998) *Epilepsy: a comprehensive textbook* 1:133-156) and similar features have been identified in the hippocampus ipsilateral to the KA-infused amygdala 2 weeks following SE (Mouri, G. et al., (2008) *Brain Res* 1213:140-151). Histological analyses of mice given Scr after SE and euthanized 10 weeks thereafter revealed ~50% reduction of neurons (NeuN immunoreactive cells) in CA3b hippocampus compared to control animals undergoing PBS infusion into amygdala (FIGS. 28A and 28B, rostral, p<0.01, middle, p<0.001), confirming results of Mouri, G. et al., (2008) *Brain Res* 1213:140-151. Compared to Scr treatment, pY816 significantly reduced the neuron loss by ~30% (FIGS. 28A and 28B, rostral, p<0.05, middle, p<0.05). Reactive gliosis evidenced by enlarged GFAP-immunoreactive cells with thickened processes in CA3b of hippocampus were observed following SE in Scr treated animals (FIG. 7A, bottom row), confirming a previous report of Mouri et al. (2008). Importantly, these abnormalities were attenuated by pY816 treatment following SE (FIG. 28A, bottom row).

Ten weeks following SE, mice were anesthetized with pentobarbital (200 mg/kg, i.p.) and underwent intra-cardiac perfusion with PBS containing heparin (5 U/ml) followed by 4% paraformaldehyde. Brains were removed, frozen by slow immersion in isopentane chilled in dry ice, cryoprotected, and sectioned. Serial 40 μm coronal sections were cut through the forebrain spanning the entire hippocampus. Adjacent sections at two levels relative to bregma (~1.68 mm posterior designated "rostral") or (~2.32 mm posterior designated "middle") were stained for NeuN and GFAP as previously described (Mouri, G. et al., (2008) *Brain Res* 1213:140-151) and mean counts of NeuN positive cells were obtained from two adjacent rostral and two adjacent middle hippocampal sections ipsilateral to the infused amygdala by an observer blinded to treatment.

In sum, these findings establish the efficacy of systemically administered Tat-pTrkBY816 for inhibiting development of status epilepticus induced by kainic acid. Together with genetic evidence that uncoupling TrkB from PLCγ1 exhibits anti-epileptogenic effects in the kindling model, the present findings demonstrate that pharmacologically disrupting this signaling pathway with the Tat-pTrkBY816 peptide de novo in the adult brain powerfully inhibits an epileptogenic stimulus, and more particularly, kainic acid-induced status epilepticus.

Three principal findings emerged from this work. 1) Addition of peptide Tat-pTrkBY816 to extracellular fluid bathing cultured rat cortical neurons potently inhibited TrkB-mediated activation of PLCγ1 in a concentration dependent manner as detected by pPLCγ1 783 immunoreactivity. 2) The phospho-, but not the Tat-scrambled-pTrkBY816 peptide was an effective inhibitor. 3) The inhibition of pPLCγ1 signaling by Tat-pTrkBY816 was selective in that TrkB-mediated activation of AKT and ERK signaling was not affected. It was concluded that Tat-pTrkBY816 provides a potent and selective inhibitor of TrkB-mediated activation of PLCγ1. In view of published evidence of fusion peptides containing the Tat sequence permeating the blood-brain barrier and exerting beneficial effects in animal models of human diseases, the Tat-pTrkBY816 and/or derivatives thereof offer immense promise for treatment of disorders of the human nervous system including, but not restricted to, epilepsy and neuropathic pain.

A chemical-genetic approach provided proof of concept evidence that inhibition of TrkB kinase suppresses both seizures (Liu et al., 2014, in press) and seizure-induced development of TLE and anxiety-like behavior (Liu, G. et al., (2013) *Neuron* 79:31-38), establishing a strong rationale for developing a therapeutic. Towards that end, we sought to identify the downstream signaling pathway by which TrkB kinase activation produced these pathologies and to develop a therapeutic targeting the responsible pathway. To accomplish these goals, genetically modified mice were utilized and a model of seizures and epilepsy induced by microinfusion of a chemoconvulsant, KA, into the amygdala. Four principal findings emerged. (1) Genetic inhibition of TrkB-mediated PLCγ1 signaling suppressed the prolonged seizures induced by KA. (2) This led to design of a peptide (pY816) that inhibited the interaction of TrkB with PLCγ1 and demonstration of its selective inhibition of TrkB-mediated PLCγ1 activation In vitro and in vivo. 3) Treatment with pY816 prior to administration of the chemoconvulsant suppressed seizures in a dose- and time-dependent manner 4) Treatment with pY816 initiated after chemoconvulsant-evoked seizures and continued for just three days suppressed both epilepsy and anxiety-like behavior when tested weeks later. This study elucidates the signaling pathway by which TrkB activation produces diverse neuronal activity-driven pathologies and demonstrates therapeutic benefits of an inhibitor of this pathway in an animal model in vivo.

To facilitate identification of a molecular target for a therapeutic, we sought to elucidate the signaling pathway through which the SE-induced activation of TrkB induced diverse pathologies. RTKs like TrkB convey signals by coupling binding of a ligand with their ectodomain to intracellular signaling cascades, a coupling accomplished by recruiting enzymes and/or adaptor proteins to motifs containing tyrosine residues that undergo autophosphorylation upon receptor activation. The robust inhibition of KA-evoked SE in the trkB$^{PLC/PLC}$ mutant mice demonstrate that genetically uncoupling TrkB from adaptor proteins and enzymes that bind the motif containing Y816 produces powerful anticonvulsant effects. That anticonvulsant effects similar to trkB$^{PLC/PLC}$ mice were observed in mice heterozygous for PLCγ1 implicates PLCγ1 as the dominant effector of the anticonvulsant effects of the trkB$^{PLC/PLC}$ mutation. This provides a strong rationale for development of therapeutic agents that disrupt the interaction of TrkB with PLCγ1. We focused on a motif within the C terminus of TrkB shown to be critical for its binding PLCγ1 (Obermeier, A. et al., (1993) *The EMBO journal* 12:933-941) and designed a peptide, pY816, to disrupt this interaction. The mechanism by which pY816 produces its desired consequences presumably involves its binding a sequence within the SH2 domains of PLCγ1, the net result being reduced binding of TrkB to PLCγ1; the ability of systemically administered pY816 to reduce the co-immunoprecipitation of TrkB and PLCγ1 is consistent with this mechanism. One advantage of selectively uncoupling binding of TrkB with PLCγ1 is that other TrkB signaling pathways would be left intact (Lai, K. O. et al., (2012) *Nature Neuroscience* 15:1506-1515; Minichiello, L. et 4 (2002) *Neuron* 36:121-137), an expectation supported by pY816 inhibition of pY783 PLCγ1 immunoreactivity without affecting pErk or pAkt immunoreactivity, either in vitro or in vivo (FIGS. 21A, 21C and 21F). Notably, phosphorylation of Y515 of TrkB and the subsequent binding of the adaptor protein, Shc, results in neuroprotective effects in cultured sympathetic neurons (Atwal, J. K. et al., (2000) *Neuron* 27:265-277), raising the possibility that TrkB-mediated activation of the Shc signaling pathway may promote neuroprotection following SE in vivo. That said, the extent to which TrkB signaling through Shc or other pathways contributed to the neuroprotective effects evident in pY816-treated animals (FIG. 28) is uncertain. A strategy of uncoupling a RTK from an effector protein was implemented in in vitro studies of the MET receptor tyrosine kinase (Bardelli, A. et al., (1998) *PNAS USA* 95:14379-14383). Identification of residues critical for the transforming potential of another RTK, a mutant MET receptor, led to design and electroporation of phosphopeptides that uncoupled signal transducers from MET; this resulted in inhibition of sprouting and migration of transformed cells in an in vitro assay (Bardelli, A. et al., (1998) *PNAS USA* 95:14379-14383). At this time, the strategy of treating a disease model in vivo by uncoupling a RTK from a signal transducer has not been successfully implemented. One reason may lie in limited bioavailability of a peptide inhibitor. That said, fusion of the tat sequence to the pTrkB peptide here facilitated its traversing cell membranes, accessing a target within the cytosol of neurons behind the blood-brain barrier. A second reason may lie in the many autophosphorylation sites within the cytoplasmic domain of an RTK such as the EGRF, each of which can recruit different SH2 and PTB domain-containing proteins (Lemmon, M. A. et al., (2010) *Cell* 141:1117-1134), perhaps precluding activation of a single signaling pathway by a single small peptide. By contrast, the few identified autophosphorylation sites within the cytoplasmic domain of TrkB may reduce redundancy of signaling and render this strategy feasible.

The pY816 peptide may provide a therapeutic for prevention of TLE. Currently there are no preventive or disease modifying therapies available for TLE. Clinical observations together with studies of animal models support the conclusion that an episode of prolonged seizures contributes to the emergence of severe TLE years later (Annegers, J. F. et al., (1987) *N Engl J Med* 316:493-498; French, J. A. et al., (1993) *Ann Neurol* 34:774-780; Tsai, M. H. et al., (2009) QJM 102, 57-62). The seizure free latent period (months to years in human and days to weeks in animal models of TLE) provides a therapeutic window for intervention aimed at preventing development of TLE (Loscher, W. et al., (2013) *Nature reviews Drug discovery* 12:757-776). In the model studied here, the transiently enhanced activation of PLCγ induced by SE occurred during the seizure free latent period (i.e. 3-5 days) following SE, leading us to examine the preventive effects of three days of treatment with pY816. That commencing treatment with pY816 following 40 minutes of SE was effective together with the short latency of access to emergency medical care of many patients with SE (Alldredge, B. K. et al., (2001) N Engl J Med 345:631-637) enhances the feasibility of this approach to preventive therapy. That just 3 days of treatment was sufficient to exert these beneficial effects many weeks later could minimize potential unwanted consequences of long-term exposure to preventive therapy.

The beneficial effects of pY816 in SE-induced abnormalities in the light-dark test implicate TrkB-mediated activation of PLCγ1 signaling in the pathogenesis of anxiety-like behavior Anxiety disorders are observed in patients with epilepsy, most commonly those with TLE in particular (Beyenburg, S. et al., (2005) *Epilepsy Behav* 7:161-171). Optogenetic activation of neuronal cell bodies within the basolateral nucleus of the amygdala (BLA) induce anxiety-like behaviors in rodents, behaviors mediated in part by BLA-induced activation of ventral hippocampal circuitry (Felix-Ortiz, A. C. et al., (2013) *Neuron* 79:658-664). It seems plausible that excessive activity within neurons of the BLA may produce lasting modifications of synapses within these circuits, the behavioral consequence of which is an anxiety disorder. Here the source of the abnormal activity could be the SE itself and/or the recurrent seizures observed for many weeks thereafter whereas clinically the source of such abnormal activity might be an emotionally traumatic experience (Helfer, V. et al., (1996) *Neuroscience* 73:971-978; Wang, D. V. et al., (2011) *PloS one* 6:e18739). Demonstration of abnormal activity within the amygdala in fMRI studies of patients with anxiety disorders such as post traumatic stress disorder is consistent with this idea (Rauch, S. L. et al., (2000) *Biological psychiatry* 47:769-776). If this idea is correct, the effectiveness of just three days of treatment with pY816 initiated after SE advances this peptide as a potential candidate for prevention of anxiety disorders arising after traumatic experiences in humans.

In sum, the present work establishes the therapeutic efficacy in vivo of a strategy in which a signal transducer (PLCγ1) is selectively uncoupled from a RTK (TrkB). Given the diversity of cancers and other diseases promoted by excessive activation of RTK signaling, this strategy is applicable to some RTKs in addition to TrkB. The fact that the sequence of pY816 is identical in mouse and human implies that pY816 itself should prove useful in prevention of TLE and anxiety-like behaviors in humans.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

---

We claim:

1. A method of uncoupling a receptor tyrosine kinase (RTK) from a signaling effector for treating a disorder of the nervous system in a subject, the method comprising inhibiting the physical interaction of an RTK with its signaling effector by administering a therapeutically effective amount of an interfering molecule to the subject,
   wherein the disorder of the nervous system is epilepsy or anxiety,
   and wherein the interfering molecule is a phosphopeptide comprising SEQ ID NO: 5.

2. A method of uncoupling tyrosine receptor kinase B (TrkB) from a TrkB signaling effector for treating a disorder of the nervous system in a subject, the method comprising administering a therapeutically effective amount of an interfering molecule,
   wherein the interfering molecule inhibits the physical interaction of TrkB with a signaling effector,
   wherein the disorder of the nervous system is epilepsy or anxiety,
   and wherein the interfering molecule is a phosphopeptide comprising SEQ ID NO: 5.

3. The method of claim 2, wherein the TrkB signaling effector is PLCγ1.

4. The method of claim 2, wherein the phosphopeptide comprises the amino acid sequence YGRKKRRQRRRLQNLAKASPVYLDI (SEQ ID NO: 1), wherein the amino acid at position 22 is phosphorylated; the amino acid sequence LQNLAKASPVYLDI (SEQ ID NO: 5); or the sequence YGRKKRRQRRRLQNLAKASPVpYLDI (SEQ ID NO: 3), wherein Y816 is phosphorylated (designated by p).

5. A method of uncoupling tyrosine receptor kinase B (TrkB) from a signaling effector for preventing onset or limiting the progression of a disorder of the nervous system in a subject, the method comprising administering to said subject a therapeutically effective amount of an interfering molecule,
   wherein the interfering molecule inhibits the physical interaction of TrkB with a signaling effector,
   wherein the disorder of the nervous system is epilepsy or anxiety,
   and wherein the interfering molecule is a phosphopeptide comprising SEQ ID NO: 5.

6. The method of claim 5, wherein the TrkB signaling effector is PLCγ1.

7. The method of claim 5, wherein the phosphopeptide comprises the amino acid sequence YGRKKRRQRRRLQNLAKASPVYLDI (SEQ ID NO: 1), wherein the amino acid at position 22 is phosphorylated; the amino acid sequence LQNLAKASPVYLDI (SEQ ID NO: 5); or the sequence YGRKKRRQRRRLQNLAKASPVpYLDI (SEQ ID NO: 3), wherein Y816 is phosphorylated (designated by p).

8. The method according to claim 1, claim 2 or claim 5, wherein said subject is a mammal.

9. The method according to claim 8, wherein said subject is a human.

10. A method of preventing epileptic seizures in a subject in need thereof, the method comprising uncoupling tyrosine receptor kinase B (TrkB) from phospholipase C gamma 1 (PLCγ1) by administering a therapeutically effective amount of an interfering molecule, wherein the interfering molecule is a phosphopeptide comprising SEQ ID NO: 5.

11. A method of ameliorating anxiety-like disorder in a subject in need thereof, the method comprising uncoupling tyrosine receptor kinase B (TrkB) from phospholipase C gamma 1 (PLCγ1) by administering a therapeutically effective amount of an interfering molecule, wherein the interfering molecule is a phosphopeptide comprising SEQ ID NO: 5.

12. The method of claim 10 or 11, wherein the phosphopeptide comprises the amino acid sequence YGRKKRRQRRRLQNLAKASPVYLDI (SEQ ID NO: 1), wherein the amino acid at position 22 is phosphorylated; the amino acid sequence LQNLAKASPVYLDI (SEQ ID NO: 5); or the sequence YGRKKRRQRRRLQNLAKASPVpYLDI (SEQ ID NO: 3), wherein Y816 is phosphorylated (designated by p).

* * * * *